United States Patent
Huang et al.

(10) Patent No.: US 7,897,602 B2
(45) Date of Patent: Mar. 1, 2011

(54) INDOLINONE COMPOUNDS AS KINASE INHIBITORS

(75) Inventors: Jiann-Jyh Huang, Xizhi (TW); Chao-Cheng Chiang, Xizhi (TW); Chiawei Liu, Xizhi (TW); Chun-Liang Lai, Xizhi (TW); Shu Fu Lin, Xizhi (TW); Yu-Hsiang Lin, Xizhi (TW); Ru-Wen Wang, Xizhi (TW); Sheng-Chuan Yang, Xizhi (TW); Jia-Ming Chang, Xizhi (TW); Shih-Hsien Chuang, Xizhi (TW); Paonien Chen, Xizhi (TW)

(73) Assignee: Development Center for Biotechnology, Taipei County (TW)

( * ) Notice: Subject to any disclaimer, the term of this patent is extended or adjusted under 35 U.S.C. 154(b) by 0 days.

(21) Appl. No.: 12/492,281

(22) Filed: Jun. 26, 2009

(65) Prior Publication Data
US 2010/0179146 A1    Jul. 15, 2010

Related U.S. Application Data

(60) Provisional application No. 61/144,065, filed on Jan. 12, 2009.

(51) Int. Cl.
| | |
|---|---|
| A61K 31/5377 | (2006.01) |
| A61K 31/496 | (2006.01) |
| A61K 31/454 | (2006.01) |
| A61K 31/404 | (2006.01) |
| C07D 413/14 | (2006.01) |
| C07D 403/14 | (2006.01) |
| C07D 401/14 | (2006.01) |
| C07D 403/06 | (2006.01) |

(52) U.S. Cl. .......... 514/235.2; 514/254.09; 514/323; 514/414; 544/144; 544/373; 546/201; 548/455; 548/468

(58) Field of Classification Search ............ 514/235.2, 514/414, 323, 339, 254.09; 548/455, 468; 544/373, 144; 546/201
See application file for complete search history.

(56) References Cited

U.S. PATENT DOCUMENTS

| | | | |
|---|---|---|---|
| 6,114,371 | A | 9/2000 | Tang |
| 6,130,238 | A | 10/2000 | Tang |
| 6,350,754 | B2 | 2/2002 | Tang |
| 6,579,897 | B2 | 6/2003 | Tang |
| 6,878,733 | B1 | 4/2005 | Shenoy |
| 2002/0187978 | A1 | 12/2002 | Tang |
| 2003/0069297 | A1 | 4/2003 | Cui |
| 2003/0119819 | A1 | 6/2003 | Liang |
| 2004/0186160 | A1 | 9/2004 | Tang |
| 2004/0266843 | A1 | 12/2004 | Howlett |
| 2006/0094682 | A1 | 5/2006 | Westwick |

FOREIGN PATENT DOCUMENTS
WO    2006/001954 A2    1/2006

OTHER PUBLICATIONS

Philip Cohen, The development and therapeutic potential of protein kinase inhibitors, 1999, Current Opinion in Chemical Biology, 3, pp. 459-465.*
Lala et al., Role of nitric oxide in tumor progression: Lessons from experimental tumors, 1998, Cancer and Metastasis Reviews, 17(1), pp. 91-106.*
Golub et al., Molecular Classification of Cancer: Class Discovery and Class Prediction by Gene Expression Monitoring, 1999, Science, vol. 286, pp. 531-537.*
Sun, et al., "Identification of Substituted 3-[4,5,6,7-Tetrahydro=1H-indol-2-yl) methylene]-1,3dihydroindol-2 ones as Growth Factor Receptor Inhibitors for VEGF-R2 (Flk-1/KDR), FGF-R1, and PDGF-Rβ Tyrosine Kinases", J. Med. Chem. 2000, 43, 2655-2663.
Guan, et al., "Design and Synthesis of Aminopropyl Tetrahydroindole-based Indolin-2-ones as Selective and Potent Inhibitors of Src and Yes Tyrosine Kinase", Biorganic & Medicinal Chemistry Letters 14 (2004) 187-190.

* cited by examiner

*Primary Examiner* — Kamal A Saeed
*Assistant Examiner* — Kristin Bianchi
(74) *Attorney, Agent, or Firm* — Occhiuti Rohlicek & Tsao LLP

(57) ABSTRACT

Indolinone compounds of formula (I) or (II):

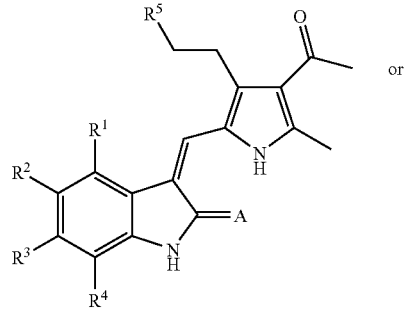

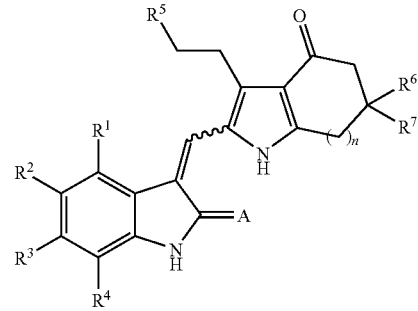

wherein A, $R^1$, $R^2$, $R^3$, $R^4$, $R^5$, $R^6$, $R^7$, and n are defined herein. Also disclosed are methods for decreasing the activity of a protein kinase and for treating a protein kinase-related disease, such as cancer, with these compounds.

40 Claims, No Drawings

INDOLINONE COMPOUNDS AS KINASE INHIBITORS

CROSS-REFERENCE TO RELATED APPLICATION

This application claims the benefit of the priority pursuant to 35 U.S.C. §119(e) of U.S. Provisional Patent Application No. 61/144,065, filed Jan. 12, 2009. The content of the prior application is incorporated herein by its entirety.

BACKGROUND

Protein kinases (PKs) play important roles in cellular signal pathways that regulate various cell functions such as differentiation, proliferation, migration, and apoptosis.

Abnormal PK activity has been linked to and observed in a number of diseases including cancer. See K Novak, MedGenMed. 2004; 6(2): 25. Thus, protein kinases are attractive therapeutic targets. PK inhibitors, compounds that block the activities of PKs, have been developed and used widely for clinical applications. For instance, tyrosine kinase inhibitors are useful in inhibiting T-cell proliferation and thus can be utilized as immunosuppressive agents for the prevention or treatment of graft rejection following transplant surgery and also for the prevention or treatment of autoimmune diseases (e.g., rheumatoid arthritis, psoriasis, and HIV-AIDS).

While more than thirty PK inhibitors are currently under clinical trial for cancer treatment, there is still a need for developing new PK inhibitors to treat various disorders.

SUMMARY

This invention is based on the unexpected discovery that certain indolinone compounds can inhibit activities of protein kinases (e.g., Aurora A and B, c-Met, VEGFr-2, FGFr-1, c-kit, PDGFr-β, and FLT3 kinases), which allows these compounds to be applied in treating protein kinase-related diseases including cancer.

In one aspect, this invention features an indolinone compound of formula (I):

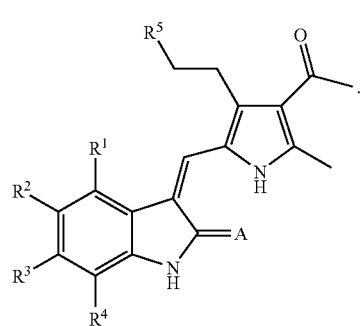

(I)

In this formula, A is O or S; $R^1$ is H, alkyl, alkenyl, alkynyl, halo, nitro, cyano, cycloalkyl, heterocycloalkyl, cycloalkenyl, heterocycloalkenyl, $OR^a$, $NR^aR^b$, —$S(O)_2R^a$, —$S(O)_2$NR$^a$R$^b$, —$C(O)R^a$, —$C(O)NR^aR^b$, —$NR^aC(O)R^b$, —$NR^aS(O)_2R^b$, —$N=CR^aR^b$, or —$NR^aC(O)NHR^b$, in which each of $R^a$ and $R^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or $R^a$ and $R^b$, together with the nitrogen atom to which they are bonded, are heteroaryl, heterocycloalkyl, or heterocycloalkenyl; each of $R^2$, $R^3$, and $R^4$, independently, is H, halo, nitro, cyano, aryl, heteroaryl, cycloalkyl, heterocycloalkyl, cycloalkenyl, heterocycloalkenyl, $OR^a$, $NR^aR^b$, —$S(O)_2R^a$, —$S(O)_2NR^aR^b$, —$C(O)R^a$, —$C(O)NR^aR^b$, —$NR^aC(O)R^b$, —$NR^aS(O)_2R^b$, —$N=CR^aR^b$, or —$NR^aC(O)NHR^b$; and $R^5$ is —$C(O)OR^c$, —$C(O)R^c$, —$C(O)NR^cR^d$, or —$CH_2NR^cR^d$, in which each of $R^c$ and $R^d$, independently, is H, alkyl, alkenyl, or alkynyl, or $R^c$ and $R^d$, together with the nitrogen atom to which they are bonded, are heteroaryl, heterocycloalkyl, or heterocycloalkenyl.

One subset of the above-described indolinone compounds includes those in which $R^5$ is —$C(O)NR^cR^d$, $R^c$ and $R^d$, together with the nitrogen atom to which they are bonded, being pyrrolidinyl, piperidinyl, piperazinyl, or morpholinyl, each optionally fused with aryl or heteroaryl, or heteroaryl. In these compounds, $R^2$ can be halo, —$S(O)_2R^a$, —$S(O)_2NR^aR^b$, or —$NR^aS(O)_2R^b$, in which each of $R^a$ and $R^b$, independently, is H, alkyl optionally substituted with aryl, aryl, or heteroaryl, or $R^a$ and $R^b$, together with the nitrogen atom to which they are bonded, are heteroaryl, heterocycloalkyl, or heterocycloalkenyl; or each of $R^1$, $R^3$, and $R^4$ can be H.

Another subset of the above-described indolinone compounds includes those in which at least one of $R^1$, $R^2$, $R^3$, and $R^4$ is —$N=CR^aR^b$ or —$NR^aC(O)NHR^b$.

Still another subset of the above-described indolinone compounds includes those in which $R^5$ is —$C(O)OR^c$ in which $R^c$ is H or alkyl, or $R^5$ is —$C(O)NR^cR^d$ in which one of $R^c$ and $R^d$ is H and the other is alkyl substituted with alkylamino. In these compounds, $R^2$ can be halo, —$S(O)_2R^a$, —$S(O)_2NR^aR^b$, or —$NR^aS(O)_2R^b$, in which each of $R^a$ and $R^b$, independently, is H or alkyl optionally substituted with aryl, aryl, or heteroaryl, or $R^a$ and $R^b$, together with the nitrogen atom to which they are bonded, are heteroaryl, heterocycloalkyl, or heterocycloalkenyl; or each of $R^1$, $R^3$, and $R^4$ can be H.

The term "alkyl" refers to a straight or branched monovalent saturated hydrocarbon containing, unless otherwise stated, 1-20 carbon atoms (e.g., $C_1$-$C_{10}$, $C_1$-$C_6$, or $C_1$-$C_4$). Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., $C_2$-$C_{10}$) and one or more double bonds. Examples of alkenyl include, but are not limited to, ethenyl, propenyl, allyl, and 1,4-butadienyl. The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, iso-propoxy, n-butoxy, iso-butoxy, sec-butoxy, and tert-butoxy. The term "acyloxy" refers to an O—C(O)—R radical in which R can be H, alkyl, alkenyl, alkynyl, cycloalkyl, cycloalkenyl, heterocycloalkyl, heterocycloalkenyl, aryl, or heteroaryl. The term "amino" refers to $NH_2$. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl. The terms "amido" and "carbamido" refer to —NRC(O)R' and —C(O)NRR' radicals respectively, in which each of R and R', independently, can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cycloheptyl, cyclooctyl, and adamantanyl. The term "cycloalkenyl" refers to a monovalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, piperidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "aryloxyl" refers to an —O-aryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, thiazolyl, pyrrolyl, isoquinolinyl, purinyl, oxazolyl, pyrazolyl, and carbazolyl.

Alkyl, alkenyl, alkynyl, cycloalkyl, heterocycloalkyl, cycloalkenyl, heterocycloalkenyl, amino, alkylamino, arylamino, alkoxy, aryloxy, aryl, and heteroaryl mentioned above include both substituted and unsubstituted moieties. Possible substituents on amino, alkylamino, arylamino, alkoxy, aryloxy, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)NH$_2$), carboxyl (—COOH), and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In another aspect, this invention relates to an indolinone compound of formula (II):

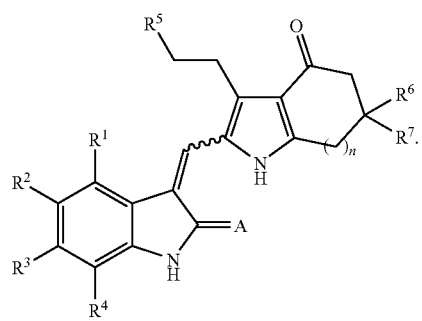

(II)

In formula (II), A is O or S; each of $R^1$, $R^2$, $R^3$, and $R^4$, independently, is H, halo, nitro, cyano, aryl, heteroaryl, cycloalkyl, heterocycloalkyl, cycloalkenyl, heterocycloalkenyl, $OR^a$, $NR^aR^b$, —$S(O)_2R^a$, —$S(O)_2NR^aR^b$, —$C(O)R^a$, —$C(O)NR^aR^b$, —$NR^aC(O)R^b$, —$NR^aS(O)_2R^b$, —N=$CR^aR^b$, or —$NR^aC(O)NHR^b$, in which each of $R^a$ and $R^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or $R^a$ and $R^b$, together with the nitrogen atom to which they are bonded, are heteroaryl, heterocycloalkyl, or heterocycloalkenyl; $R^5$ is —$C(O)OR^c$, —$C(O)R^c$, —$C(O)NR^cR^d$, or —$CH_2NR^cR^d$, in which each of $R^c$ and $R^d$, independently, is H, alkyl, alkenyl, or alkynyl, or $R^c$ and $R^d$, together with the nitrogen atom to which they are bonded, are heteroaryl, heterocycloalkyl, or heterocycloalkenyl; each of $R^6$ and $R^7$, independently, is H or alkyl; and n is 1 or 2. In particular, the indolinone compounds are those of formula (III):

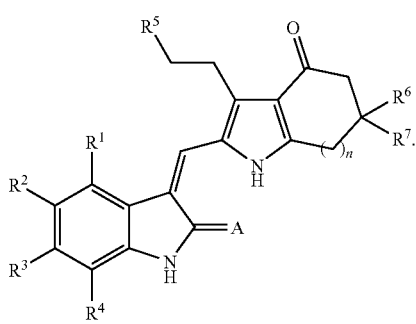

(III)

One subset of the just-described indolinone compounds includes those in which at least one of $R^1$, $R^2$, $R^3$, and $R^4$ is —N=$CR^aR^b$ or —$NR^aC(O)NHR^b$. In these compounds, one of $R^2$ and $R^3$ can be —N=$CR^aR^b$ or —$NR^aC(O)NHR^b$ and the other can be H; each of $R^1$ and $R^4$ can be H and $R^5$ can be —$C(O)OR^c$; or both $R^6$ and $R^7$ can be H or methyl.

Another subset of the indolinone compounds includes those in which $R^5$ is —$C(O)NR^cR^d$, $R^c$ and $R^d$, together with the nitrogen atom to which they are bonded, being pyrrolidinyl, piperidinyl, piperazinyl, morpholinyl, each optionally fused with aryl or heteroaryl, or heteroaryl. In these compounds, wherein one of $R^2$ and $R^3$ can be halo, —$S(O)_2R^a$, or —$S(O)_2NR^aR^b$ and the other can be H; each of $R^1$ and $R^4$ can be H; or both $R^6$ and $R^7$ can be H or methyl.

Yet another subset of the indolinone compounds described above includes those in which at least one of $R^2$, $R^3$, and $R^4$ is $NR^aR^b$, $-S(O)_2NR^aR^b$, or $-C(O)NR^aR^b$, $R^a$ and $R^b$, together with the nitrogen atom to which they are bonded, being pyrrolidinyl, piperidinyl, piperazinyl, morpholinyl, each optionally fused with aryl or heteroaryl, or heteroaryl. In these compounds, $R^5$ can be $-C(O)OR^c$; or each of $R^1$, $R^3$, and $R^4$ can be H.

Still another subset of the indolinone compounds includes those in which n is 2. In these compounds, $R^2$ can be $-NR^aS(O)_2R^b$; $R^5$ can be $-C(O)OR^c$; or each of $R^1$, $R^3$, $R^4$, $R^6$, and $R^7$ can be H.

The indolinone compounds described above also has another subset in which $R^5$ is $-C(O)OR^c$, $R^c$ being H or alkyl. In this subset of compounds, one of $R^2$ and $R^3$ can be H and the other can be H, halo, nitro, aryl, $-S(O)_2R^a$, $-S(O)_2NR^aR^b$, or $-NR^aS(O)_2R^b$; each of $R^1$ and $R^4$ can be H; or both $R^6$ and $R^7$ can be H or methyl.

The indolinone compounds described herein include the compounds themselves, as well as their salts (including pharmaceutically acceptable salts), their solvates (including pharmaceutically acceptable solvates), and their prodrugs, if applicable. A salt, for example, can be formed between an anion and a positively charged group (e.g., amino) on an indolinone compound. Suitable anions include chloride, bromide, iodide, sulfate, bisulfate, sulfamate, nitrate, phosphate, diphosphate, citrate, hydrochlorate, hydrobromate, sulfonate, methanesulfonate, p-toluenesulfonate, 2-hydroxyethylsulfonate, benzoate, salicylate, stearate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on an indolinone compound. Suitable cations include sodium ion, potassium ion, magnesium ion, calcium ion, and an ammonium cation such as tetramethylammonium ion. The indolinone compounds also include those salts containing quaternary nitrogen atoms. Examples of prodrugs include esters, amides, and other pharmaceutically acceptable derivatives, which, upon administration to a subject, are capable of providing active indolinone compounds.

In yet another aspect, this invention relates to a method of decreasing the activity of at least one protein kinase by contacting the at least one protein kinase with one or more indolinone compounds described above. The target protein kinase is Aurora A kinase, Aurora B kinase, VEGFr-2, FGFr-1, PDGFr-β, c-kit, c-Met, or FLT3.

Further, this invention relates to a method for treating for treating a protein kinase-related disease by administering to a subject in need thereof an effective amount of one or more indolinone compounds described above. The protein kinase-related disease can be a hyper-proliferation disorder (e.g., cancer), diabetes, a renal disease (e.g., a hyperproliferative disorder of the kidney), von Hippel-Lindau disease, fibrosis, osteoarthritis, an autoimmune diseases (e.g., psoriasis and rheumatoid arthritis), or a blood vessel proliferative disorder (e.g., atherosclerosis and restenosis). In particular, the protein kinase-related disease is cancer.

Also within the scope of this invention is a pharmaceutical composition containing one or more of the above-described indolinone compounds for use in treating a protein kinase-related disease such as cancer, as well as this therapeutic use and use of the compounds for the manufacture of a medicament for treating the disease.

The details of one or more embodiments of the invention are set forth in the description below. Other features, objects, and advantages of the invention will be apparent from the detailed description of embodiments and also from the appending claims.

DETAILED DESCRIPTION

Shown in Table 1 below are exemplary compounds of this invention.

TABLE 1

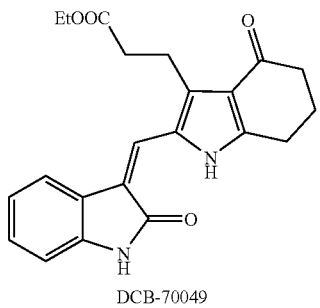

DCB-70049

(Z)-3-((3-(3-ethoxy-3-oxopropyl)-4-oxo-4,5,6,7-tetrahydro-1H-indol-2-yl)methylene)indolin-2-one

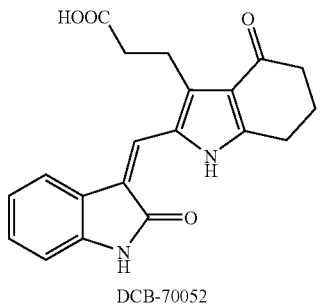

DCB-70052

(Z)-3-((3-carboxyethyl-4-oxo-4,5,6,7-tetrahydro-1H-indol-2-yl)methylene)indolin-2-one

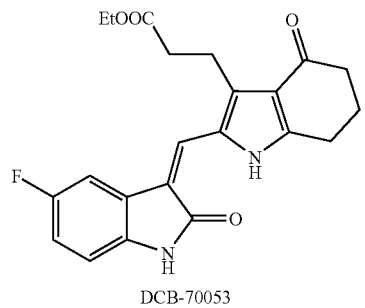

DCB-70053

(Z)-5-fluoro-3-((3-(3-ethoxy-3-oxopropyl)-4-oxo-4,5,6,7-tetrahydro-1H-indol-2-yl)methylene)indolin-2-one TABLE 1-continued

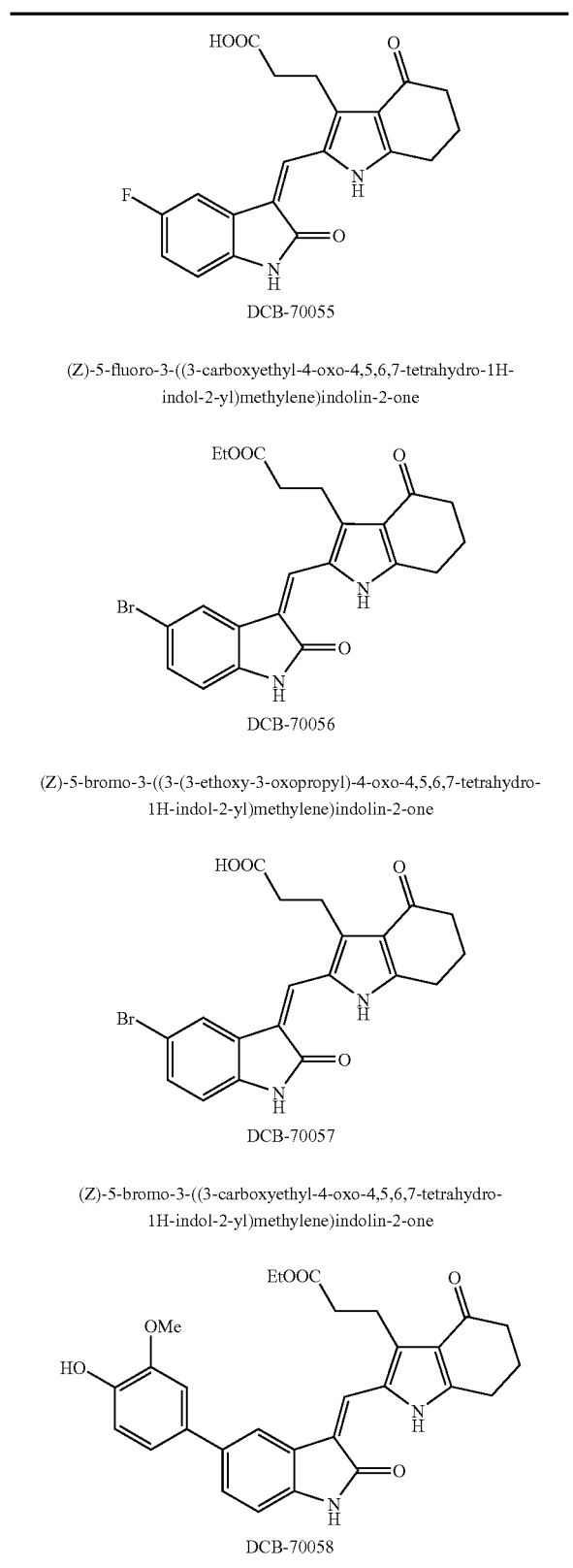

DCB-70055

(Z)-5-fluoro-3-((3-carboxyethyl-4-oxo-4,5,6,7-tetrahydro-1H-indol-2-yl)methylene)indolin-2-one

DCB-70056

(Z)-5-bromo-3-((3-(3-ethoxy-3-oxopropyl)-4-oxo-4,5,6,7-tetrahydro-1H-indol-2-yl)methylene)indolin-2-one

DCB-70057

(Z)-5-bromo-3-((3-carboxyethyl-4-oxo-4,5,6,7-tetrahydro-1H-indol-2-yl)methylene)indolin-2-one

DCB-70058

(Z)-5-(4-hydroxyl-3-methoxyphenyl)-3-((3-(3-ethoxy-3-oxopropyl)-4-oxo-4,5,6,7-tetrahydro-1H-indol-2-yl)methylene)indolin-2-one TABLE 1-continued

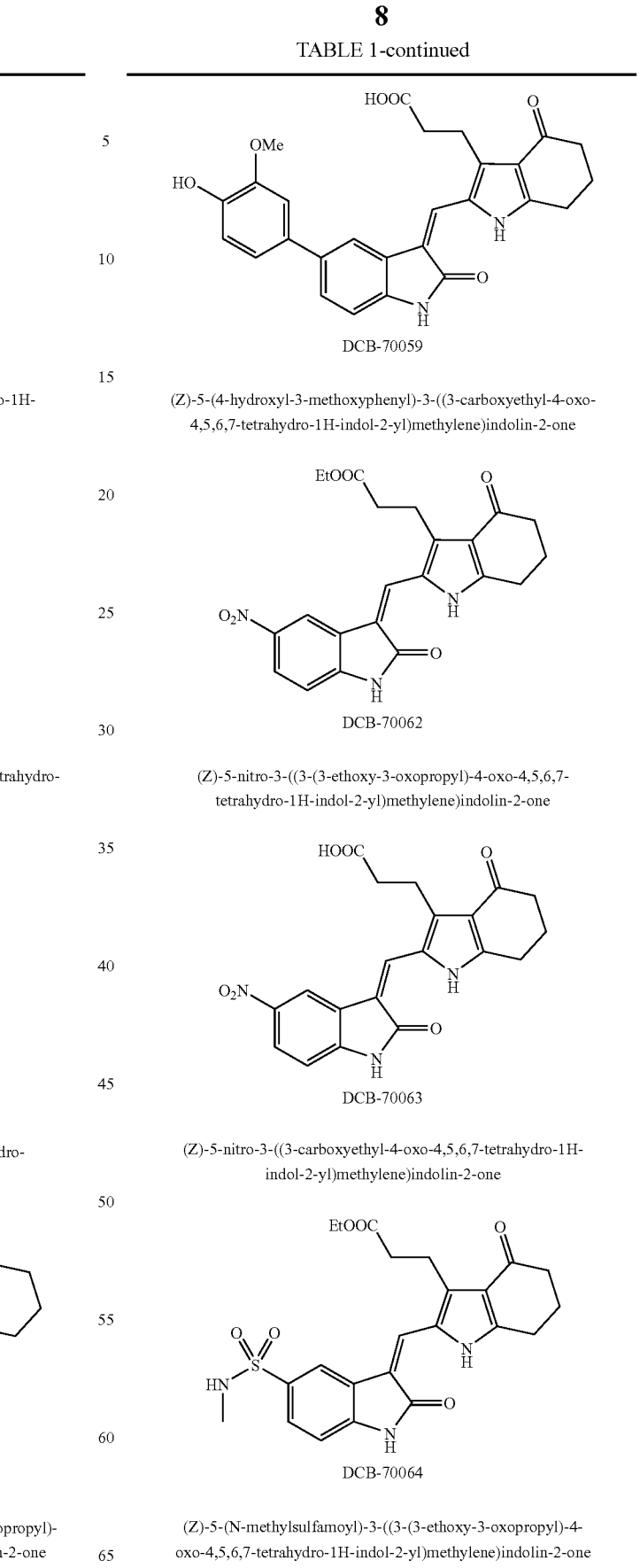

DCB-70059

(Z)-5-(4-hydroxyl-3-methoxyphenyl)-3-((3-carboxyethyl-4-oxo-4,5,6,7-tetrahydro-1H-indol-2-yl)methylene)indolin-2-one

DCB-70062

(Z)-5-nitro-3-((3-(3-ethoxy-3-oxopropyl)-4-oxo-4,5,6,7-tetrahydro-1H-indol-2-yl)methylene)indolin-2-one

DCB-70063

(Z)-5-nitro-3-((3-carboxyethyl-4-oxo-4,5,6,7-tetrahydro-1H-indol-2-yl)methylene)indolin-2-one

DCB-70064

(Z)-5-(N-methylsulfamoyl)-3-((3-(3-ethoxy-3-oxopropyl)-4-oxo-4,5,6,7-tetrahydro-1H-indol-2-yl)methylene)indolin-2-one TABLE 1-continued

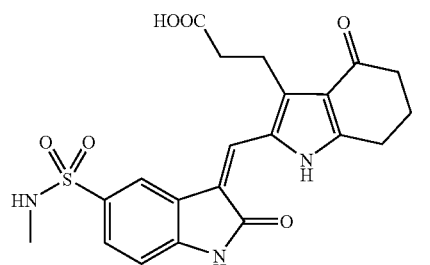

DCB-70065

(Z)-5-(N-methylsulfamoyl)-3-((3-carboxyethyl-4-oxo-4,5,6,7-tetrahydro-1H-indol-2-yl)methylene)indolin-2-one

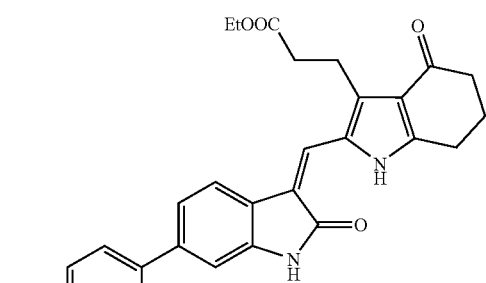

DCB-70066

(Z)-6-(4-hydroxyphenyl)-3-((3-(3-ethoxy-3-oxopropyl)-4-oxo-4,5,6,7-tetrahydro-1H-indol-2-yl)methylene)indolin-2-one

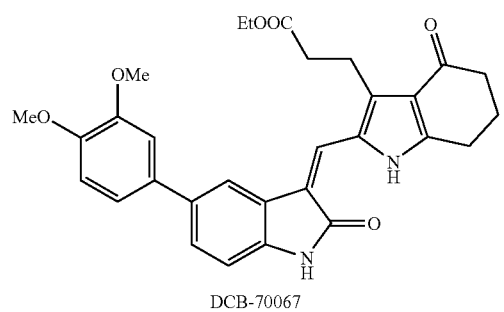

DCB-70067

(Z)-5-(3,4-dimethoxyphenyl)-3-((3-(3-ethoxy-3-oxopropyl)-4-oxo-4,5,6,7-tetrahydro-1H-indol-2-yl)methylene)indolin-2-one

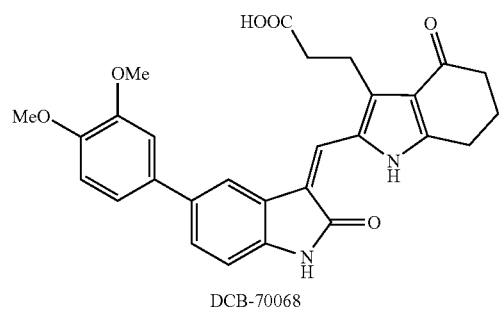

DCB-70068

(Z)-5-(3,4-dimethoxyphenyl)-3-((3-carboxyethyl-4-oxo-4,5,6,7-tetrahydro-1H-indol-2-yl)methylene)indolin-2-one TABLE 1-continued

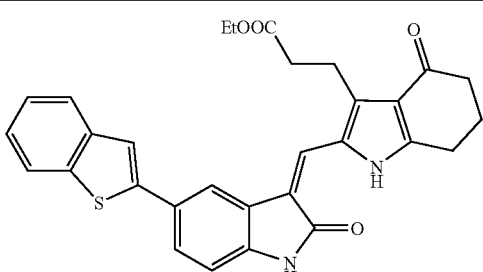

DCB-70069

(Z)-5-(benzo[b]thiophen-2-yl)-3-((3-(3-ethoxy-3-oxopropyl)-4-oxo-4,5,6,7-tetrahydro-1H-indol-2-yl)methylene)indolin-2-one

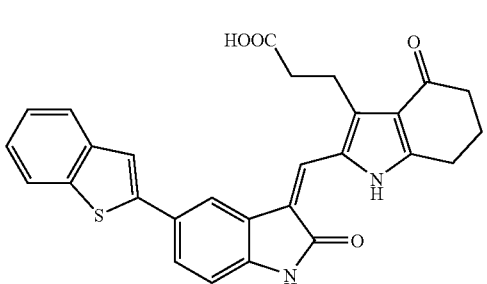

DCB-70070

(Z)-5-(benzo[b]thiophen-2-yl)-3-((3-carboxyethyl-4-oxo-4,5,6,7-tetrahydro-1H-indol-2-yl)methylene)indolin-2-one

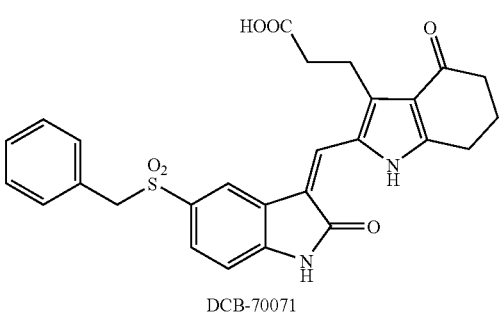

DCB-70071

(Z)-5-benzylsulfonyl-3-((3-carboxyethyl-4-oxo-4,5,6,7-tetrahydro-1H-indol-2-yl)methylene)indolin-2-one

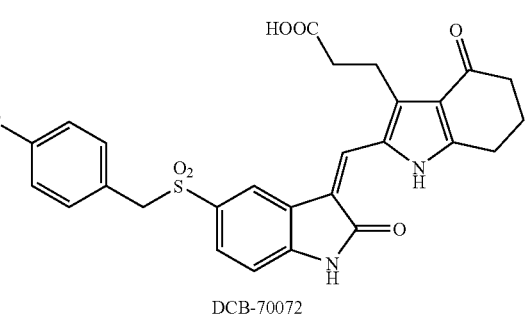

DCB-70072

(Z)-5-(4-fluorobenzylsulfonyl)-3-((3-carboxyethyl-4-oxo-4,5,6,7-tetrahydro-1H-indol-2-yl)methylene)indolin-2-one TABLE 1-continued

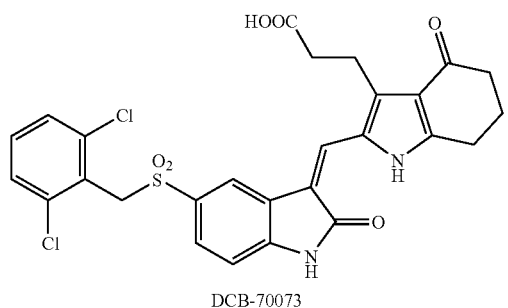

DCB-70073

(Z)-5-(2,6-dichlorobenzylsulfonyl)-3-((3-carboxyethyl-4-oxo-4,5,6,7-tetrahydro-1H-indol-2-yl)methylene)indolin-2-one

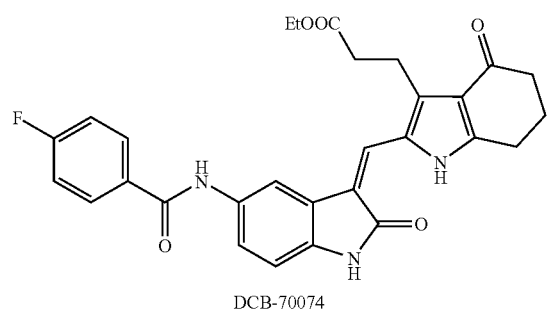

DCB-70074

(Z)-5-(4-fluorobenzamido)-3-((3-(3-ethoxy-3-oxopropyl)-4-oxo-4,5,6,7-tetrahydro-1H-indol-2-yl)methylene)indolin-2-one

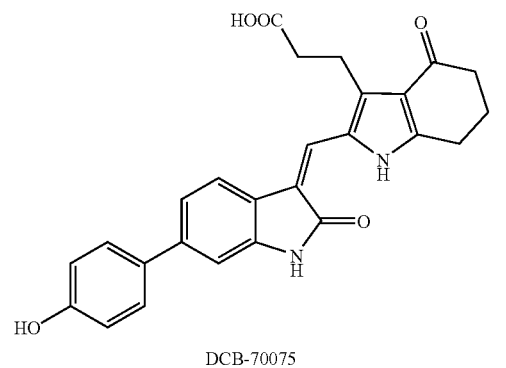

DCB-70075

(Z)-6-(4-hydroxyphenyl)-3-((3-carboxyethyl-4-oxo-4,5,6,7-tetrahydro-1H-indol-2-yl)methylene)indolin-2-one

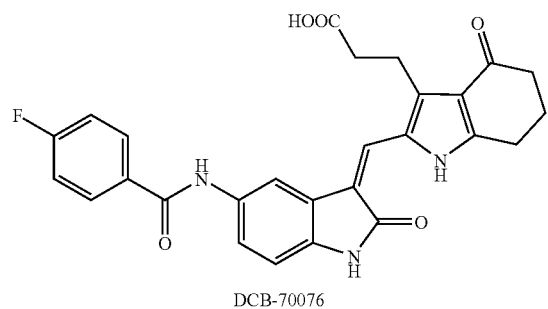

DCB-70076

(Z)-5-(4-fluorobenzamido)-3-((3-carboxyethyl-4-oxo-4,5,6,7-tetrahydro-1H-indol-2-yl)methylene)indolin-2-one

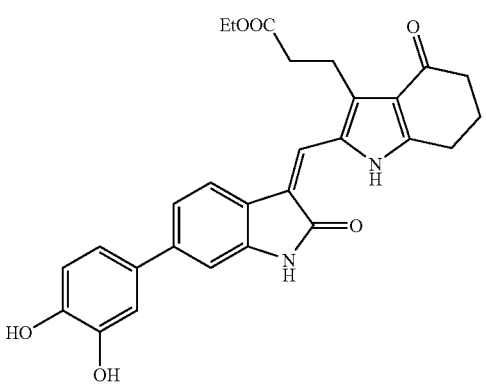

DCB-70077

(Z)-6-(3,4-dihydroxyphenyl)-3-((3-(3-ethoxy-3-oxopropyl)-4-oxo-4,5,6,7-tetrahydro-1H-indol-2-yl)methylene)indolin-2-one

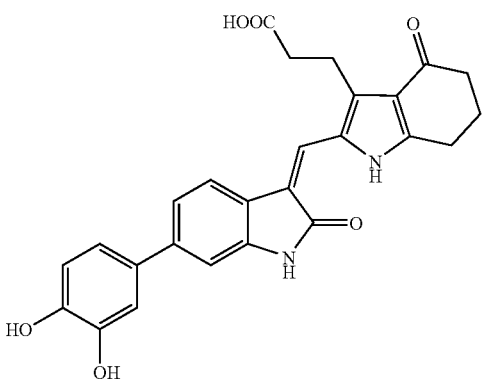

DCB-70078

(Z)-6-(3,4-dihydroxyphenyl)-3-((3-carboxyethyl-4-oxo-4,5,6,7-tetrahydro-1H-indol-2-yl)methylene)indolin-2-one

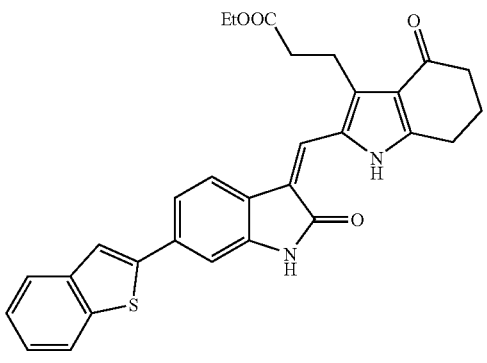

DCB-70079

(Z)-6-(benzo[b]thiophen-2-yl)-3-((3-(3-ethoxy-3-oxopropyl)-4-oxo-4,5,6,7-tetrahydro-1H-indol-2-yl)methylene)indolin-2-one TABLE 1-continued

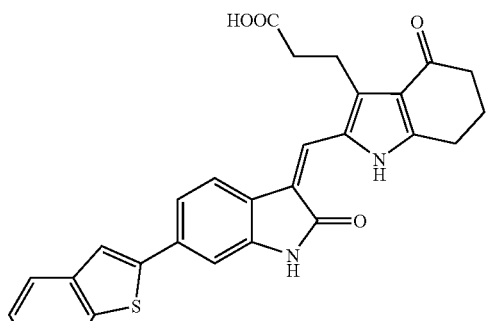

DCB-70080

(Z)-6-(benzo[b]thiophen-2-yl)-3-((3-carboxyethyl-4-oxo-
4,5,6,7-tetrahydro-1H-indol-2-yl)methylene)indolin-2-one

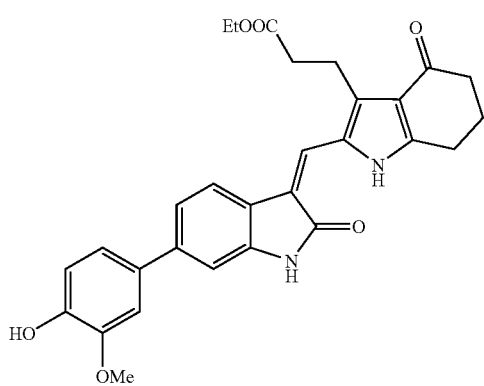

DCB-70081

(Z)-6-(4-hydroxy-3-methoxyphenyl)-3-((3-(3-ethoxy-3-oxopropyl)-
4-oxo-4,5,6,7-tetrahydro-1H-indol-2-yl)methylene)indolin-2-one

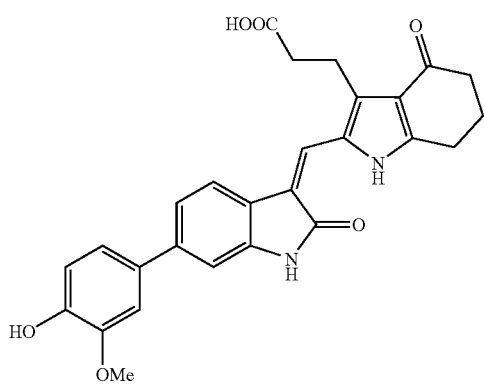

DCB-70082

(Z)-6-(4-hydroxy-3-methoxyphenyl)-3-((3-carboxyethyl-4-oxo-
4,5,6,7-tetrahydro-1H-indol-2-yl)methylene)indolin-2-one TABLE 1-continued

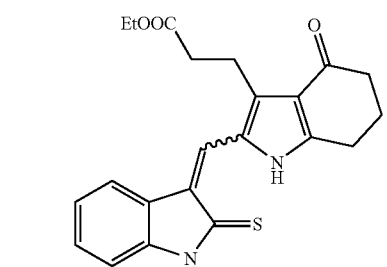

DCB-70083

3-((3-(3-ethoxy-3-oxopropyl)-4-oxo-4,5,6,7-tetrahydro-1H-
indol-2-yl)methylene)indolin-2-thione

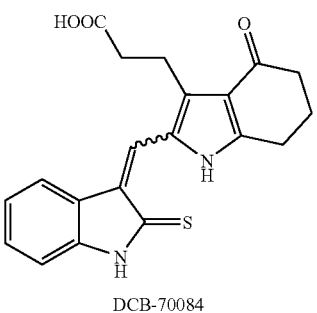

DCB-70084

3-((3-carboxyethyl-4-oxo-4,5,6,7-tetrahydro-1H-indol-2-
yl)methylene)indolin-2-thione

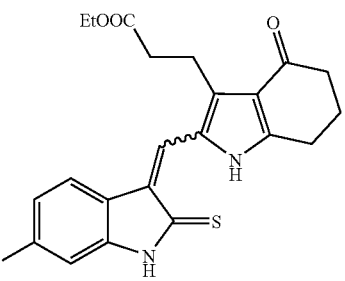

DCB-70085

6-bromo-3-((3-(3-ethoxy-3-oxopropyl)-4-oxo-4,5,6,7-
tetrahydro-1H-indol-2-yl)methylene)indolin-2-thione

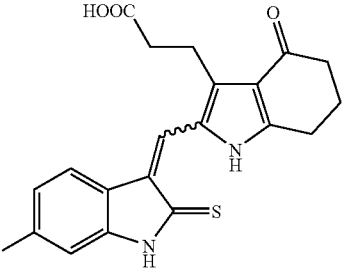

DCB-70086

6-bromo-3-((3-carboxyethyl-4-oxo-4,5,6,7-tetrahydro-
1H-indol-2-yl)methylene)indolin-2-thione TABLE 1-continued

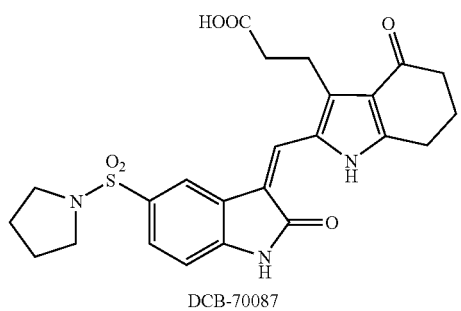

DCB-70087

(Z)-5-(pyrrolidin-1-ylsulfonyl)-3-((3-carboxyethyl-4-oxo-
4,5,6,7-tetrahydro-1H-indol-2-yl)methylene)indolin-2-one

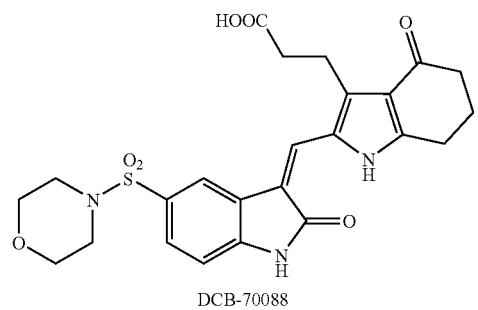

DCB-70088

(Z)-5-morpholinosulfonyl-3-((3-carboxyethyl-4-oxo-4,5,6,7-
tetrahydro-1H-indol-2-yl)methylene)indolin-2-one

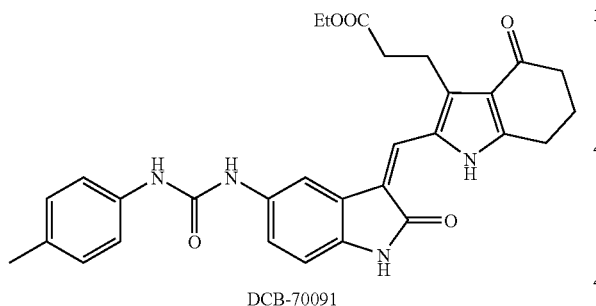

DCB-70091

(Z)-5-(3-p-tolylureido)-3-((3-(3-ethoxy-3-oxopropyl)-4-oxo-
4,5,6,7-tetrahydro-1H-indol-2-yl)methylene)indolin-2-one

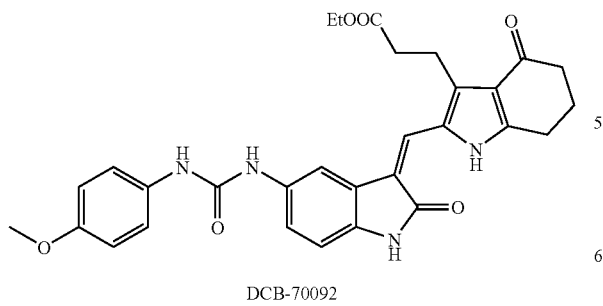

DCB-70092

(Z)-5-(3-(4-methoxyphenyl)ureido)-3-((3-(3-ethoxy-3-oxopropyl)-
4-oxo-4,5,6,7-tetrahydro-1H-indol-2-yl)methylene)indolin-2-one TABLE 1-continued

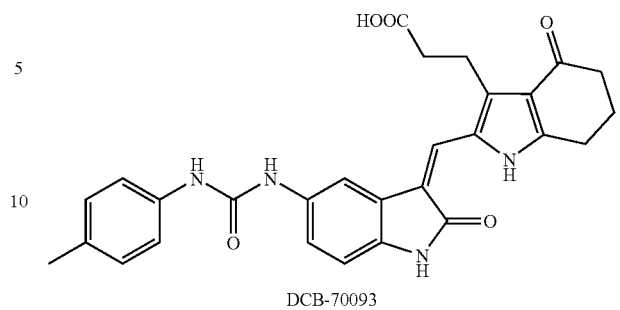

DCB-70093

(Z)-5-(3-p-tolylureido)-3-((3-carboxyethyl-4-oxo-4,5,6,7-
tetrahydro-1H-indol-2-yl)methylene)indolin-2-one

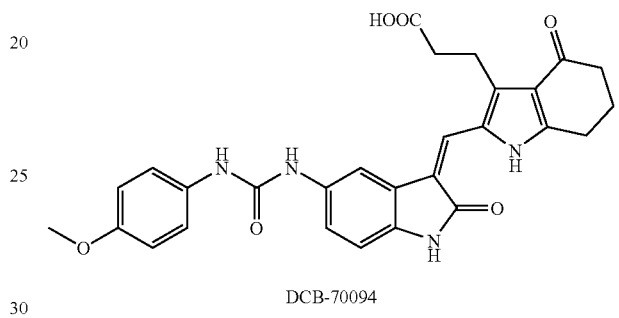

DCB-70094

(Z)-5-(3-(4-methoxyphenyl)ureido)-3-((3-carboxyethyl-4-oxo-
4,5,6,7-tetrahydro-1H-indol-2-yl)methylene)indolin-2-one

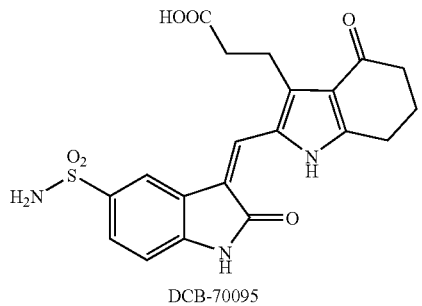

DCB-70095

(Z)-5-sulfamoyl-3-((3-carboxyethyl-4-oxo-4,5,6,7-tetrahydro-
1H-indol-2-yl)methylene)indolin-2-one

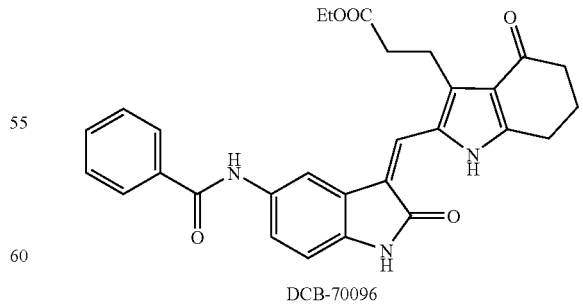

DCB-70096

(Z)-5-benazmido-3-((3-(3-ethoxy-3-oxopropyl)-4-oxo-4,5,6,7-
tetrahydro-1H-indol-2-yl)methylene)indolin-2-one TABLE 1-continued

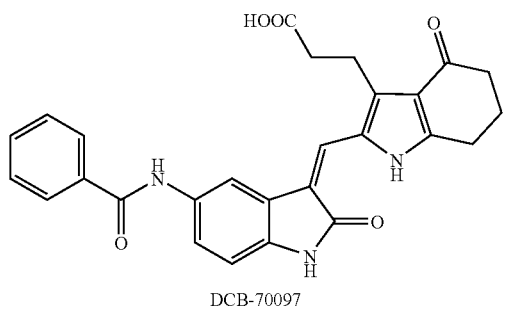

DCB-70097

(Z)-5-benazmido-3-((3-carboxyethyl-4-oxo-4,5,6,7-tetrahydro-1H-indol-2-yl)methylene)indolin-2-one

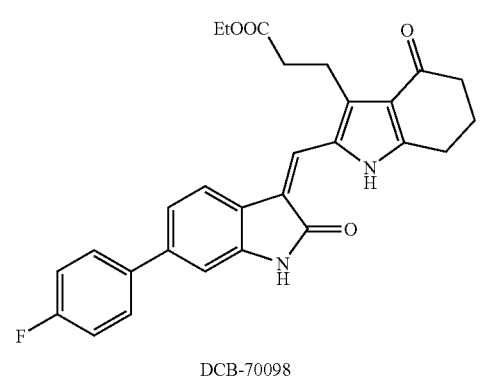

DCB-70098

(Z)-6-(4-fluorophenyl)-3-((3-(3-ethoxy-3-oxopropyl)-4-oxo-4,5,6,7-tetrahydro-1H-indol-2-yl)methylene)indolin-2-one

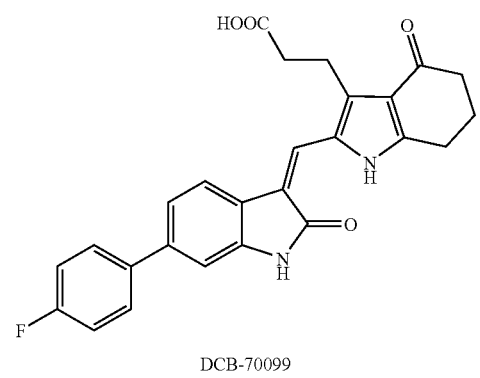

DCB-70099

(Z)-6-(4-fluorophenyl)-3-((3-carboxyethyl-4-oxo-4,5,6,7-tetrahydro-1H-indol-2-yl)methylene)indolin-2-one

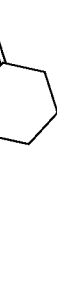

DCB-700100

(Z)-6-(3,5-difluorophenyl)-3-((3-(3-ethoxy-3-oxopropyl)-4-oxo-4,5,6,7-tetrahydro-1H-indol-2-yl)methylene)indolin-2-one

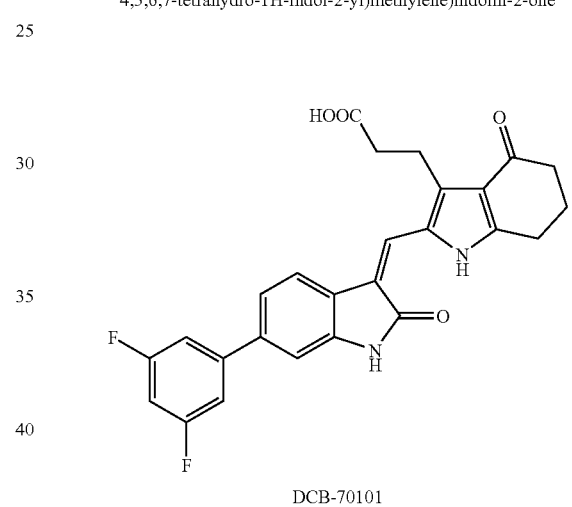

DCB-70101

(Z)-6-(3,5-difluorophenyl)-3-((3-carboxyethyl-4-oxo-4,5,6,7-tetrahydro-1H-indol-2-yl)methylene)indolin-2-one

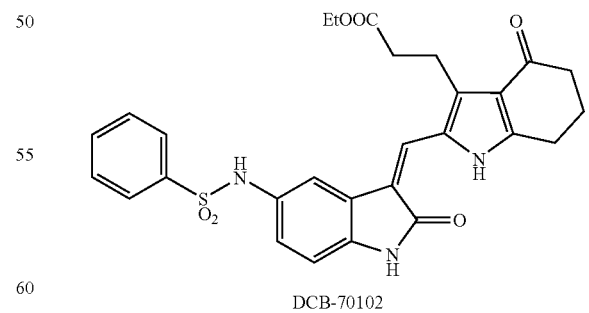

DCB-70102

(Z)-5-phenylsulfonamido-3-((3-(3-ethoxy-3-oxopropyl)-4-oxo-4,5,6,7-tetrahydro-1H-indol-2-yl)methylene)indolin-2-one TABLE 1-continued

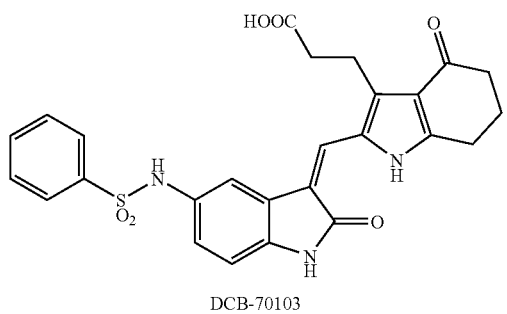

DCB-70103

(Z)-5-phenylsulfonamido-3-((3-carboxyethyl-4-oxo-4,5,6,7-tetrahydro-1H-indol-2-yl)methylene)indolin-2-one

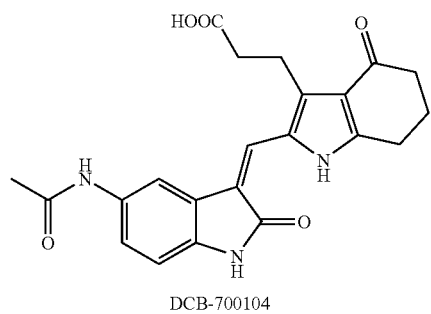

DCB-700104

(Z)-5-acetamido-3-((3-carboxyethyl-4-oxo-4,5,6,7-tetrahydro-1H-indol-2-yl)methylene)indolin-2-one

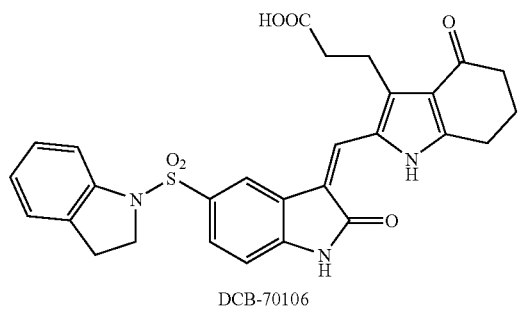

DCB-70106

(Z)-5-(indolin-1-ylsulfonyl)-3-((3-carboxyethyl-4-oxo-4,5,6,7-tetrahydro-1H-indol-2-yl)methylene)indolin-2-one

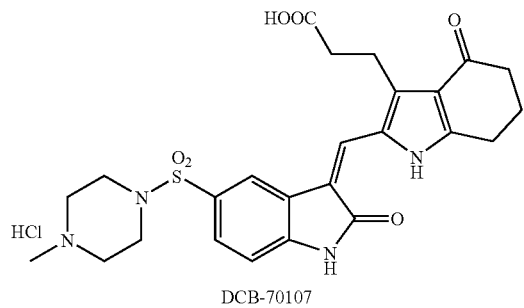

DCB-70107

(Z)-5-(4-methylpiperazin-1-ylsunfonyl)-3-((3-carboxyethyl-4-oxo-4,5,6,7-tetrahydro-1H-indol-2-yl)methylene)indolin-2-one hydrochloride TABLE 1-continued

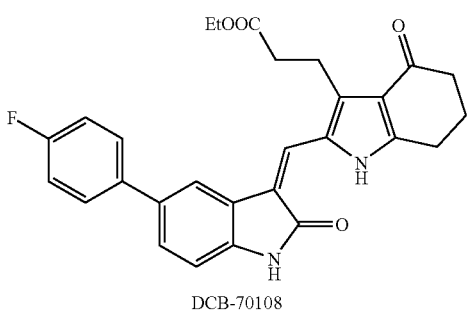

DCB-70108

(Z)-5-(4-fluorophenyl)-3-((3-(3-ethoxy-3-oxopropyl)-4-oxo-4,5,6,7-tetrahydro-1H-indol-2-yl)methylene)indolin-2-one

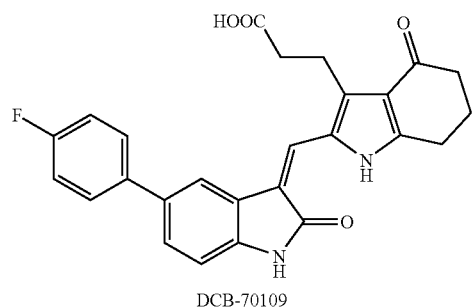

DCB-70109

(Z)-5-(4-fluorophenyl)-3-((3-carboxyethyl-4-oxo-4,5,6,7-tetrahydro-1H-indol-2-yl)methylene)indolin-2-one

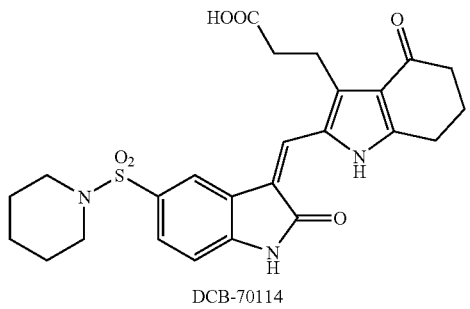

DCB-70114

(Z)-5-(piperidin-1-ylsulfonyl)-3-((3-carboxyethyl-4-oxo-4,5,6,7-tetrahydro-1H-indol-2-yl)methylene)indolin-2-one

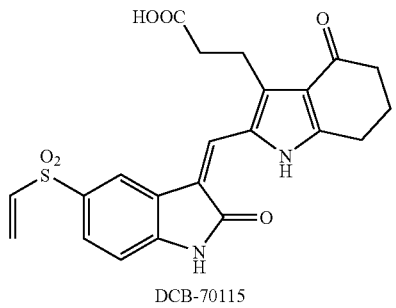

DCB-70115

(Z)-5-vinylsulfonyl-3-((3-carboxyethyl-4-oxo-4,5,6,7-tetrahydro-1H-indol-2-yl)methylene)indolin-2-one TABLE 1-continued

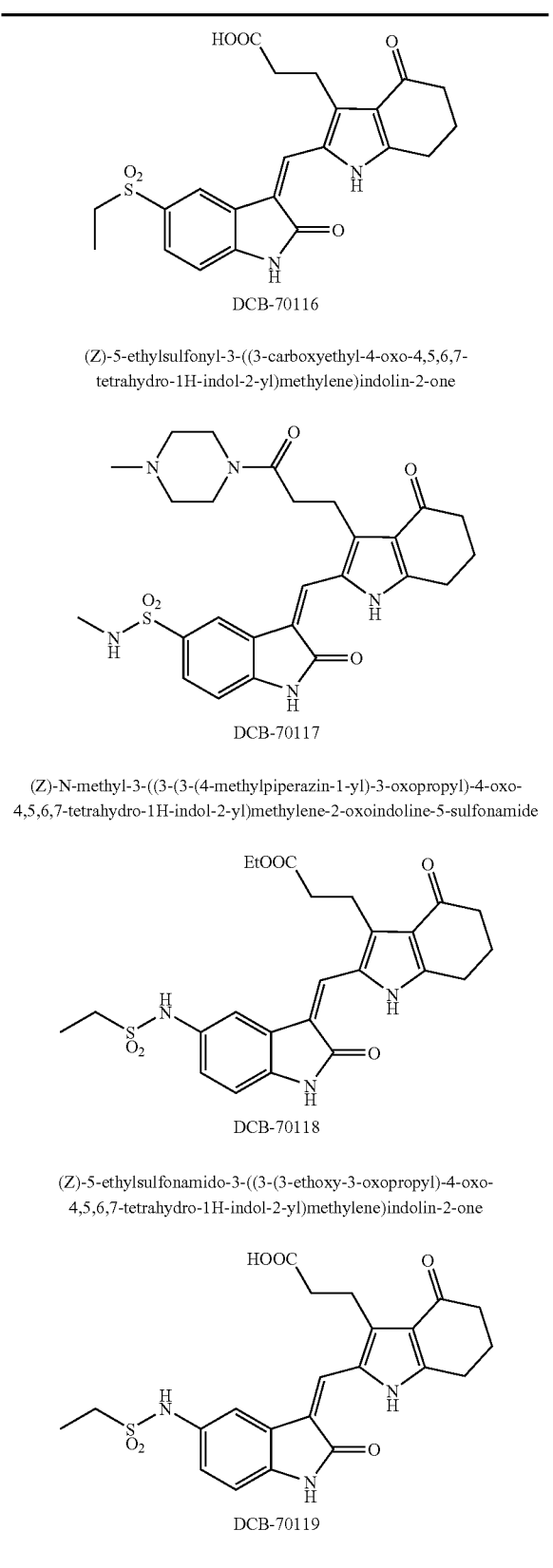

DCB-70116

(Z)-5-ethylsulfonyl-3-((3-carboxyethyl-4-oxo-4,5,6,7-tetrahydro-1H-indol-2-yl)methylene)indolin-2-one

DCB-70117

(Z)-N-methyl-3-((3-(3-(4-methylpiperazin-1-yl)-3-oxopropyl)-4-oxo-4,5,6,7-tetrahydro-1H-indol-2-yl)methylene-2-oxoindoline-5-sulfonamide

DCB-70118

(Z)-5-ethylsulfonamido-3-((3-(3-ethoxy-3-oxopropyl)-4-oxo-4,5,6,7-tetrahydro-1H-indol-2-yl)methylene)indolin-2-one

DCB-70119

(Z)-5-ethylsulfonamido-3-((3-(3-carboxyethyl-4-oxo-4,5,6,7-tetrahydro-1H-indol-2-yl)methylene)indolin-2-one TABLE 1-continued

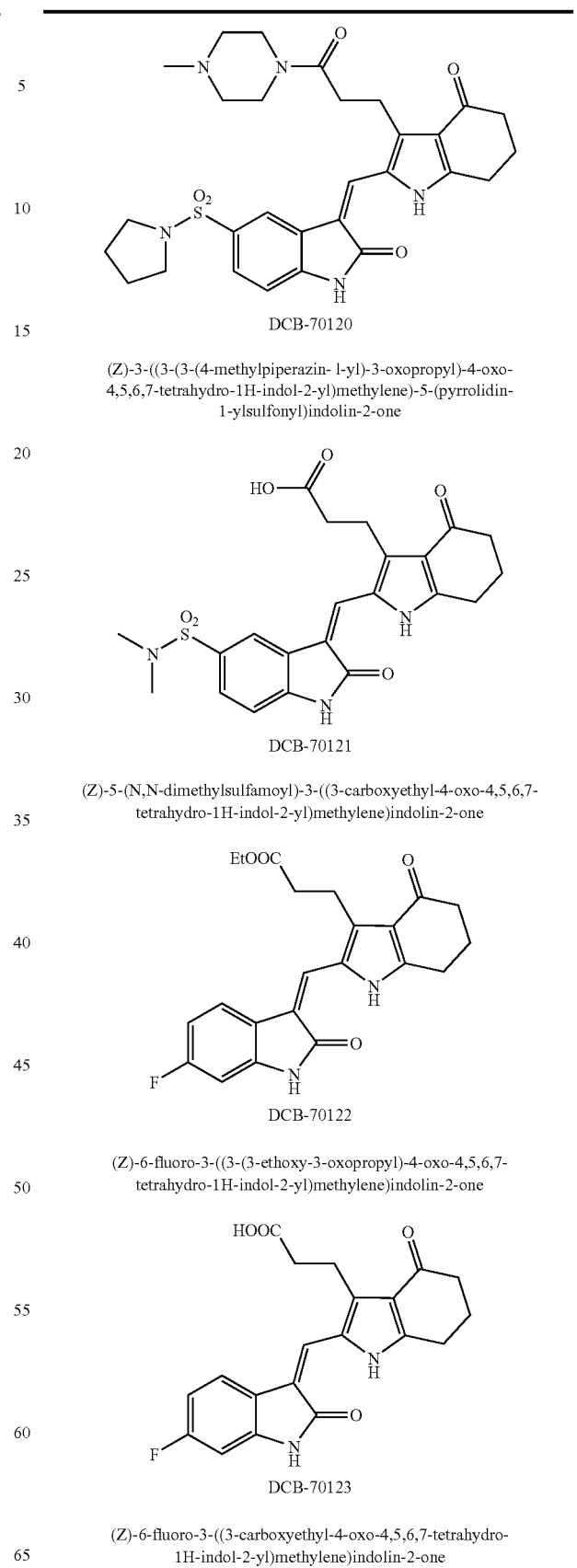

DCB-70120

(Z)-3-((3-(3-(4-methylpiperazin-1-yl)-3-oxopropyl)-4-oxo-4,5,6,7-tetrahydro-1H-indol-2-yl)methylene)-5-(pyrrolidin-1-ylsulfonyl)indolin-2-one

DCB-70121

(Z)-5-(N,N-dimethylsulfamoyl)-3-((3-carboxyethyl-4-oxo-4,5,6,7-tetrahydro-1H-indol-2-yl)methylene)indolin-2-one

DCB-70122

(Z)-6-fluoro-3-((3-(3-ethoxy-3-oxopropyl)-4-oxo-4,5,6,7-tetrahydro-1H-indol-2-yl)methylene)indolin-2-one

DCB-70123

(Z)-6-fluoro-3-((3-carboxyethyl-4-oxo-4,5,6,7-tetrahydro-1H-indol-2-yl)methylene)indolin-2-one TABLE 1-continued

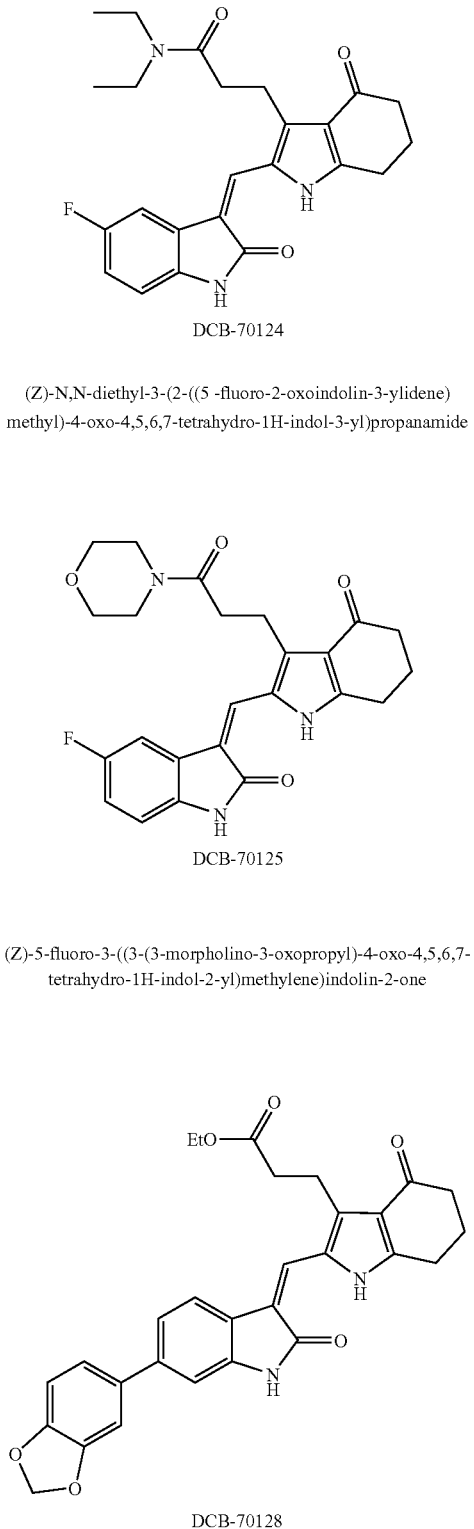

DCB-70124

(Z)-N,N-diethyl-3-(2-((5-fluoro-2-oxoindolin-3-ylidene)methyl)-4-oxo-4,5,6,7-tetrahydro-1H-indol-3-yl)propanamide

DCB-70125

(Z)-5-fluoro-3-((3-(3-morpholino-3-oxopropyl)-4-oxo-4,5,6,7-tetrahydro-1H-indol-2-yl)methylene)indolin-2-one

DCB-70128

(Z)-ethyl 3-(2-((6-(benzo[d][1,3]dioxol-5-yl)-2-oxoindolin-3-ylidene)methyl)-4-oxo-4,5,6,7-tetrahydro-1H-indol-3-yl)propanoate

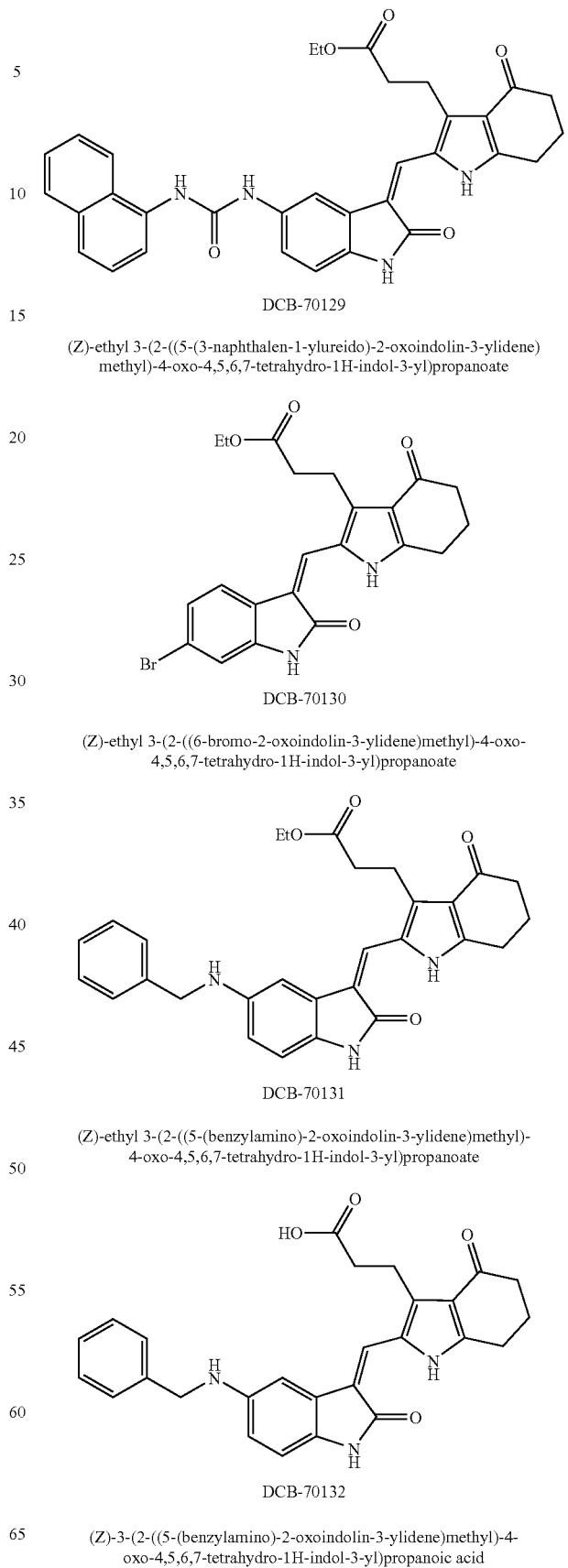

DCB-70129

(Z)-ethyl 3-(2-((5-(3-naphthalen-1-ylureido)-2-oxoindolin-3-ylidene)methyl)-4-oxo-4,5,6,7-tetrahydro-1H-indol-3-yl)propanoate

DCB-70130

(Z)-ethyl 3-(2-((6-bromo-2-oxoindolin-3-ylidene)methyl)-4-oxo-4,5,6,7-tetrahydro-1H-indol-3-yl)propanoate

DCB-70131

(Z)-ethyl 3-(2-((5-(benzylamino)-2-oxoindolin-3-ylidene)methyl)-4-oxo-4,5,6,7-tetrahydro-1H-indol-3-yl)propanoate

DCB-70132

(Z)-3-(2-((5-(benzylamino)-2-oxoindolin-3-ylidene)methyl)-4-oxo-4,5,6,7-tetrahydro-1H-indol-3-yl)propanoic acid TABLE 1-continued

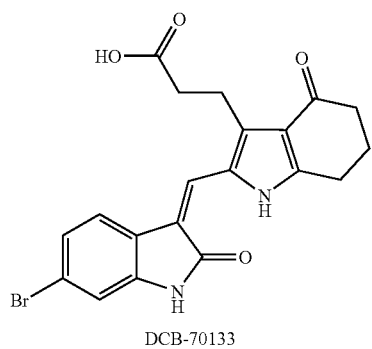

DCB-70133

(Z)-3-(2-((6-bromo-2-oxoindolin-3-ylidene)methyl)-4-oxo-4,5,6,7-tetrahydro-1H-indol-3-yl)propanoic acid

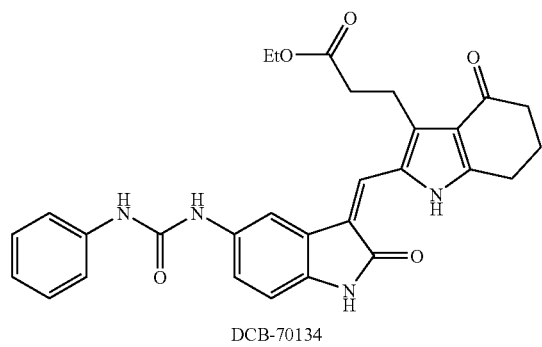

DCB-70134

(Z)-ethyl 3-(4-oxo-2-((2-oxo-5-(3-phenylureido)indolin-3-ylidene)methyl)-4,5,6,7-tetrahydro-1H-indol-3-yl)propanoate

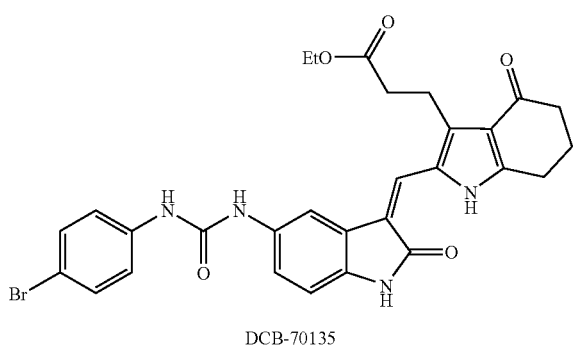

DCB-70135

(Z)-ethyl 3-(2-((5-(3-(4-bromophenyl)ureido)-2-oxoindolin-3-ylidene)methyl)-4-oxo-4,5,6,7-tetrahydro-1H-indol-3-yl)propanoate TABLE 1-continued

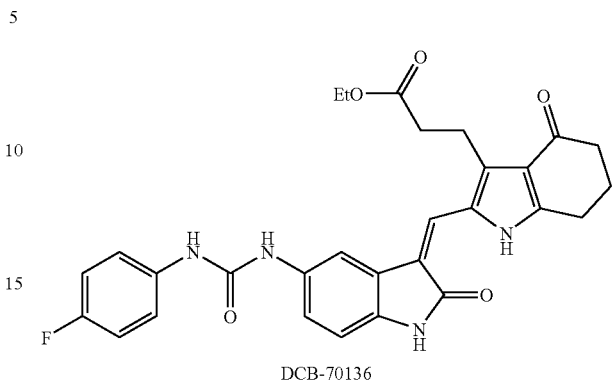

DCB-70136

(Z)-ethyl 3-(2-((5-(3-(4-fluorophenyl)ureido)-2-oxoindolin-3-ylidene)methyl)-4-oxo-4,5,6,7-tetrahydro-1H-indol-3-yl)propanoate

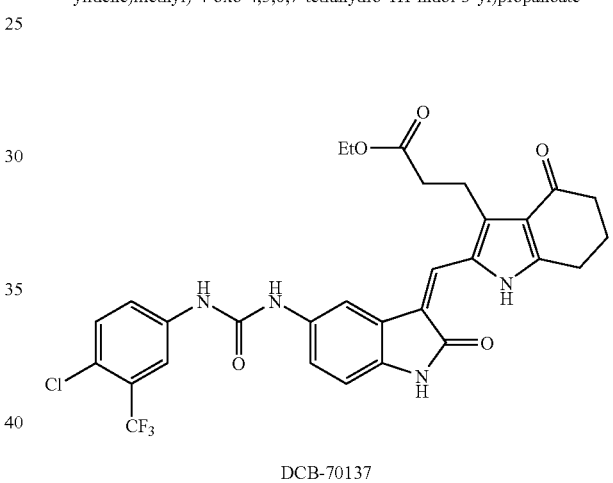

DCB-70137

(Z)-ethyl 3-(2-((5-(3-(4-chloro-3-(trifluoromethyl)phenyl)ureido)-2-oxoindolin-3-ylidene)methyl)-4-oxo-4,5,6,7-tetrahydro-1H-indol-3-yl)propanoate

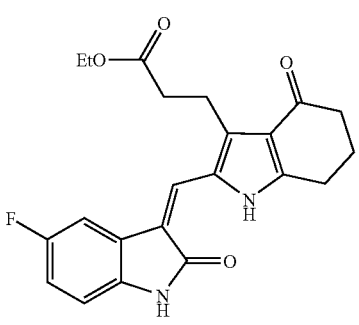

DCB-70138

(Z)-ethyl 3-(2-((5-fluoro-2-oxoindohn-3-yhdene)methyl)-4-oxo-1,4,5,6,7,8-hexahydrocyclohepta[b]pyrrol-3-yl)propanoate TABLE 1-continued

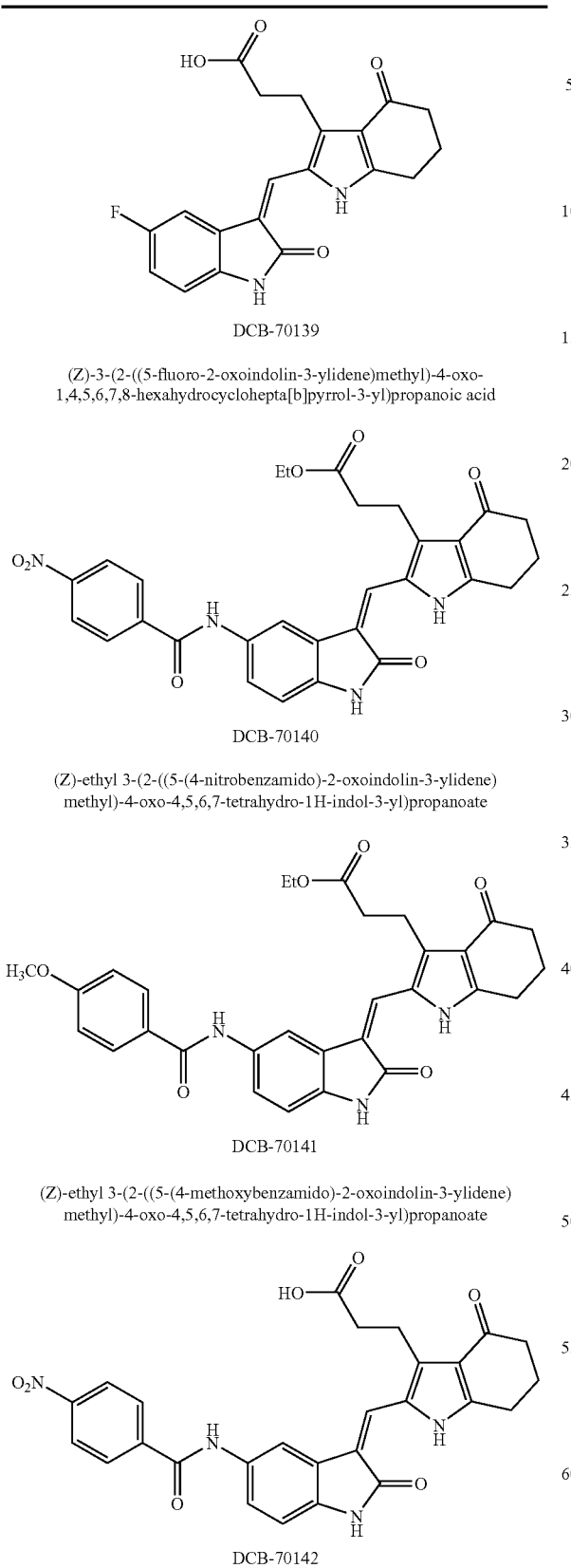

DCB-70139

(Z)-3-(2-((5-fluoro-2-oxoindolin-3-ylidene)methyl)-4-oxo-
1,4,5,6,7,8-hexahydrocyclohepta[b]pyrrol-3-yl)propanoic acid

DCB-70140

(Z)-ethyl 3-(2-((5-(4-nitrobenzamido)-2-oxoindolin-3-ylidene)
methyl)-4-oxo-4,5,6,7-tetrahydro-1H-indol-3-yl)propanoate

DCB-70141

(Z)-ethyl 3-(2-((5-(4-methoxybenzamido)-2-oxoindolin-3-ylidene)
methyl)-4-oxo-4,5,6,7-tetrahydro-1H-indol-3-yl)propanoate

DCB-70142

(Z)-3-(2-((5-(4-nitrobenzamido)-2-oxoindolin-3-ylidene)
methyl)-4-oxo-4,5,6,7-tetrahydro-1H-indol-3-yl)propanoic acid TABLE 1-continued

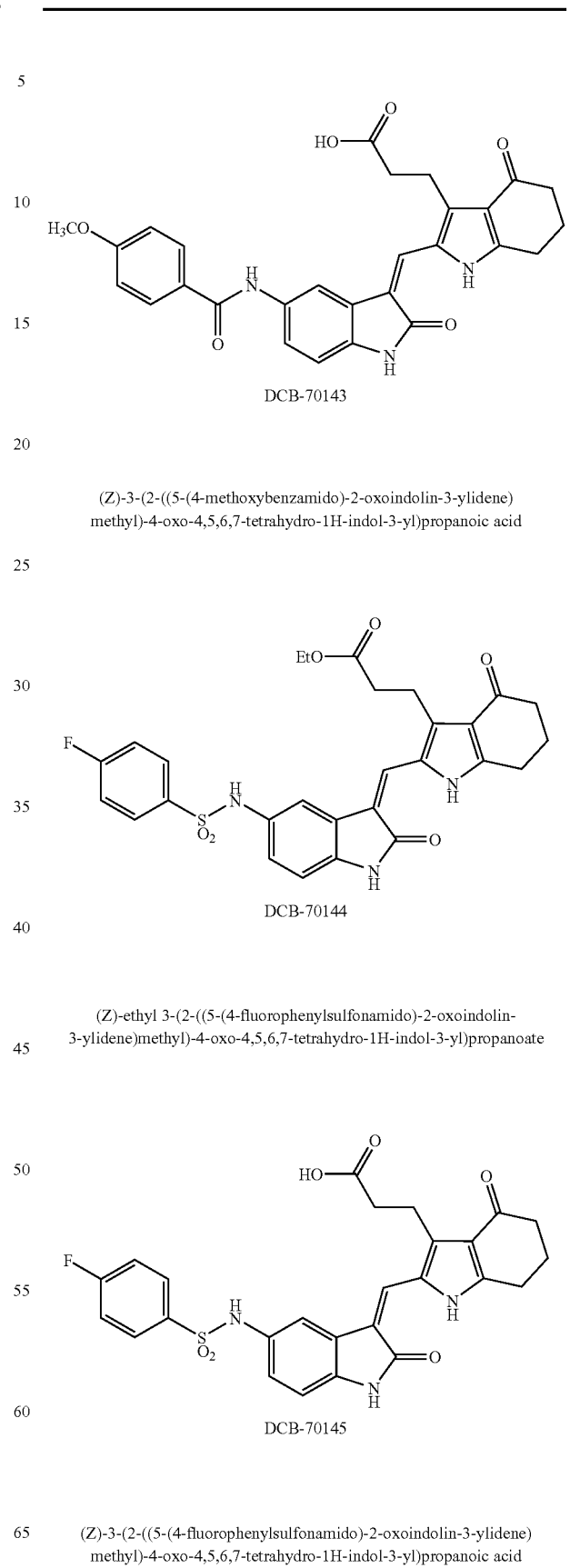

DCB-70143

(Z)-3-(2-((5-(4-methoxybenzamido)-2-oxoindolin-3-ylidene)
methyl)-4-oxo-4,5,6,7-tetrahydro-1H-indol-3-yl)propanoic acid

DCB-70144

(Z)-ethyl 3-(2-((5-(4-fluorophenylsulfonamido)-2-oxoindolin-
3-ylidene)methyl)-4-oxo-4,5,6,7-tetrahydro-1H-indol-3-yl)propanoate

DCB-70145

(Z)-3-(2-((5-(4-fluorophenylsulfonamido)-2-oxoindolin-3-ylidene)
methyl)-4-oxo-4,5,6,7-tetrahydro-1H-indol-3-yl)propanoic acid TABLE 1-continued

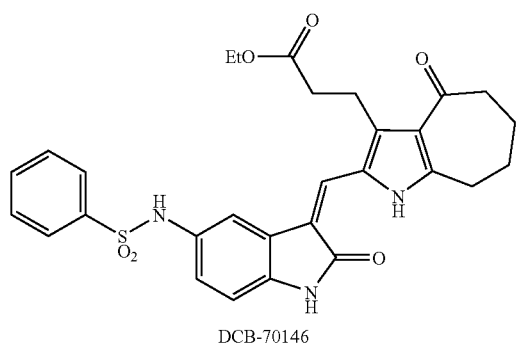

DCB-70146

(Z)-ethyl 3-(4-oxo-2-((2-oxo-5-(phenylsulfonamido)indolin-3-ylidene)methyl)-1,4,5,6,7,8-hexahydrocyclohepta[b]pyrrol-3-yl)propanoate

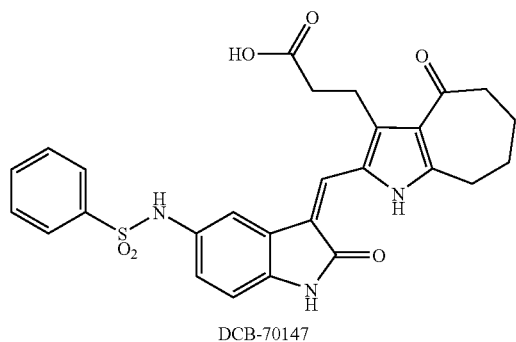

DCB-70147

(Z)-3-(4-oxo-2-((2-oxo-5-(phenylsulfonamido)indolin-3-ylidene)methyl)-1,4,5,6,7,8-hexahydrocyclohepta[b]pyrrol-3-yl)propanoic acid

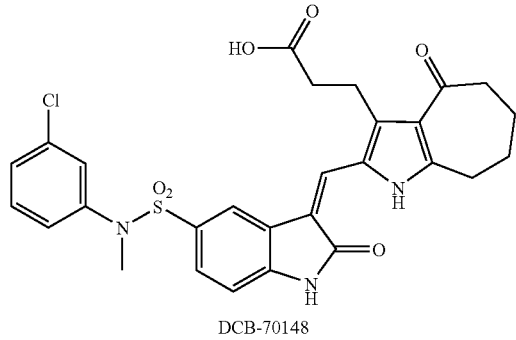

DCB-70148

(Z)-3-(2-((5-(N-(3-chlorophenyl)-N-methylsulfamoyl)-2-oxoindolin-3-ylidene)methyl)-4-oxo-1,4,5,6,7,8-hexahydrocyclohepta[b]pyrrol-3-yl)propanoic acid TABLE 1-continued

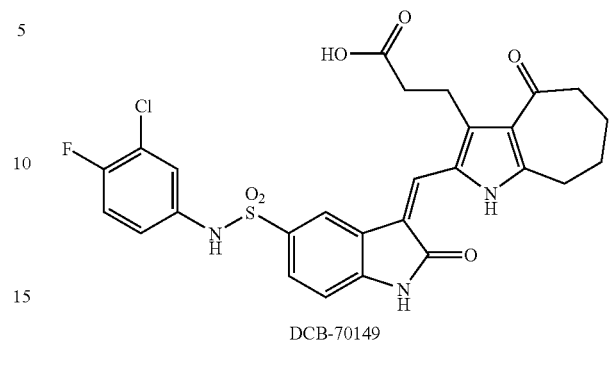

DCB-70149

(Z)-3-(2-((5-(N-(3-chloro-4-fluorophenyl)sulfamoyl)-2-oxoindolin-3-ylidene)methyl)-4-oxo-1,4,5,6,7,8-hexahydrocyclohepta[b]pyrrol-3-yl)propanoic acid

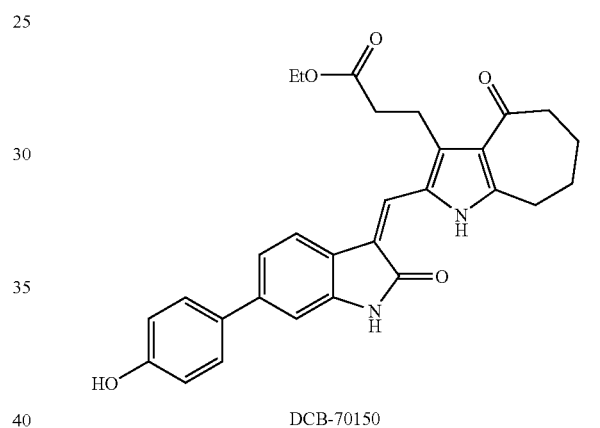

DCB-70150

(Z)-ethyl 3-(2-((6-(4-hydroxyphenyl)-2-oxoindolin-3-ylidene)methyl)-4-oxo-1,4,5,6,7,8-hexahydrocyclohepta[b]pyrrol-3-yl)propanoate

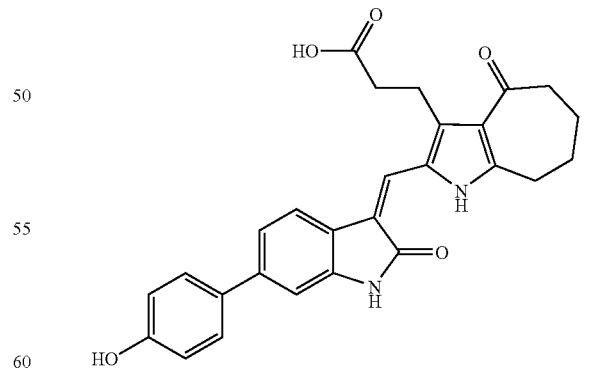

DCB-70151

(Z)-3-(2-((6-(4-hydroxyphenyl)-2-oxoindolin-3-ylidene)methyl)-4-oxo-1,4,5,6,7,8-hexahydrocyclohepta[b]pyrrol-3-yl)propanoic acid TABLE 1-continued

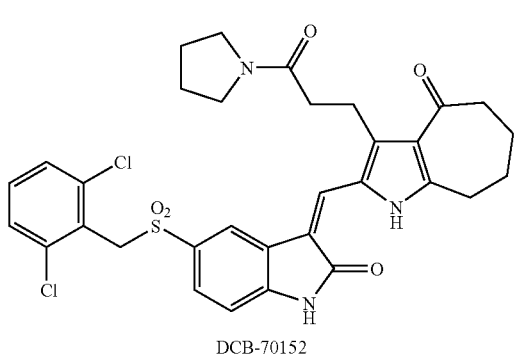

DCB-70152

(Z)-5-(2,6-dichlorobenzylsulfonyl)-3-((4-oxo-3-(3-oxo-
3-(pyrrolidin-1-yl)propyl)-4,5,6,7-tetrahydro-1H-indol-
2-yl)methylene)indolin-2-one

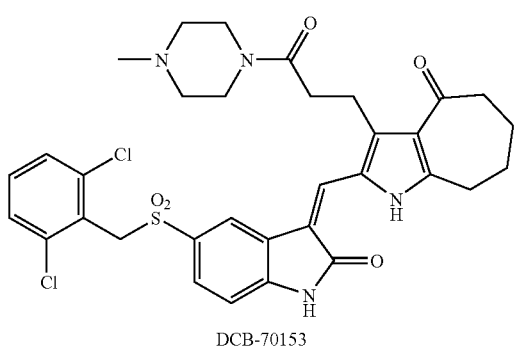

DCB-70153

(Z)-5-(2,6-dichlorobenzylsulfonyl)-3-((3-(3-(4-methylpiperazin-
1-yl)-3-oxopropyl)-4-oxo-4,5,6,7-tetrahydro-1H-indol-2-yl)
methylene)indolin-2-one

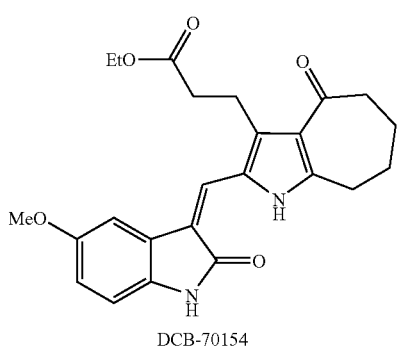

DCB-70154

(Z)-ethyl 3-(2-((5-methoxy-2-oxoindolin-3-ylidene)methyl)-4-
oxo-1,4,5,6,7,8-hexahydrocyclohepta[b]pyrrol-3-yl)propanoate TABLE 1-continued

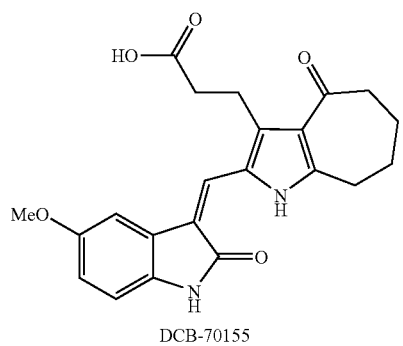

DCB-70155

(Z)-3-(2-((5-methoxy-2-oxoindolin-3-ylidene)methyl)-4-oxo-
1,4,5,6,7,8-hexahydrocyclohepta[b]pyrrol-3-yl)propanoic acid

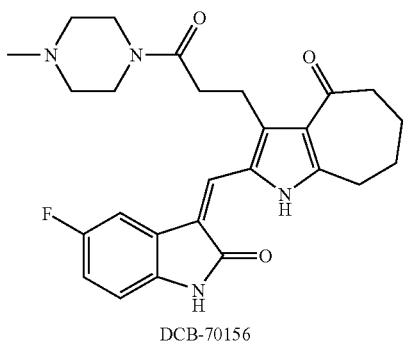

DCB-70156

(Z)-5-fluoro-3-((3-(3-(4-methylpiperazin-1-yl)-3-oxopropyl)-4-
oxo-4,5,6,7-tetrahydro-1H-indol-2-yl)methylene)indolin-2-one

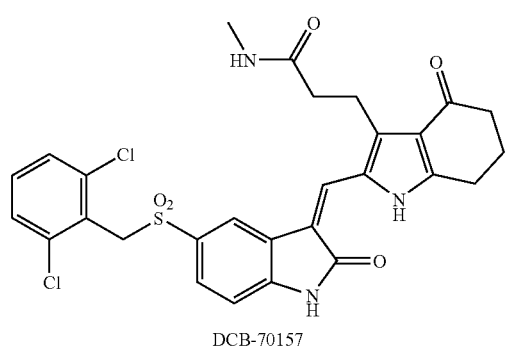

DCB-70157

(Z)-3-(2-((5-(2,6-dichlorobenzylsulfonyl)-2-oxoindolin-3-
ylidene)methyl)-4-oxo-4,5,6,7-tetrahydro-1H-indol-3-yl)-
N-methylpropanamide TABLE 1-continued

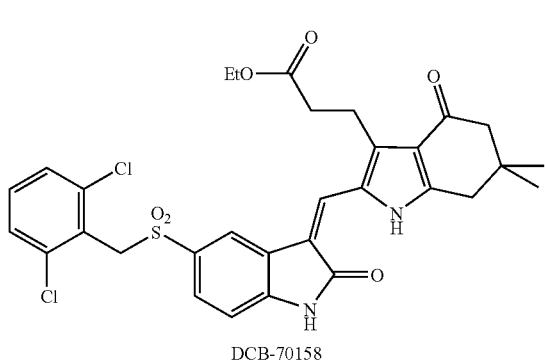

DCB-70158

(Z)-ethyl 3-(2-((5-(2,6-dichlorobenzylsulfonyl)-2-oxoindolin-
3-ylidene)methyl)-6,6-dimethyl-4-oxo-4,5,6,7-tetrahydro-1H-
indol-3-yl)propanoate

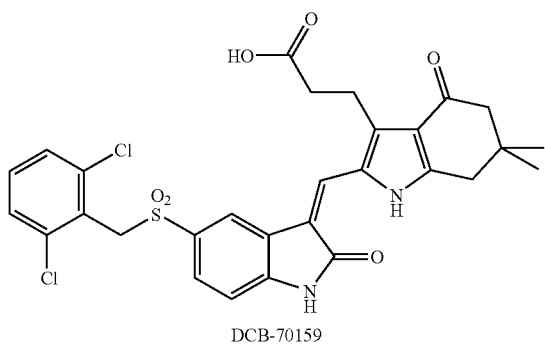

DCB-70159

(Z)-3-(2-((5-(2,6-dichlorobenzylsulfonyl)-2-oxoindolin-3-
ylidene)methyl)-6,6-dimethyl-4-oxo-4,5,6,7-tetrahydro-1H-
indol-3-yl)propanoic acid

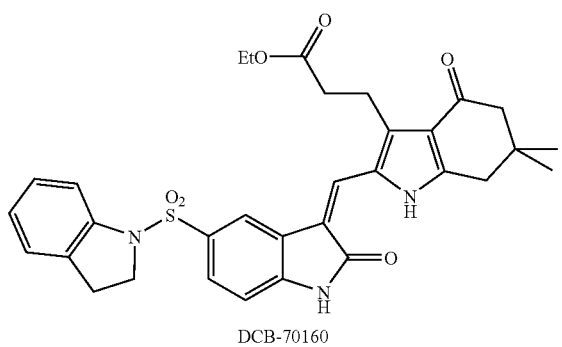

DCB-70160

(Z)-ethyl 3-(2-((5-(indolin-1-ylsulfonyl)-2-oxoindolin-3-ylidene)
methyl)-6,6-dimethyl-4-oxo-4,5,6,7-tetrahydro-1H-indol-3-yl)propanoate

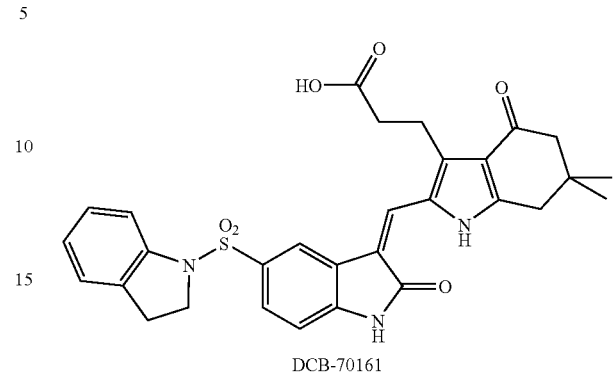

DCB-70161

(Z)-3-(2-((5-(indolin-1-ylsulfonyl)-2-oxoindolin-3-ylidene)
methyl)-6,6-dimethyl-4-oxo-4,5,6,7-tetrahydro-1H-indol-3-
yl)propanoic acid

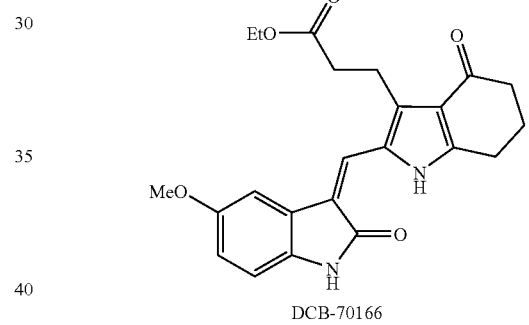

DCB-70166

(Z)-ethyl 3-(2-((5-methoxy-2-oxoindolin-3-ylidene)methyl)-
4-oxo-4,5,6,7-tetrahydro-1H-indol-3-yl)propanoate

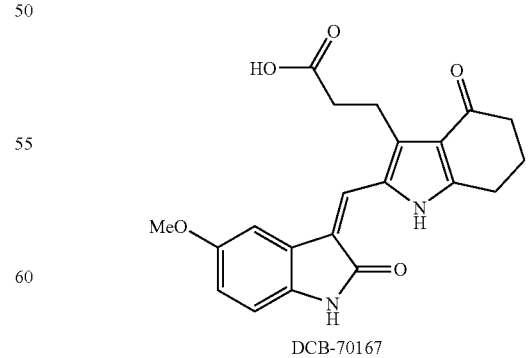

DCB-70167

(Z)-3-(2-((5-methoxy-2-oxoindolin-3-ylidene)methyl)-4-oxo-
4,5,6,7-tetrahydro-1H-indol-3-yl)propanoic acid TABLE 1-continued

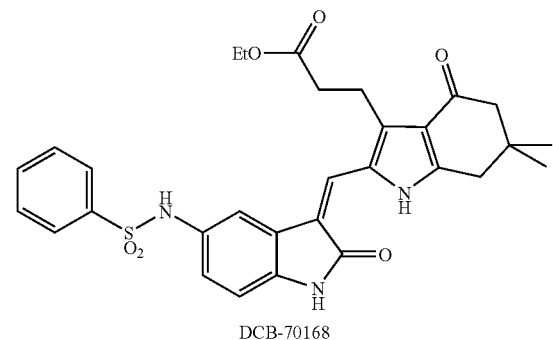

DCB-70168

(Z)-ethyl 3-(6,6-dimethyl-4-oxo-2-((2-oxo-5-(phenylsulfonamido)
indolin-3-ylidene)methyl)-4,5,6,7-tetrahydro-1H-indol-3-yl)propanoate

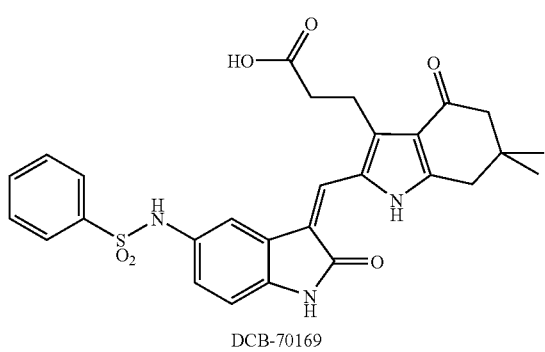

DCB-70169

(Z)-3-(6,6-dimethyl-4-oxo-2-((2-oxo-5-(phenylsulfonamido)
indolin-3-ylidene)methyl)-4,5,6,7-tetrahydro-1H-indol-3-
yl)propanoic acid

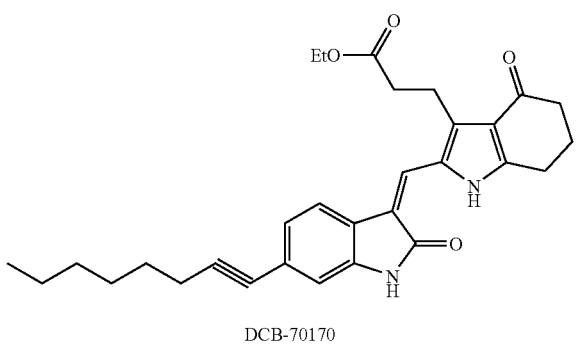

DCB-70170

(Z)-ethyl 3-(2-((6-(oct-1-ynyl)-2-oxoindolin-3-ylidene)
methyl)-4-oxo-4,5,6,7-tetrahydro-1H-indol-3-yl)propanoate TABLE 1-continued

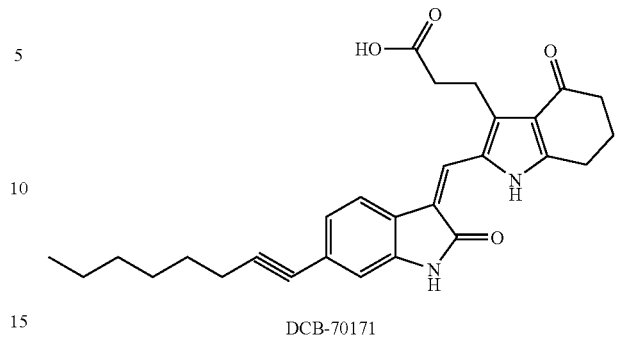

DCB-70171

(Z)-3-(2-((6-(oct-1-ynyl)-2-oxoindolin-3-ylidene)methyl)-4-
oxo-4,5,6,7-tetrahydro-1H-indol-3-yl)propanoic acid

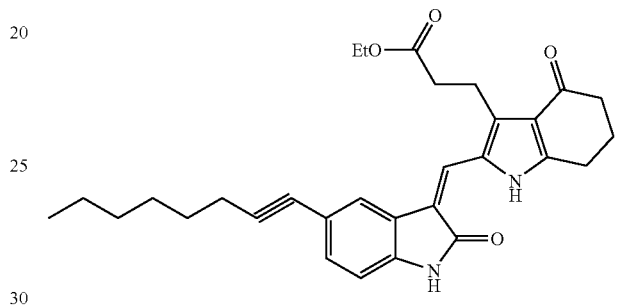

DCB-70172

(Z)-ethyl 3-(2-((5-(oct-1-ynyl)-2-oxoindolin-3-ylidene)methyl)-
4-oxo-4,5,6,7-tetrahydro-1H-indol-3-yl)propanoate

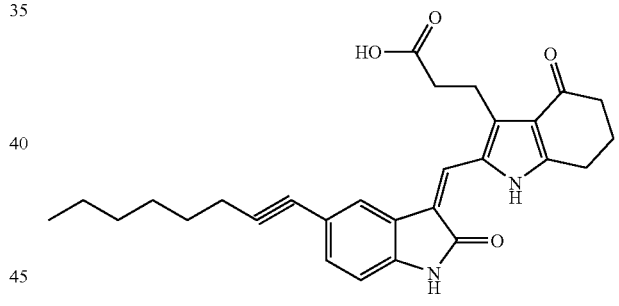

DCB-70173

(Z)-3-(2-((5-(oct-1-ynyl)-2-oxoindolin-3-ylidene)methyl)-4-
oxo-4,5,6,7-tetrahydro-1H-indol-3-yl)propanoic acid

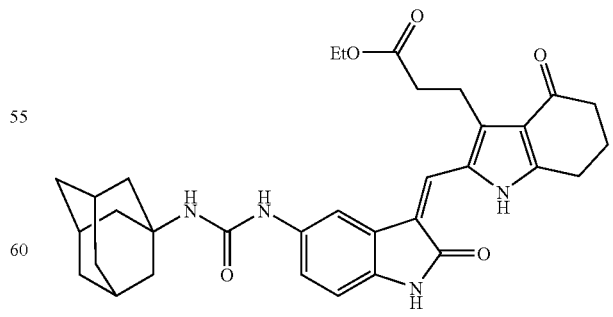

DCB-70174

Ethyl 3-(2-((Z)-(5-(3-(1-adamantanyl)ureido)-2-oxoindolin-3-
ylidene)methyl)-4-oxo-4,5,6,7-tetrahydro-1H-indol-3-yl)propanoate, TABLE 1-continued

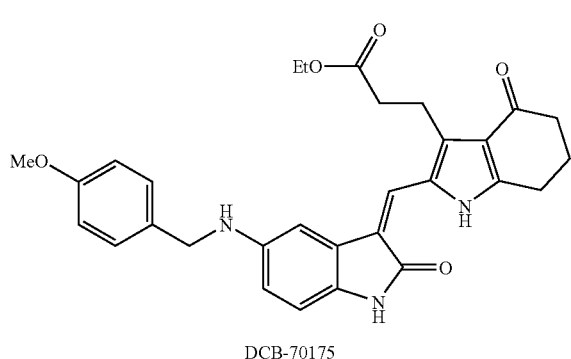

DCB-70175

(Z)-ethyl 3-(2-((5-(4-methoxybenzylamino)-2-oxoindolin-3-ylidene)
methyl)-4-oxo-4,5,6,7-tetrahydro-1H-indol-3-yl)propanoate

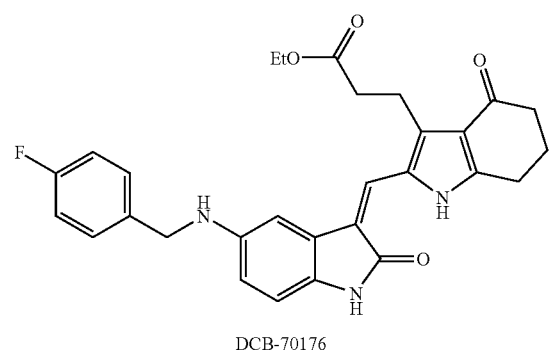

DCB-70176

(Z)-ethyl 3-(2-((5-(4-fluorobenzylamino)-2-oxoindolin-3-ylidene)
methyl)-4-oxo-4,5,6,7-tetrahydro-1H-indol-3-yl)propanoate

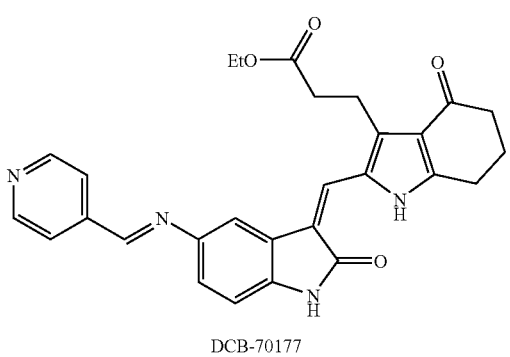

DCB-70177 ethyl 3-(4-oxo-2-((Z)-(2-oxo-5-((E)-pyridin-4-ylmethyleneamino)
indolin-3-ylidene)methyl)-4,5,6,7-tetrahydro-1H-indol-3-yl)propanoate

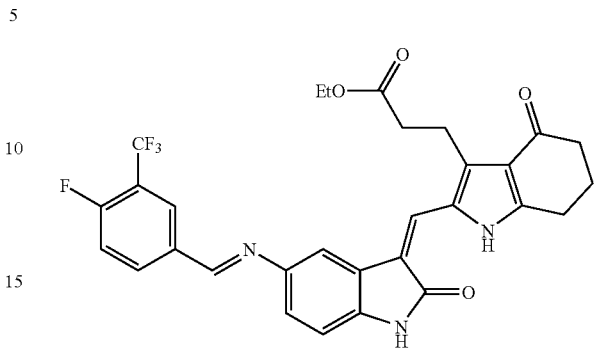

DCB-70178 ethyl 3-(2-((Z)-(5-((E)-4-fluoro-3-(trifluoromethyl)benzylideneamino)-
2-oxoindolin-3-ylidene)methyl)-4-oxo-4,5,6,7-tetrahydro-1H-
indol-3-yl)propanoate

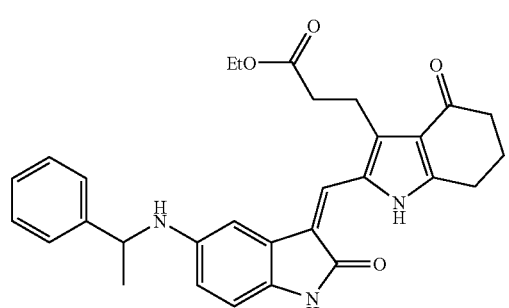

DCB-70179

(Z)-ethyl 3-(4-oxo-2-((2-oxo-5-(1-phenylethylamino)indolin-3-
ylidene)methyl)-4,5,6,7-tetrahydro-1H-indol-3-yl)propanoate

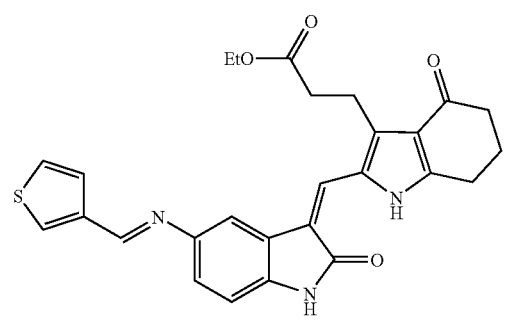

DCB-70180 ethyl 3-(4-oxo-2-((Z)-(2-oxo-5-((E)-thiophen-3-ylmethyleneamino)
indolin-3-ylidene)methyl)-4,5,6,7-tetrahydro-1H-indol-3-yl)propanoate TABLE 1-continued

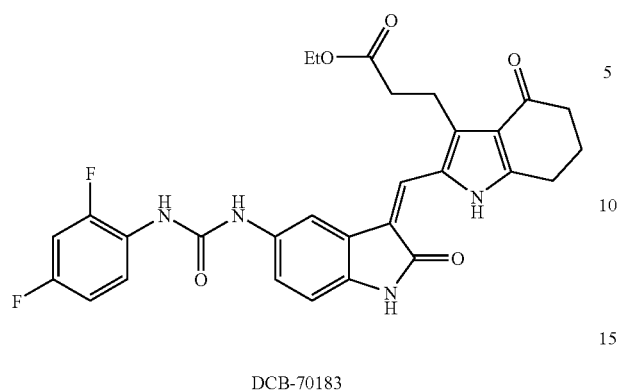

DCB-70183

(Z)-ethyl 3-(2-((5-(3-(2,4-difluorophenyl)ureido)-2-oxoindolin-3-ylidene)methyl)-4-oxo-4,5,6,7-tetrahydro-1H-indol-3-yl)propanoate

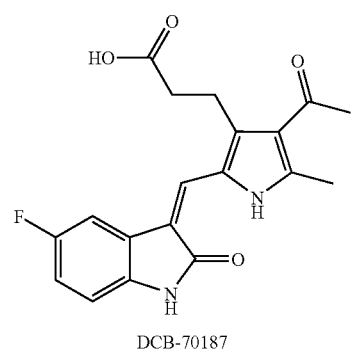

DCB-70187

(Z)-3-(4-acetyl-2-((5-fluoro-2-oxoindolin-3-ylidene)methyl)-5-methyl-1H-pyrrol-3-yl)propanoic acid

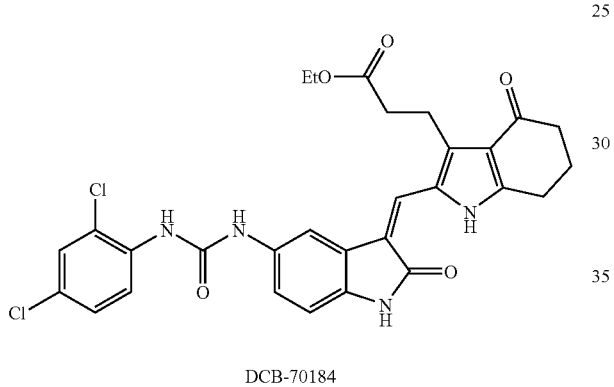

DCB-70184

(Z)-ethyl 3-(2-((5-(3-(2,4-dichlorophenyl)ureido)-2-oxoindolin-3-ylidene)methyl)-4-oxo-4,5,6,7-tetrahydro-1H-indol-3-yl)propanoate

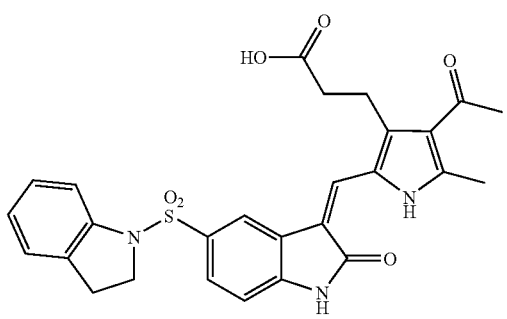

DCB-70188

(Z)-3-(4-acetyl-2-((5-(indolin-1-ylsulfonyl)-2-oxoindolin-3-ylidene)methyl)-5-methyl-1H-pyrrol-3-yl)propanoic acid

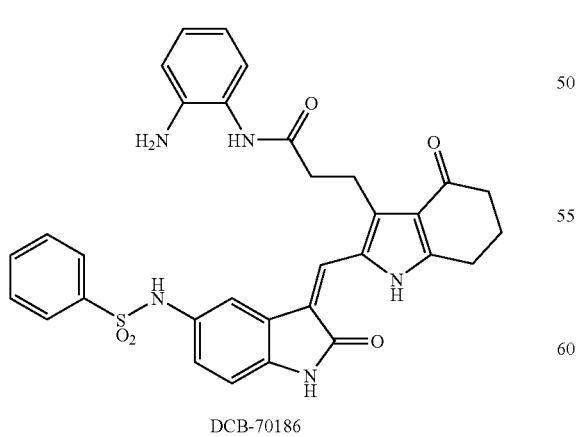

DCB-70186

(Z)-N-(2-aminophenyl)-3-(4-oxo-2-((2-oxo-5-(phenylsulfonamido)indolin-3-ylidene)methyl)-4,5,6,7-tetrahydro-1H-indol-3-yl)propanamide

DCB-70189

(Z)-ethyl 3-(2-((5-(3,5-difluorophenylsulfonamido)-2-oxoindolin-3-ylidene)methyl)-4-oxo-4,5,6,7-tetrahydro-1H-indol-3-yl)propanoate TABLE 1-continued

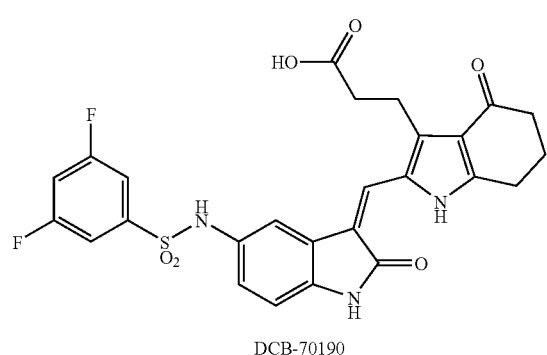

DCB-70190

(Z)-3-(2-((5-(3,5-difluorophenylsulfonamido)-2-oxoindolin-3-ylidene)methyl)-4-oxo-4,5,6,7-tetrahydro-1H-indol-3-yl)propanoic acid

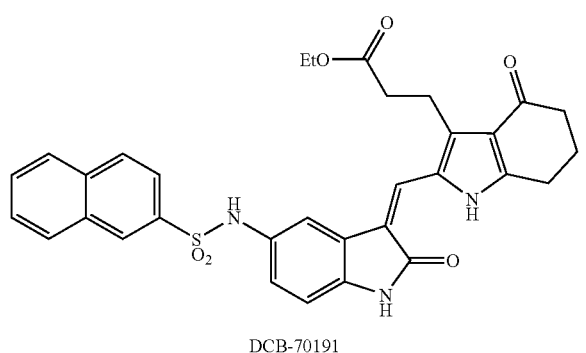

DCB-70191

(Z)-ethyl 3-(2-((5-(naphthalene-2-sulfonamido)-2-oxoindolin-3-ylidene)methyl)-4-oxo-4,5,6,7-tetrahydro-1H-indol-3-yl)propanoate

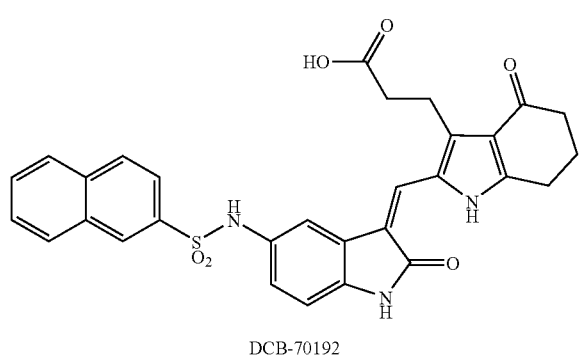

DCB-70192

(Z)-3-(2-((5-(naphthalene-2-sulfonamido)-2-oxoindolin-3-ylidene)methyl)-4-oxo-4,5,6,7-tetrahydro-1H-indol-3-yl)propanoic acid

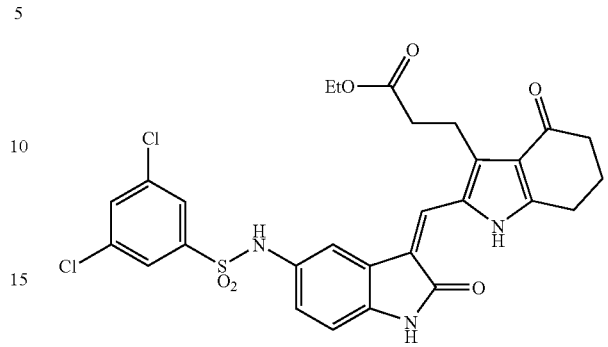

DCB-70193

(Z)-ethyl 3-(2-((5-(3,5-dichlorophenylsulfonamido)-2-oxoindolin-3-ylidene)methyl)-4-oxo-4,5,6,7-tetrahydro-1H-indol-3-yl)propanoate

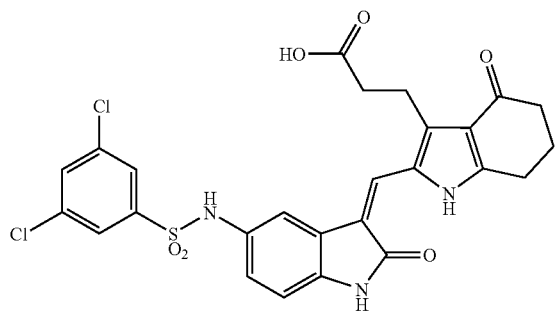

DCB-70194

(Z)-3-(2-((5-(3,5-dichlorophenylsulfonamido)-2-oxoindolin-3-ylidene)methyl)-4-oxo-4,5,6,7-tetrahydro-1H-indol-3-yl)propanoic acid

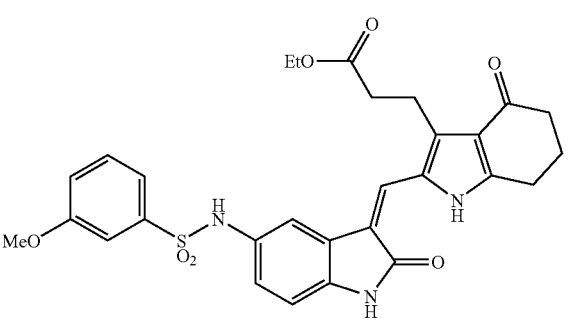

DCB-70195

(Z)-ethyl 3-(2-((5-(3-methoxyphenylsulfonamido)-2-oxoindolin-3-ylidene)methyl)-4-oxo-4,5,6,7-tetrahydro-1H-indol-3-yl)propanoate TABLE 1-continued

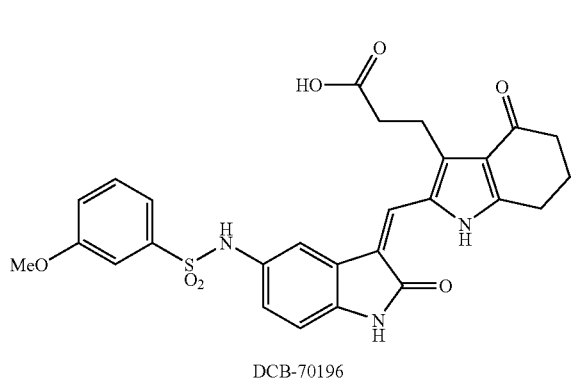

DCB-70196

(Z)-3-(2-((5-(3-methoxyphenylsulfonamido)-2-oxoindolin-3-ylidene)
methyl)-4-oxo-4,5,6,7-tetrahydro-1H-indol-3-yl)propanoic acid

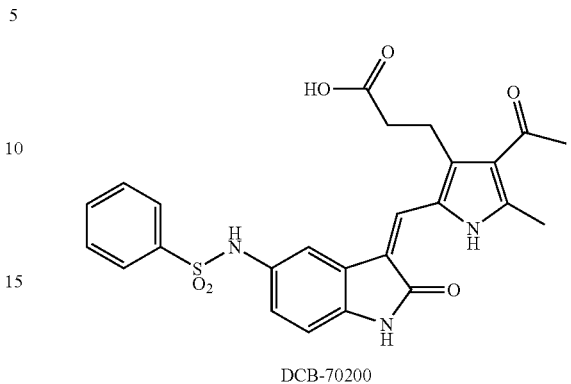

DCB-70200

(Z)-3-(4-acetyl-5-methyl-2-((2-oxo-5-(phenylsulfonamido)indolin-
3-ylidene)methyl)-1H-pyrrol-3-yl)propanoic acid

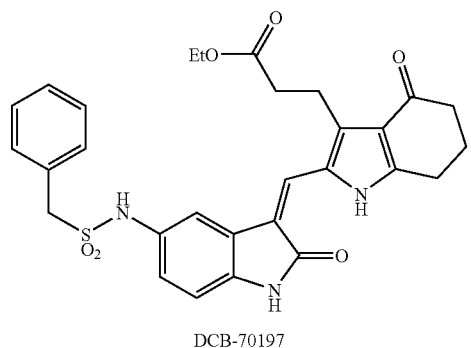

DCB-70197

(Z)-ethyl 3-(4-oxo-2-((2-oxo-5-(phenylmethylsulfonamido)indolin-3-
ylidene)methyl)-4,5,6,7-tetrahydro-1H-indol-3-yl)propanoate

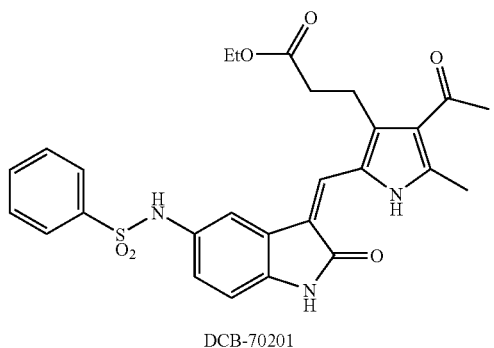

DCB-70201

(Z)-ethyl 3-(4-acetyl-5-methyl-2-((2-oxo-5-(phenylsulfonamido)
indolin-3-ylidene)methyl)-1H-pyrrol-3-yl)propanoate

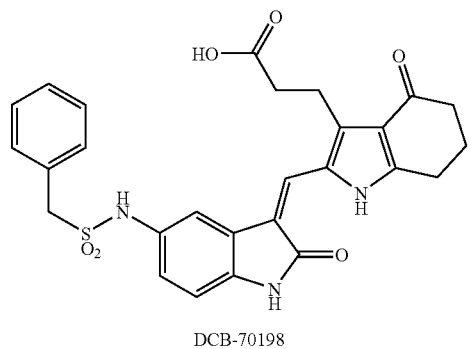

DCB-70198

(Z)-3-(4-oxo-2-((2-oxo-5-(phenylmethylsulfonamido)indolin-3-
ylidene)methyl)-4,5,6,7-tetrahydro-1H-indol-3-yl)propanoic acid

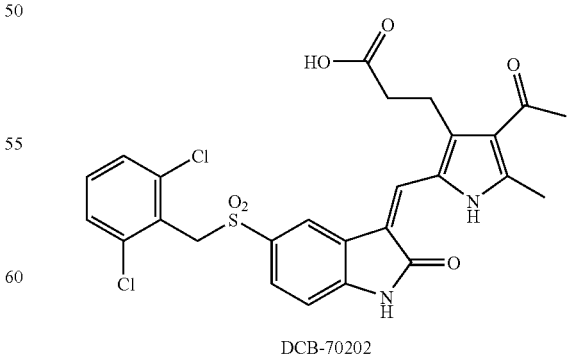

DCB-70202

(Z)-3-(4-acetyl-2-((5-(2,6-dichlorobenzylsulfonyl)-2-oxoindolin-
3-ylidene)methyl)-5-methyl-1H-pyrrol-3-yl)propanoic acid TABLE 1-continued

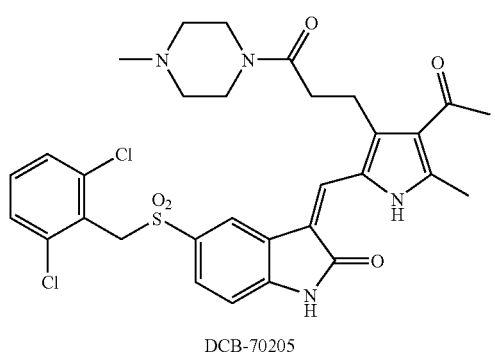

DCB-70205

(Z)-3-((4-acetyl-5-methyl-3-(3-(4-methylpiperazin-1-yl)-3-
oxopropyl)-1H-pyrrol-2-yl)methylene)-5-(2,6-dichlorobenzylsulfonyl)
indolin-2-one

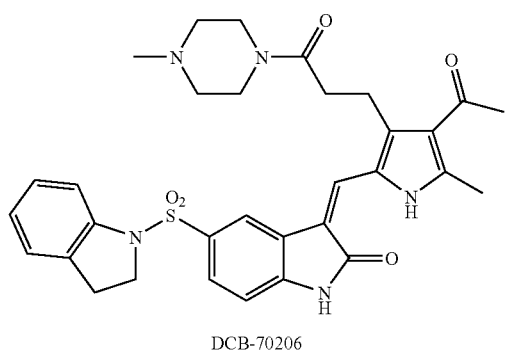

DCB-70206

(Z)-3-((4-acetyl-5-methyl-3-(3-(4-methylpiperazin-1-yl)-3-oxopropyl)-
1H-pyrrol-2-yl)methylene)-5-(indolin-1-ylsulfonyl)indolin-2-one

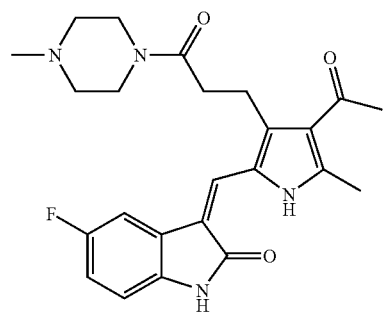

DCB-70207

(Z)-3-((4-acetyl-5-methyl-3-(3-(4-methylpiperazin-1-yl)-3-oxopropyl)-
1H-pyrrol-2-yl)methylene)-5-fluoroindolin-2-one TABLE 1-continued

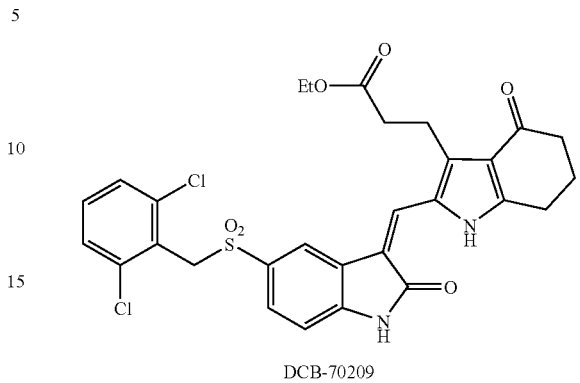

DCB-70209

(Z)-ethyl 3-(2-((5-(2,6-dichlorobenzylsulfonyl)-2-oxoindolin-3-
ylidene)methyl)-4-oxo-4,5,6,7-tetrahydro-1H-indol-3-yl)propanoate

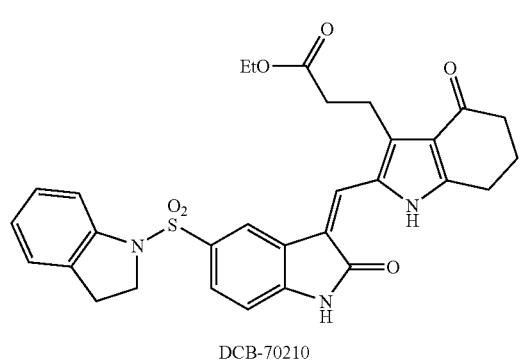

DCB-70210

(Z)-ethyl 3-(2-((5-(indolin-1-ylsulfonyl)-2-oxoindolin-3-ylidene)
methyl)-4-oxo-4,5,6,7-tetrahydro-1H-indol-3-yl)propanoate

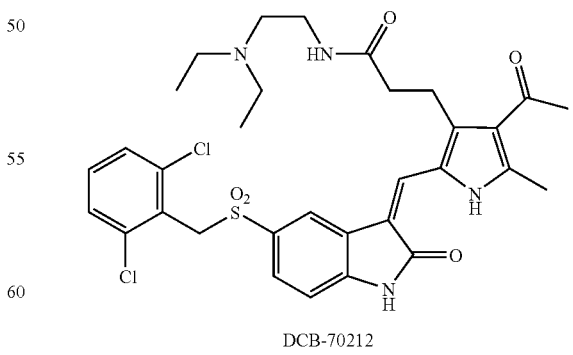

DCB-70212

(Z)-3-(4-acetyl-2-((5 -(2,6-dichlorobenzylsulfonyl)-2-oxoindolin-3-
ylidene)methyl)-5-methyl-1H-pyrrol-3-yl)-N-(2-(diethylamino)
ethyl)propanamide TABLE 1-continued

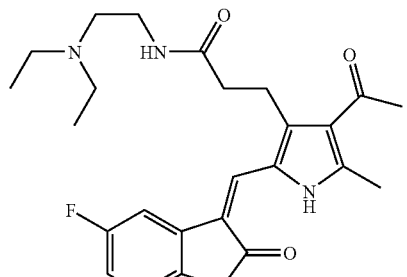

DCB-70213

(Z)-3-(4-acetyl-2-((5-fluoro-2-oxoindolin-3-ylidene)methyl)-5-methyl-1H-pyrrol-3-yl)-N-(2-(diethylamino)ethyl)propanamide

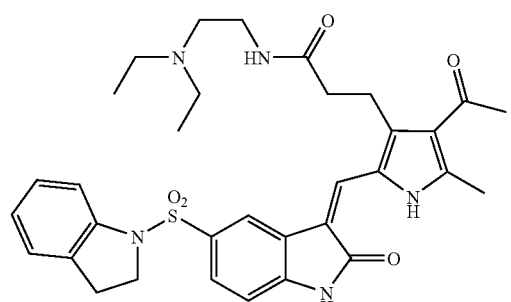

DCB-70214

(Z)-3-(4-acetyl-2-((5-(indolin-1-ylsulfonyl)-2-oxoindolin-3-ylidene)methyl)-5-methyl-1H-pyrrol-3-yl)-N-(2-(diethylamino)ethyl)propanamide

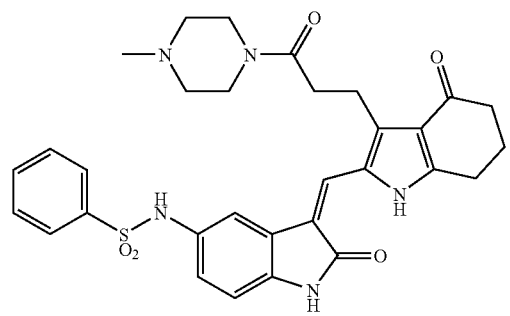

DCB-70218

(Z)-N-(3-((3-(3-(4-methylpiperazin-1-yl)-3-oxopropyl)-4-oxo-4,5,6,7-tetrahydro-1H-indol-2-yl)methylene)-2-oxoindolin-5-yl)benzenesulfonamide

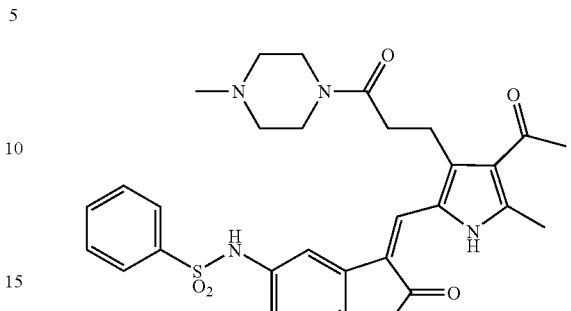

DCB-70219

(Z)-N-(3-((4-acetyl-5-methyl-3-(3-(4-methylpiperazin-1-yl)-3-oxopropyl)-1H-pyrrol-2-yl)methylene)-2-oxoindolin-5-yl)benzenesulfonamide

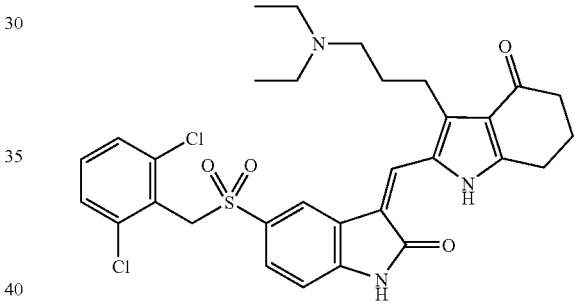

DCB-70222

(Z)-5-(2,6-dichlorobenzylsulfonyl)-3-((3-(3-(diethylamino)propyl)-4-oxo-4,5,6,7-tetrahydro-1H-indol-2-yl)methylene)indolin-2-one

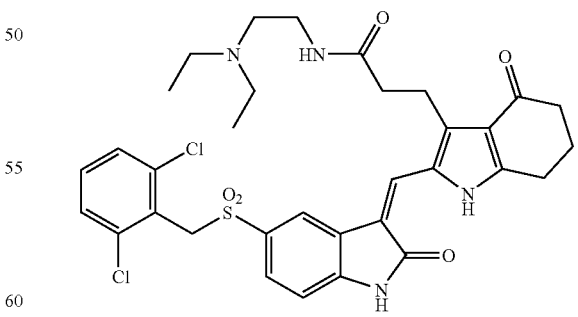

DCB-70223

(Z)-3-(2-((5-(2,6-dichlorobenzylsulfonyl)-2-oxoindolin-3-ylidene)methyl)-4-oxo-4,5,6,7-tetrahydro-1H-indol-3-yl)-N-(2-(diethylamino)ethyl)propanamide TABLE 1-continued

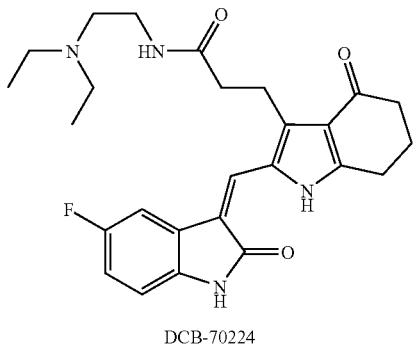

DCB-70224

(Z)-N-(2-(diethylamino)ethyl)-3-(2-((5-fluoro-2-oxoindolin-3-ylidene)methyl)-4-oxo-4,5,6,7-tetrahydro-1H-indol-3-yl)propanamide

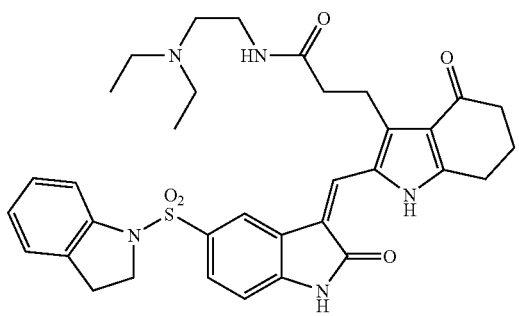

DCB-70225

(Z)-N-(2-(diethylamino)ethyl)-3-(2-((5-(indolin-1-ylsulfonyl)-2-oxoindolin-3-ylidene)methyl)-4-oxo-4,5,6,7-tetrahydro-1H-indol-3-yl)propanamide

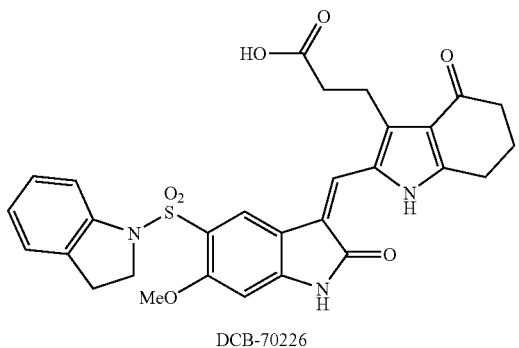

DCB-70226

(Z)-3-(2-((5-(indolin-1-ylsulfonyl)-6-methoxy-2-oxoindolin-3-ylidene)methyl)-4-oxo-4,5,6,7-tetrahydro-1H-indol-3-yl)propanoic acid The indolinone compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The route shown in Scheme 1 below exemplifies synthesis of the indolinone compounds of the present invention. A reaction mixture of 1,3-cyclohexanedione (1), 5-aminolevulinic acid hydrochloride (2), sodium acetate, and $H_2O$ is heated at 100° C. for 16 h to give 3-carboxyethyl-4-oxo-4,5,6,7-tetrahydro-1H-indole (3). A solution of 3 in ethanol (100 mL) is added with sulfuric acid. The resulting reaction mixture is refluxed for 12 h to provide 3-(3-ethoxy-3-oxopropyl)-4-oxo-4,5,6,7-tetrahydro-1H-indole (4) as yellow solids. Trimethylorthoformate is then added to a solution (47 mL) containing 4 in trifluoroacetic acid at 0° C. The reaction mixture thus formed is stirred at 0° C. for 30 min, warmed up to room temperature, and stirred for 2.0 h. The mixture is then added with ethyl acetate, water, and NaOH. The organic layer is collected, washed with saturated aqueous $NaHCO_3$, dried over $MgSO_4$ (s), and concentrated under reduced pressure. The oily residue is purified to give 3-(3-ethoxy-3-oxopropyl)-2-formyl-4-oxo-4,5,6,7-tetrahydro-1H-indole (5) as yellow solids. Next, a mixture of 5 and an indolin-2-one (6) is added into EtOH and piperidine. The resulting solution is refluxed for 12 h. The resultant precipitate is filtered and washed with EtOH to provide the corresponding (Z)-3-((3-(3-ethoxy-3-oxopropyl)-4-oxo-4,5,6,7-tetrahydro-1H-indol-2-yl)methylene)indolin-2-one (7). To obtain the corresponding carboxylic acid (8), 3.0 N aqueous NaOH is added into a solution of 7 in EtOH; the resulting mixture is refluxed for 2 h and cooled to room temperature; the solution is then acidified with 6 N HCl to pH 3.0; and the resultant precipitate is filtered and washed with MeOH. To afford the corresponding sodium salt (9), a mixture of aqueous NaOH, MeOH, and 8 can be stirred and heated to boiling; 2-propanol can then be slowly added to the mixture; and the solution can be stirred for 12 h.

Scheme 1

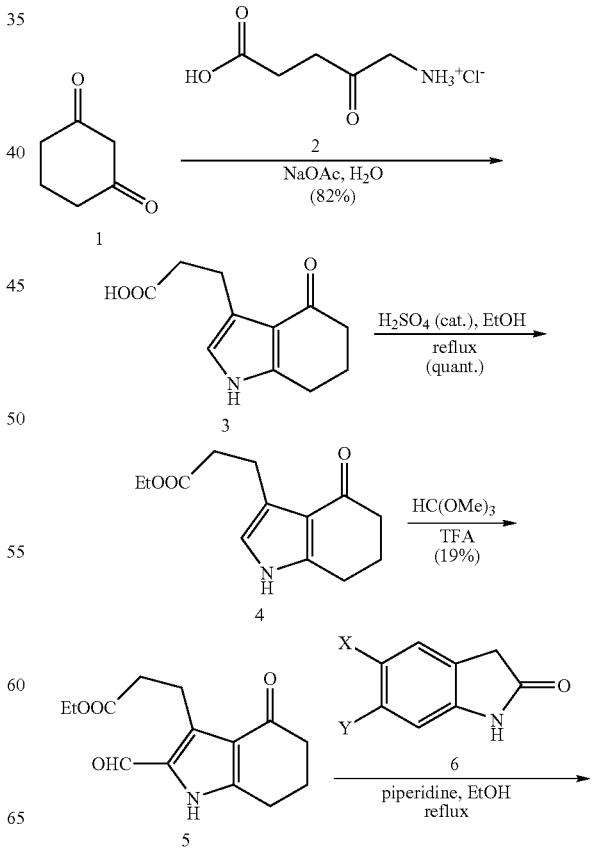

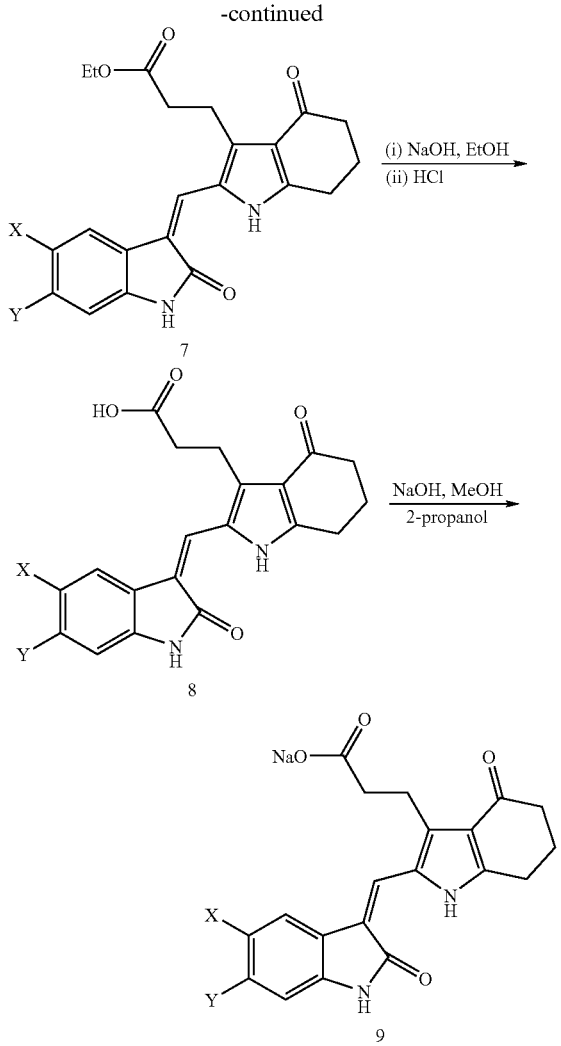

An indolinone compound thus synthesized can be further purified by flash column chromatography, high performance liquid chromatography, crystallization, or any other suitable methods.

The indolinone compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of at least one of the indolinone compounds of this invention and a pharmaceutically acceptable carrier, (2) a method for treating a protein kinase-related disease (e.g., cancer) by administering to a subject in need of this treatment an effective amount of such an indolinone compound, and (3) a method of decreasing the activity of at least one protein kinase by contacting the at least one protein kinase with at least one of the indolinone compounds of this invention.

As used herein, the term "protein kinase-related disease" refers to a disease or condition that is characterized by abnormal PK activity or a disease or condition that can be treated with changes to the activity of at least one PK. Abnormal PK activity can arise as the result of elevated PK expression level, or presence of PK expression that does not happen in normal conditions. PK-related disease describe herein include, but not limited to, cancer, diabetes, a hyper-proliferation disorder, hyperproliferative disorders of the kidney, renal disease, von Hippel-Lindau disease, restenosis, fibrosis, psoriasis, osteoarthritis, rheumatoid arthritis, an inflammatory disorder, immunological disorders such as autoimmune diseases (e.g., AIDS, lupus, etc.), cardiovascular disorders (e.g. atherosclerosis), and blood vessel proliferative disorders such as abnormal vasculogenesis.

The term "treating" refers to administering an indolinone compound to a subject that has a protein kinase-related disease, or has a symptom of or a predisposition toward it, with the purpose to cure, heal, alleviate, relieve, alter, remedy, ameliorate, improve, affect or reduce the risk of the disorder, the symptoms of or the predisposition toward the disorder. For example, treating cancer refers to the treatment results in inhibition of cancer growth or cancer cell growth, regression in cancer growth (i.e. it reduces the size of a detectable cancer), or the disappearance of a cancer. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents. The subject in need of the treatment can be a mammal. The term "mammal" refers to human or nonhuman mammal, for example, dogs, cats, pigs, cows, sheep, goats, horses, rats, or mice.

Cancer that can be treated by the methods of the invention is any abnormal cell or tissue growth, for example, a tumor, whether malignant, pre-malignant, or non-malignant. It is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type. The term cancer includes, as non-limiting examples, lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, and leukemia. It also includes drug resistant cancer (including but not limited to multidrug resistant cancer).

The compounds described herein can be administered to a mammal in conjunction with radiation therapy, immunotherapy, monoclonal antibody therapy, hormonal therapy, chemotherapy using other agents, and/or surgery. By in conjunction with, the therapies do not need to occur at the same time, but can be in succession, or alternating with each other and/or periods of rest and recovery.

In one embodiment, a protein kinase-related disease, such as cancer, is treated with a method comprising administering effective amount of at least one indolinone compound of this invention and at least one chemotherapeutic agent to a mammal. Nonlimiting examples of chemotherapeutic agent include, PK inhibitors other than the compound described herein (e.g., imatinib mesylate, gefitinib, dasatinib, erlotinib, lapatinib, sunitinib, nilotinib, and sorafenib; antibodies, including, e.g., trastuzumab, rituximab, cetuximab, and bevacizumab; mitoxantrone; dexamethasone; prednisone; and temozolomide), alkylating agents (e.g., melphalan, chlorambucil, busulfan, thiotepa, ifosfamide, carmustine, lomustine, semustine, streptozocin, decarbazine, and cyclophosphamide), mitotic inhibitors, antimetabolites (e.g., capecitibine, gemcitabine, 5-fluorouracil or 5-fluorouracil/leucovorin, fludarabine, cytarabine, mercaptopurine, thioguanine, pentostatin, and methotrexate), cell cycle inhibitors, enzymes, hormones, anti-hormones, growth-factor inhibitors, plant alkaloids and terpenoids, topoisomerase inhibitors (e.g., etoposide, teniposide, camptothecin, topotecan, irinotecan, doxorubicin, and daunorubicin), antitumor antibiotics (e.g., actinomycin D, bleomycin, mitomycin C, adriamycin, daunorubicin, idarubicin, doxorubicin and pegylated liposomal doxorubicin), vinca alkaloids (e.g., vincristine and vinblastin), taxanes (e.g., paclitaxel and docetaxel), platinum agents (e.g., cisplatin, carboplatin, and oxaliplatin), thalidomide and related analogs (e.g., CC-5013 and CC-4047), monoclonal antibodies, and antiangiogenic agents.

As used herein, the term "contacting" means brining a compound of this invention and at least one PK together in a way that the compound can decrease the activity of the at least one PK, either directly, i.e., by acting on the protein kinase itself, or indirectly, i.e., by acting on another molecule on which the activity of the at least one PK is dependent. "Contacting" can occur in vitro or in vivo. For instance, in a test tube that contains the at least one PK; in a culture dish that has whole cells grown; or in a mammal to which the compound of this invention is administered. Examples of target PK include, but are not limited to Aurora A & B kinase, MAP, CDK2, Raf, NEK (including NEK 4a, NEK 4b, NEK 5 and NEK 6), BUB1, VEGFR, C-MET, HER2, HER3, HER4, IR, IGF-IR, IRR, PDGFRct, PDGFRO, CSFIR, C-Kit, C-fms, Flk-1R, F1k4, KDR1F1k-1, FLT-1, FLT3, FGFR-1, FGFR-2, FGFR-3, FGFR4, Src, Frk, Btk, Csk, Abl, ZAP70, Fes, Fps, Fak, Jak, Ack, Yes, Fyn, Lyn, Lck, Blk, Hck, Fgr, Aur2, and Yrk.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In one embodiment, an indolinone compound of this invention is administered intravenously, suitable carriers may include but not limited to, physiological saline or phosphate buffered saline (PBS), and solutions containing thickening and solubilizing agents, such as glucose, polyethylene glycol, and polypropylene glycol and mixtures thereof.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An indolinone compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the active indolinone compounds can be utilized as pharmaceutical carriers for delivery of the active compounds. Examples of other carriers include colloidal silicon dioxide, magnesium stearate, sodium lauryl sulfate, and D&C Yellow # 10.

Suitable in vitro assays can be used to preliminarily evaluate the efficacy of the indolinone compounds of this invention in anticancer activities such as inhibiting growth of tumor cells. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Syntheses of (Z)-3-((3-(3-ethoxy-3-oxopropyl)-4-oxo-4,5,6,7-tetrahydro-1H-indol-2-yl)methylene)indolin-2-one (DCB-70049) and (Z)-3-((3-carboxyethyl-4-oxo-4,5,6,7-tetrahydro-1H-indol-2-yl)methylene)indolin-2-one (DCB-70052)

Unless stated otherwise, the compound numerals are made reference to Scheme 1 above.

3-Carboxyethyl-4-oxo-4,5,6,7-tetrahydro-1H-indole (3): A mixture of 5-aminolevulinic acid hydrochloride (2, 50.0 g, 0.298 mol), 1,3-cyclohexanedione (1, 40.2 g, 0.359 mol), and sodium acetate (48.8 g, 0.595 mol) was added with $H_2O$ (125 mL). The reaction mixture was heated at 100° C. for 16 h. The solution was cooled to room temperature and the resultant precipitate was filtered, washed with water (200 mL×2), and air-dried to give 3-carboxyethyl-4-oxo-4,5,6,7-tetrahydro-1H-indole (3, 50.5 g, 0.245 mol) as yellow solids in 82% yield.

3-(3-Ethoxy-3-oxopropyl)-4-oxo-4,5,6,7-tetrahydro-1H-indole (4): 3-Carboxyethyl-4-oxo-4,5,6,7-tetrahydro-1H-indole (3, 52.0 g, 0.251 mol) in ethanol (100 mL) was added with sulfuric acid (1.0 mL). The reaction mixture was heated at reflux for 12 h. The solution was concentrated under reduced pressure and the resultant solids were washed with water (200 mL×2). The solids were air-dried to give 3-(3-ethoxy-3-oxopropyl)-4-oxo-4,5,6,7-tetrahydro-1H-indole (4, 59.0 g, 0.251 mol) as yellow solids in >99% yield.

3-(3-Ethoxy-3-oxopropyl)-2-formyl-4-oxo-4,5,6,7-tetrahydro-1H-indole (5): To a trifluoroacetic acid solution (47 mL) containing 3-(3-ethoxy-3-oxopropyl)-4-oxo-4,5,6,7-tetrahydro-1H-indole (4, 10.0 g, 42.5 mmol) was added with trimethylorthoformate (13.6 g, 128 mmol) at 0° C. The reaction was stirred at 0° C. for 30 min, warmed up to room temperature and stirred for 2.0 h. The solution was added with ethyl acetate (250 mL), water (200 mL) and NaOH (18 g). The organic layer was collected and washed with saturated aqueous $NaHCO_3$ (200 mL), dried over $MgSO_4$ (s), and concentrated under reduced pressure. The oily residue was purified by gravity column chromatography (50% EtOAc in hexanes) to give 3-(3-ethoxy-3-oxopropyl)-2-formyl-4-oxo-4,5,6,7-tetrahydro-1H-indole (5, 2.1 g, 8.0 mmol) as yellow solids in 19% yield.

(Z)-3-((3-(3-ethoxy-3-oxopropyl)-4-oxo-4,5,6,7-tetrahydro-1H-indol-2-yl)methylene)indolin-2-one (DCB-70049): A mixture of compound 5 (0.50 mmol) and indolin-2-one (0.50 mmol) was added with EtOH (5.0 mL) and piperidine (0.1 mL). The reaction was heated at reflux for 12 h. The resultant precipitate was filtered and washed with EtOH to provide the diresed product. $^1$H NMR ($CDCl_3$) δ 7.93 (s, 1 H), 7.61 (s, 1 H), 7.59 (d, 1 H, ArH), 7.19 (dd, 1 H), 7.09 (dd, 1 H), 6.89 (d, 1 H), 4.07 (q, 2 H), 3.27 (t, 2 H), 2.91 (t, 2 H), 2.74 (t, 2 H), 2.52 (t, 2 H), 2.14-2.19 (m, 2 H), 1.18 (t, 3 H).

(Z)-3-((3-carboxyethyl-4-oxo-4,5,6,7-tetrahydro-1H-indol-2-yl)methylene)indolin-2-one (DCB-70052): To an EtOH solution (3.0 mL) containing (Z)-3-((3-(3-ethoxy-3-oxopropyl)-4-oxo-4,5,6,7-tetrahydro-1H-indol-2-yl)methylene)indolin-2-one (0.50 mmol) was added 3.0 N aqueous NaOH (1.0 mL). The reaction was heated at reflux for 2.0 h and cooled to room temperature. The solution was acidified with 6 N HCl to pH 3.0. The resultant precipitate was filtered and washed with MeOH to provide the desired product. $^1$H NMR (DMSO-$d_6$) δ 13.76 (s, 1 H), 11.01 (s, 1 H), 7.77 (s, 1 H), 7.76 (d, 1 H), 7.17 (dd, 1 H), 7.01 (dd, 1 H), 6.89 (dd, 1 H), 3.15 (t, 2 H), 2.91 (t, 2H), 2.36-2.41 (m, 2 H), 2.06 (t, 2 H).

Example 2

Syntheses of Other Compounds Listed in Table 1

Other indolinone compounds listed in Table 1 above were synthesized in a manner similar to that describe in Example 1. Their spectroscopy data are provided below.

DCB-70053: $^1$H NMR ($CDCl_3$) δ 7.73 (s, 1 H), 7.59 (s, 1 H), 7.30 (dd, ArH), 6.89 (m, 1 H), 6.81 (dd, 1 H), 4.07 (q, 2 H), 3.27 (t, 2 H), 2.92 (t, 2 H), 2.74 (t, 2 H), 2.52 (t, 2 H), 2.15-2.20 (m, 2 H), 1.19 (t, 3 H).

DCB-70055: $^1$H NMR ($d^6$-DMSO) δ 13.79 (s, 1 H), 11.01 (s, 1 H), 7.83 (s, 1 H), 7.75 (dd, 1 H), 6.95-6.99 (m, 1 H), (dd, 1 H), 3.17 (t, 2 H), 2.91 (t, 2 H), 2.40-2.47 (m, 2 H), 2.07 (t, 2 H).

DCB-70056: $^1$H NMR ($d^6$-DMSO) δ 13.74 (s, 1 H), 11.11 (s, 1 H), 8.10 (d, 1 H), 7.83 (s, 1 H), 7.30 (dd, 1 H), 6.83 (d, 1 H), 4.01 (q, 2 H), 3.23 (t, 2 H), 2.91 (t, 2 H), 2.57 (t, 2 H), 2.40 (t, 2 H), 2.04-2.09 (m, 2 H), 1.14 (t, 3 H).

DCB-70057: $^1$H NMR ($d^6$-DMSO) δ 13.74 (s, 1 H), 11.12 (s, 1 H), 8.08 (d, 1 H), 7.88 (s, 1 H), 7.31 (dd, 1 H), 6.84 (d, 1 H), 3.19 (t, 2 H), 2.92 (t, 2 H), 2.36-2.42 (m, 2 H), 2.07 (t, 2 H).

DCB-70058: $^1$H NMR (DMSO-$d_6$) δ 13.84 (s, 1 H), 11.04 (s, 1 H), 9.02 (s, 1 H), 8.04 (s, 1 H), 7.86 (s, 1 H), 7.41 (d, 1 H), 7.20 (d, 1 H), 7.10 (dd, 1 H), 6.93 (d, 1 H), 6.85 (d, 1 H), 3.98 (q, 2 H), 3.87 (s, 1 H), 3.24 (t, 2 H), 2.92 (t, 2 H), 2.61 (t, 2 H), 2.41 (t, 2 H), 2.00-2.09 (m, 2 H), 1.10 (t, 3 H).

DCB-70059: $^1$H NMR (DMSO-$d_6$) δ 13.73 (s, 1 H, NH), 8.08 (s, 1 H, OH), 8.02 (s, 1 H, ArH), 7.38 (d, J=8.1 Hz, 1 H, ArH), 7.22 (d, 1 H), 7.20 (d, 1 H), 7.09 (m, 1 H), 6.90 (m, 1 H), 6.84 (m, 1 H), 3.86 (s, 3 H), 3.16 (m, 2 H), 2.89 (m, 2 H), 2.38 (m, 2 H), 2.16 (m, 2 H), 2.06 (m, 2 H).

DCB-70062: $^1$H NMR (DMSO-$d_6$) δ 13.61 (s, 1 H), 8.84 (s, 1 H), 8.11 (m, 2 H), 7.06 (d, 1 H), 4.02 (q, 2 H), 3.27 (m, 2 H), 2.94 (m, 2 H), 2.60 (m, 2 H), 2.41 (m, 2 H), 2.06 (m, 2 H), 1.14 (t, 3 H).

DCB-70063: $^1$H NMR (DMSO-$d_6$) δ 13.52 (s, 1 H), 11.57 (s, 1 H), 8.73 (d, 1 H), 8.02-8.05 (m, 2H), 6.99 (d, 1 H), 3.18 (m, 2 H), 2.89 (m, 2 H), 2.48 (m, 2 H), 2.39 (m, 2 H), 2.05 (m, 2 H).

DCB-70064: $^1$H NMR (DMSO-$d_6$) δ 13.72 (s, 1 H), 11.42 (s, 1 H), 8.23 (d, 1 H), 7.91 (s, 1 H), 7.59 (dd, 1 H), 7.25 (dd, 1 H), 7.07 (d, 1 H), 4.00 (q, 2 H), 3.23 (t, 2 H), 2.93 (t, 2 H), 2.62 (t, 2 H), 2.40-2.42 (m, 5 H), 2.03-2.10 (m, 2 H), 1.12 (t, 3 H).

DCB-70065: $^1$H NMR (DMSO-$d_6$) δ 13.72 (s, 1 H), 11.42 (s, 1 H), 8.22 (d, 1 H), 7.91 (s, 1 H), 7.60 (dd, 1 H), 7.25 (d, 1 H), 7.07 (d, 1 H), 3.23 (t, 2 H), 2.93 (m, 2 H), 2.61 (m, 2 H), 2.41 (m, 4 H), 2.06 (m, 2 H), 1.12 (t, 3 H).

DCB-70066: $^1$H NMR (DMSO-$d_6$) δ 13.74 (s, 1 H), 11.06 (s, 1 H), 9.57 (s, 1 H), 7.81 (d, 1 H), 7.71 (s, 1 H), 7.47, (d, 2 H), 7.24 (d, 1 H), 7.04 (s, 1 H), 6.85 (d, 2 H), 4.00 (q, 2 H), 3.20 (m, 2 H), 2.92 (m, 2 H), 2.60 (m, 2 H), 2.41 (m, 2 H), 2.06 (m, 2 H), 1.12 (t, 3 H).

DCB-70067: $^1$H NMR (DMSO-$d_6$) δ 13.84 (s, 1 H), 11.07 (s, 1 H), 8.07 (s, 2 H), 7.43 (s, 1 H), 7.20 (m, 2 H), 6.88-6.99 (m, 2 H), 3.98 (q, 2 H), 3.86 (s, 3 H), 3.79 (s, 3 H), 3.16 (t, 2 H), 2.88 (t, 2 H), 2.37 (m, 2 H), 2.00 (m, 2 H).

DCB-70068: $^1$H NMR (DMSO-$d_6$) δ 13.70 (s, 1 H), 11.03 (s, 1 H), 8.03 (s, 1 H), 7.41 (d, 1 H), 7.19 (m, 2 H), 6.91-7.01 (m, 2 H), 3.85 (s, 3 H), 3.77 (s, 3 H), 3.15 (t, 2 H), 2.89 (t, 2 H), 2.37 (m, 2 H), 2.04 (m, 2 H).

DCB-70069: $^1$H NMR (DMSO-$d_6$) δ 13.80 (s, 1 H, NH), 11.21 (s, 1 H), 8.29 (s, 1 H), 7.95 (m, 2H), 7.83 (m, 2 H), 7.56 (t, 1 H), 7.34-7.39 (m, 2 H), 7.00 (d, 1 H), 4.01 (q, 2 H), 3.29 (m, 2 H), 2.93 (m, 2 H), 2.64 (m, 2 H), 2.42 (m, 2 H), 2.07 (m, 2 H), 1.13 (t, 3 H).

DCB-70070: $^1$H NMR (DMSO-$d_6$) δ 13.61 (s, 1 H), 8.19 (s, 1 H), 8.08 (s, 1 H), 7.92 (d, 1 H), 7.77 (d, 2 H), 7.45 (d, 1 H), 7.29-7.37 (m, 2 H), 6.91 (s, 1 H), 3.18 (m, 2 H), 2.81 (m, 2 H), 2.35 (m, 2H), 2.28 (m, 2 H), 2.01 (m, 2 H).

DCB-70071: $^1$H NMR (DMSO-$d_6$) δ 13.66 (s, 1 H), 8.19 (s, 1 H), 8.18 (s, 1 H), 7.43 (q, 1 H), 7.30 (m, 3 H), 7.20 (m, 2 H), 7.01 (d, 1 H), 4.61 (s, 2 H), 3.20 (m, 2 H), 2.93 (m, 2 H), 2.53 (m, 2 H), 2.44 (m, 2 H), 2.07 (m, 2 H).

DCB-70072: $^1$H NMR (DMSO-$d_6$) δ 13.67 (s, 1 H), 12.11 (s, 1 H), 11.49 (s, 1 H), 8.22 (s, 1 H), 7.94 (s, 1 H), 7.40 (m, 1 H), 7.22 (m, 2 H), 7.13 (m, 2 H), 7.01 (d, 1 H), 4.63 (s, 2 H), 3.21 (m, 2 H), 2.94 (m, 2 H), 2.53 (m, 2 H), 2.43 (m, 2 H), 2.07 (m, 2 H).

DCB-70073: $^1$H NMR (DMSO-$d_6$) δ 13.65 (s, 1 H), 11.52 (s, 1 H), 8.21 (s, 1 H), 7.94 (s, 1 H), 7.47-7.51 (m, 3 H), 7.37-7.40 (m, 1 H), 7.06 (d, 1 H), 3.20 (m, 2 H), 2.93 (m, 2 H), 2.52 (m, 2 H), 2.42 (m, 2 H), 2.06 (m, 2 H), 1.05 (m, 2 H).

DCB-70074: $^1$H NMR (DMSO-$d_6$) δ 13.82 (s, 1 H), 11.02 (s, 1 H), 10.22 (s, 1 H), 8.04-8.07 (m, 3H), 7.63 (s, 1 H), 7.48-7.50 (m, 1 H), 7.35-7.39 (m, 2 H), 6.89 (d, 1 H), 3.99 (q, 2 H), 3.15 (m, 2 H), 2.92 (m, 2 H), 2.63 (m, 2 H), 2.41 (m, 2 H), 2.06 (m, 2 H), 1.11 (t, 3 H).

DCB-70075: $^1$H NMR (DMSO-$d_6$) δ 13.72 (s, 1 H), 12.06 (brs, 1 H), 11.05 (s, 1 H), 9.58 (s, 1H), 7.78 (d, 1 H), 7.73 (s, 1 H), 7.47 (d, 2 H), 7.23 (m, 1 H), 7.03 (d, 1 H), 6.85 (d, 2 H), 3.16 (m, 2 H), 2.91 (m, 2 H), 2.51 (m, 2 H), 2.40 (m, 2 H), 2.05 (m, 2 H).

DCB-70076: $^1$H NMR (DMSO-$d_6$) δ 13.79 (s, 1 H), 11.00 (s, 1 H), 10.22 (s, 1 H), 8.06 (m, 2H), 7.98 (s, 1 H), 7.66 (s, 1 H), 7.53 (m, 1 H), 7.36 (m, 2 H), 6.88 (m, 1 H), 3.12 (m, 2 H), 2.91 (m, 2H), 2.53 (m, 2 H), 2.40 (m, 2 H), 2.06 (m, 2 H).

DCB-70077: $^1$H NMR (DMSO-$d_6$) δ 13.74 (s, 1 H), 7.80 (d, 1 H), 7.70 (s, 1 H), 7.20 (d, 1 H), 6.92-7.03 (m, 3 H), 6.81 (d, 1 H), 4.00 (q, 2 H), 3.19 (m, 2 H), 2.92 (m, 2 H), 2.60 (m, 2 H), 2.41 (m, 2H), 2.06 (m, 2 H), 1.12 (t, 3 H).

DCB-70078: $^1$H NMR (DMSO-$d_6$) δ 13.72 (s, 1 H), 11.04 (s, 1 H), 9.07 (d, 2 H), 7.73-7.78 (m, 2 H), 7.18-7.20 (m, 1 H), 6.92-7.03 (m, 3 H), 6.81 (d, 1 H), 3.16 (m, 2 H), 2.91 (m, 2 H), 2.41 (m, 2H), 2.06 (m, 2 H).

DCB-70079: $^1$H NMR (DMSO-$d_6$) δ 13.74 (s, 1 H), 7.71-7.96 (m, 5 H), 7.24-7.48 (m, 4 H), 4.00 (m, 2 H), 3.21 (m, 2 H), 2.92 (m, 2 H), 2.60 (m, 2 H), 2.41 (m, 2 H), 2.01 (m, 2 H), 1.12 (m, 3 H).

DCB-70080: $^1$H NMR (DMSO-$d_6$) δ 13.57 (s, 1 H), 11.39 (brs, 1 H), 7.72-8.05 (m, 5 H), 7.21-7.38 (m, 4 H), 3.16 (m, 2 H), 2.91 (m, 2 H), 2.41 (m, 2 H), 2.14 (m, 2 H), 1.97 (m, 2 H).

DCB-70081: $^1$H NMR (DMSO-$d_6$) δ 13.76 (s, 1 H), 11.06 (s, 1 H), 9.14 (s, 1 H), 7.82 (d, 1 H), 7.72 (s, 1 H), 7.29 (m, 1 H), 7.17 (m, 1 H), 7.07 (m, 2 H), 6.86 (d, 1 H), 4.00 (q, 2 H), 3.86 (s, 3 H), 3.20 (m, 2 H), 2.92 (m, 2 H), 2.61 (m, 2 H), 2.41 (m, 2 H), 2.06 (m, 2 H), 1.13 (t, 3 H).

DCB-70082: $^1$H NMR (DMSO-$d_6$) δ 13.74 (s, 1 H), 11.05 (s, 1 H), 7.78 (m, 2 H), 7.27 (m, 1 H), 7.17 (1 H), 7.06 (m, 2 H), 6.86 (m, 1 H), 3.86 (s, 3 H), 3.16 (m, 2 H), 2.92 (m, 2 H), 2.41 (m, 2 H), 2.06 (m, 2 H).

DCB-70083: $^1$H NMR (DMSO-$d_6$) δ 14.79 (s, 1 H), 7.88-8.01 (m, 2 H), 7.02-7.25 (m, 3 H), 3.95 (m, 2 H), 3.31 (m, 2 H), 3.00 (m, 2 H), 2.63 (m, 2 H), 2.45 (m, 2 H), 2.08 (m, 2 H), 1.10 (m, 3 H).

DCB-70084: $^1$H NMR (DMSO-$d_6$) δ 9.72 (s, 1 H), 8.23 (s, 1 H), 6.80-6.98 (m, 3 H), 6.60-6.58 (m, 2 H), 3.06 (m, 2 H), 2.73 (m, 2 H), 2.27 (m, 2 H), 2.06 (m, 2 H).

DCB-70085: $^1$H NMR (DMSO-$d_6$) δ 14.69 (s, 1 H), 7.83-8.03 (m, 2 H), 7.16-7.33 (m, 2 H), 3.94 (m, 2 H), 3.37 (m, 2 H), 2.95 (m, 2 H), 2.61 (m, 2 H), 2.45 (m, 2 H), 2.07 (m, 2 H), 1.08 (m, 3 H).

DCB-70086: $^1$H NMR (DMSO-$d_6$) δ 9.69 (s, 1 H), 6.68-7.06 (m, 5 H), 3.02 (m, 2 H), 2.72 (m, 2 H), 2.28 (m, 2 H), 2.20 (m, 2 H).

DCB-70087: $^1$H NMR (DMSO-$d_6$) δ 13.73 (s, 1 H), 8.25 (s, 1 H), 8.03 (s, 1 H), 7.61 (d, 1 H), 7.08 (s, 1 H), 3.22 (m, 2 H), 3.16 (m, 4 H), 2.93 (m, 2 H), 2.53 (m, 2 H), 2.42 (m, 2 H), 2.04 (m, 2 H), 1.64 (m, 4 H).

DCB-70088: $^1$H NMR (DMSO-$d_6$) δ 13.71 (s, 1 H), 11.49 (s, 1 H), 8.18 (s, 1 H), 8.01 (s, 1 H), 7.54 (d, 1 H), 7.11 (d, 1 H), 3.64 (m, 4 H), 3.21 (m, 2 H), 2.93 (m, 6 H), 2.53 (m, 2 H), 2.41 (m, 2 H), 2.05 (m, 2 H).

DCB-70091: $^1$H NMR (DMSO-$d_6$) δ 13.83 (s, 1 H), 10.91 (s, 1 H), 8.49 (s, 1 H), 8.46 (s, 1 H), 7.77 (s, 1 H), 7.61 (s, 1 H), 7.33 (m, 2 H), 7.18 (m, 1 H), 7.07 (m, 2 H), 6.81 (d, 1 H), 3.99 (q, 2 H), 3.15 (m, 2 H), 2.92 (m, 2 H), 2.62 (m, 2 H), 2.49 (m, 2 H), 2.23 (s, 3 H), 2.03 (m, 2 H), 1.10 (t, 3 H).

DCB-70092: $^1$H NMR (DMSO-$d_6$) δ 13.83 (s, 1 H), 10.93 (s, 1 H), 8.49 (s, 1 H), 8.46 (s, 1 H), 7.77 (s, 1 H), 7.61 (s, 1 H), 7.32 (m, 2 H), 7.18 (m, 1 H), 7.07 (m, 2 H), 6.81 (m, 1 H), 3.98 (q, 2 H), 3.15 (m, 2 H), 2.91 (m, 2 H), 2.61 (m, 2 H), 2.38 (m, 2 H), 2.23 (s, 3 H), 2.04 (m, 2 H), 1.10 (t, 3 H).

DCB-70093: $^1$H NMR (DMSO-$d_6$) δ 13.83 (s, 1 H), 10.90 (s, 1 H), 8.42 (s, 1 H), 8.41 (s, 1 H), 7.77 (s, 1 H), 7.60 (s, 1 H), 7.34 (m, 2 H), 7.18 (m, 1 H), 6.85 (m, 3 H), 3.97 (q, 2 H), 3.69 (s, 3 H), 3.29 (m, 2 H), 2.90 (m, 2 H), 2.61 (m, 2 H), 2.40 (m, 2 H), 2.05 (m, 2 H), 1.10 (t, 3 H).

DCB-70093: $^1$H NMR (DMSO-$d_6$) δ 13.84 (s, 1 H), 11.92 (s, 1 H), 10.98 (s, 1 H), 8.51 (d, 1 H), 7.78 (d, 1 H), 6.88-7.18 (m, 6 H), 3.18 (m, 2 H), 3.07 (m, 2 H), 2.63 (m, 2 H), 2.41 (m, 2 H), 2.06 (m, 2 H).

DCB-70094: $^1$H NMR (DMSO-$d_6$) δ 13.81 (s, 1 H), 11.91 (s, 1 H), 11.03 (s, 1 H), 8.50 (s, 1 H), 8.45 (s, 1 H), 7.81 (s, 1 H), 7.69 (s, 1 H), 6.89-7.24 (m, 6 H), 3.76 (s, 1 H), 3.17 (m, 2 H), 3.05 (m, 2 H), 2.63 (m, 2 H), 2.40 (m, 2 H), 2.05 (m, 2 H).

DCB-70095: $^1$H NMR (DMSO-$d_6$) δ 11.67 (s, 1 H), 8.21 (s, 1 H), 7.86 (s, 1 H), 7.65 (m, 1 H), 7.21 (s, 1 H), 7.02 (d, 1 H), 3.16 (m, 2 H), 2.91 (m, 2 H), 2.53 (m, 2 H), 2.40 (m, 2 H), 2.05 (m, 2 H).

DCB-70096: $^1$H NMR (DMSO-$d_6$) δ 13.83 (s, 1 H), 11.03 (s, 1 H), 10.21 (s, 1 H), 7.97-8.06 (m, 3H), 7.51-7.63 (m, 5 H), 6.90 (d, 1 H), 3.99 (q, 2 H), 3.16 (m, 2 H), 2.92 (m, 2 H), 2.63 (m, 2 H), 2.41 (m, 2 H), 2.06 (m, 2 H), 1.11 (t, 3 H).

DCB-70097: $^1$H NMR (DMSO-$d_6$) δ 13.81 (s, 1 H), 11.01 (s, 1 H), 10.20 (s, 1 H), 7.99 (m, 3 H), 7.57 (m, 5 H), 6.89 (d, 1 H), 3.12 (m, 2 H), 2.92 (m, 2 H), 2.40 (m, 2 H), 2.06 (m, 2 H).

DCB-70098: $^1$H NMR (DMSO-$d_6$) δ 7.85 (m, 1 H), 7.75 (s, 1 H), 7.68 (m, 2 H), 7.27 (m, 3 H), 7.10 (s, 1 H), 3.97 (q, 2 H), 3.19 (m, 2 H), 2.91 (m, 2 H), 2.59 (m, 2 H), 2.40 (m, 2 H), 2.04 (m, 2 H), 1.10 (t, 3 H).

DCB-70099: $^1$H NMR (DMSO-$d_6$) δ 13.71 (s, 1 H), 11.12 (s, 1 H), 7.83 (t, 2 H), 7.68 (t, 2 H), 7.28 (m, 3 H), 7.10 (s, 1 H), 3.15 (m, 2 H), 2.91 (m, 2 H), 2.41 (m, 4 H), 2.01 (m, 2 H).

DCB-70100: $^1$H NMR (DMSO-$d_6$) δ 7.89 (d, 1 H), 7.79 (s, 1 H), 7.42 (m, 3 H), 7.17 (m, 2 H), 3.97 (q, 2 H), 3.19 (m, 2 H), 2.91 (m, 2 H), 2.59 (m, 2 H), 2.04 (m, 2 H), 1.10 (t, 3 H).

DCB-70101: $^1$H NMR (DMSO-$d_6$) δ 13.73 (s, 1 H), 11.17 (s, 1 H), 7.86 (m, 2 H), 7.42 (m, 3 H), 7.21 (m, 1 H), 3.17 (m, 2 H), 2.92 (m, 2 H), 2.41 (m, 2 H), 2.01 (m, 2 H).

DCB-70102: $^1$H NMR (DMSO-$d_6$) δ 13.74 (s, 1 H), 11.12 (s, 1 H), 7.71 (m, 2 H), 7.56 (m, 4 H), 7.45 (s, 1 H), 6.74 (m, 2 H), 3.99 (q, 2 H), 3.15 (m, 2 H), 2.90 (m, 2 H), 2.62 (m, 2 H), 2.41 (m, 2H), 2.04 (m, 2 H), 1.09 (t, 3 H).

DCB-70103: $^1$H NMR (DMSO-$d_6$) δ 13.70 (s, 1 H), 10.96 (s, 1 H), 7.73 (s, 1 H), 7.54-7.60 (m, 4H), 7.40 (m, 1 H), 6.74 (m, 2 H), 2.90 (m, 2 H), 2.42 (m, 2 H), 2.05 (m, 2 H).

DCB-70104: $^1$H NMR (DMSO-$d_6$) δ 13.79 (s, 1 H), 10.94 (s, 1 H), 9.84 (s, 1H), 7.77 (s, 1 H), 7.60 (s, 1 H), 7.39 (m, 1 H), 6.82 (s, 1 H), 3.10 (m, 2 H), 2.91 (m, 2 H), 2.53 (m, 2 H), 2.41 (m, 2 H), 2.06 (m, 2 H), 2.02 (s, 1 H).

DCB-70106: $^1$H NMR (DMSO-$d_6$) δ 13.60 (s, 1 H), 11.42 (s, 1 H), 8.27 (s, 1 H), 7.93 (s, 1 H), 7.55-7.60 (m, 2 H), 7.12-7.20 (m, 2 H), 6.95-6.99 (m, 2 H), 3.92 (t, 2 H), 3.23 (m, 2 H), 2.91 (m, 4H), 2.51 (m, 2 H), 2.42 (m, 2 H), 2.05 (m, 2 H).

DCB-70107: $^1$H NMR (DMSO-$d_6$) δ 13.76 (s, 1 H), 11.58 (s, 1 H), 8.23 (s, 1 H), 8.02 (s, 1 H), 7.57 (m, 1 H), 7.14 (d, 1 H), 3.22 (m, 6 H), 2.94 (m 3 H), 2.64 (m, 3 H), 2.53 (m, 2 H), 2.43 (m, 2 H), 2.06 (m, 2 H).

DCB-70108: $^1$H NMR (DMSO-d$_6$) δ 13.82 (s, 1 H), 11.10 (s, 1 H), 8.12 (s, 1 H), 7.89 (s, 1 H), 7.73 (m, 2 H), 7.46 (m, 1 H), 7.29 (m, 2 H), 6.97 (d, 1 H), 3.98 (q, 2 H), 3.24 (m, 2 H), 2.92 (m, 2 H), 2.61 (m, 2 H), 2.41 (m, 2 H), 2.06 (m, 2 H), 1.10 (t, 3 H).

DCB-70109: $^1$H NMR (DMSO-d$_6$) δ 13.68 (s, 1 H), 8.14 (s, 1 H), 8.06 (s, 1 H), 7.76 (m, 2 H), 7.41 (m, 1 H), 7.24 (m, 2 H), 6.94 (d, 1 H), 3.14 (m, 2 H), 2.89 (m, 2 H), 2.38 (m, 2 H), 2.05 (m, 2 H).

DCB-70114: $^1$H NMR (DMSO-d$_6$) δ 13.73 (s, 1 H), 11.45 (s, 1 H), 8.17 (s, 1 H), 8.01 (s, 1 H), 7.52 (d, 1 H), 7.09 (d, 1 H), 3.22 (m, 2 H), 2.89-2.93 (m, 6 H), 2.53 (m, 2 H), 2.41 (m, 2 H), 2.06 (m, 2H), 1.55 (m, 4 H), 1.35 (m, 2 H).

DCB-70115: $^1$H NMR (DMSO-d$_6$) δ 13.67 (s, 1 H), 11.48 (s, 1 H), 8.32 (s, 1 H), 7.99 (s, 1 H), 7.62 (d, 1 H), 7.08 (d, 1 H), 5.71-5.73 (m, 1 H), 5.31 (d, 1 H), 5.24 (d, 1 H), 4.08 (d, 2 H), 3.20 (m, 2 H), 2.93 (m, 2 H), 2.54 (m, 2 H), 2.41 (m, 2 H), 2.06 (m, 2 H).

DCB-70116: $^1$H NMR (DMSO-d$_6$) δ 13.69 (s, 1 H), 11.49 (s, 1 H), 8.35 (s, 1 H), 8.01 (s, 1 H), 7.67 (d, 1 H), 7.10 (d, 1 H), 3.19-3.27 (m, 4 H), 2.93 (m, 2 H), 2.53 (m, 2 H), 2.41 (m, 2 H), 2.06 (m, 2H), 1.13 (t, 3 H).

DCB-70117: $^1$H NMR (DMSO-d$_6$) δ 13.70 (s, 1 H), 11.41 (s, 1 H), 8.17 (s, 1 H), 7.87 (s, 1 H), 7.59 (d, 1 H), 7.26 (d, 1 H), 7.07 (d, 1 H), 3.18 (m, 2 H), 3.92 (m, 2 H), 2.58 (m, 2 H), 2.42 (m, 5 H), 2.12 (m, 9 H).

DCB-70118: $^1$H NMR (DMSO-d$_6$) δ 13.81 (s, 1 H), 11.04 (s, 1 H), 9.46 (s, 1 H), 7.64 (s, 1 H), 7.58 (s, 1 H), 7.05 (d, 1 H), 6.87 (d, 1 H), 3.99 (q, 2 H), 3.17 (m, 2 H), 3.03 (m, 2 H), 2.93 (m, 2 H), 2.63 (m, 2 H), 2.41 (m, 2 H), 2.06 (m, 2 H), 1.11 (t, 3 H).

DCB-70119: $^1$H NMR (DMSO-d$_6$) δ 13.79 (s, 1 H), 11.03 (s, 1 H), 9.44 (s, 1 H), 7.68 (s, 1 H), 7.55 (s, 1 H), 7.21 (s, 1 H), 7.06 (d, 1 H), 6.87 (d, 1 H), 6.65 (s, 1 H), 3.13 (m, 2 H), 3.03 (m, 2 H), 2.92 (m, 2 H), 2.63 (m, 2 H), 2.42 (m, 2 H), 2.01 (m, 2 H).

DCB-70120: $^1$H NMR (DMSO-d$_6$) δ 13.70 (s, 1 H), 8.23 (s, 1 H), 7.98 (s, 1 H), 7.61 (d, 1 H), 7.08 (d, 1 H), 3.24 (m, 4 H), 3.17 (m, 2 H), 2.94 (m, 2 H), 2.57 (m, 2 H), 2.43 (m, 2 H), 2.06-2.13 (m, 9H).

DCB-70121: $^1$H NMR (DMSO-d$_6$) δ 13.73 (s, 1 H), 12.04 (s, 1 H), 11.45 (s, 1 H), 8.21 (s, 1 H), 8.02 (s, 1 H), 7.55 (d, 1 H), 7.10 (d, 1 H), 3.22 (m, 2 H), 2.93 (m, 2 H), 2.62 (s, 6 H), 2.53 (m, 2 H), 2.42 (m, 2 H), 2.06 (m, 2 H).

DCB-70122: $^1$H NMR (DMSO-d$_6$) δ 13.61 (s, 1 H), 11.15 (s, 1 H), 7.83 (m, 1 H), 7.72 (m, 1 H), 6.84 (m, 1 H), 6.71 (m, 1 H), 3.98 (q, 2 H), 3.19 (m, 2 H), 2.91 (m, 2 H), 2.58 (m, 2 H), 2.40 (m, 2H), 2.06 (m, 2 H), 1.13 (t, 3 H).

DCB-70123: $^1$H NMR (DMSO-d$_6$) δ 13.58 (s, 1 H), 11.13 (s, 1 H), 7.79 (m, 1 H), 7.73 (s, 1 H), 6.83 (m, 1 H), 6.71 (m, 1 H), 3.15 (m, 2 H), 2.91 (m, 2 H), 2.40 (m, 2 H), 2.05 (m, 2 H).

DCB-70124: $^1$H NMR (DMSO-d$_6$) δ 13.80 (s, 1 H), 10.99 (s, 1 H), 7.83 (s, 1 H), 7.75 (m, 1 H), 6.97 (m, 1 H), 6.85 (m, 1 H), 3.21 (m, 6 H), 2.92 (m, 2 H), 2.53 (m, 2 H), 2.41 (m, 2 H), 2.05 (m, 2H), 0.98 (m, 6 H).

DCB-70125: $^1$H NMR (DMSO-d$_6$) δ 13.80 (s, 1 H), 11.00 (s, 1 H), 7.74-7.85 (m, 2 H), 6.97 (m, 1H), 6.85 (m, 1 H), 3.38-3.48 (m, 6 H), 3.18 (m, 2 H), 2.91 (m, 2 H), 2.51 (m, 2 H), 2.41 (m, 2 H), 2.05 (m, 2 H).

DCB-70128: $^1$H NMR (DMSO-d$_6$) δ 13.75 (s, 1 H), 7.83 (d, 1 H), 7.74 (s, 1 H), 7.27 (d, 1 H), 7.23 (s, 1 H), 7.13 (d, 1 H), 7.05 (s, 1 H), 7.00 (d, 1 H), 6.07 (s, 2 H), 3.99 (q, 2 H), 3.22 (m, 2 H), 2.92 (m, 2 H), 2.60 (m, 2 H), 2.41 (m, 2 H), 2.06 (m, 2 H), 1.12 (t, 3 H).

DCB-70129: $^1$H NMR (DMSO-d$_6$) δ 13.84 (s, 1 H), 10.94 (s, 1 H), 10.25 (s, 1 H), 8.95 (s, 1 H), 8.74 (s, 1 H), 7.84-8.13 (m, 3 H), 7.45-7.65 (m, 5 H), 7.21 (m, 1 H), 6.76 (m, 1 H), 3.99 (q, 2 H), 3.17 (m, 2 H), 2.92 (m, 2 H), 2.63 (m, 2 H), 2.41 (m, 2 H), 2.06 (m, 2 H), 1.11 (t, 3 H).

DCB-70130: $^1$H NMR (DMSO-d$_6$) δ 13.67 (s, 1 H), 11.15 (s, 1 H), 7.79 (s+d, 2 H), 7.21 (d, 1 H), 7.04 (s, 1 H), 3.98 (q, 2 H), 3.19 (m, 2 H), 2.92 (m, 2 H), 2.60 (m, 2 H), 2.41 (m, 2 H), 2.06 (m, 2H), 1.12 (t, 2 H).

DCB-70131: $^1$H NMR (DMSO-d$_6$) δ 13.92 (s, 1 H), 10.60 (s, 1 H), 7.21-7.49 (m, 6 H), 7.05 (s, 1H), 6.61 (d, 1 H), 6.45 (m, 1 H), 4.28 (d, 2 H), 3.98 (q, 2 H), 3.14 (m, 2 H), 2.89 (m, 2 H), 2.61 (m, 2 H), 2.38 (m, 2 H), 2.05 (m, 2 H), 1.10 (t, 3 H).

DCB-70132: $^1$H NMR (DMSO-d$_6$) δ 13.73 (s, 1 H), 11.13 (s, 1 H), 6.99-7.77 (m, 9 H), 3.17 (m, 2H), 2.92 (m, 2 H), 2.63 (m, 2 H), 2.46 (m, 2 H), 2.06 (m, 2 H).

DCB-70133: $^1$H NMR (DMSO-d$_6$) δ 13.67 (s, 1 H), 7.83 (s, 1 H), 7.54 (s, 1 H), 6.99-7.09 (m, 2 H), 3.10 (m, 2 H), 2.87 (m, 2 H), 2.38 (m, 2 H), 2.04 (m, 2 H).

DCB-70134: $^1$H NMR (DMSO-d$_6$) δ 13.85 (s, 1 H), 10.93 (s, 1 H), 8.62 (s, 1 H), 8.53 (s, 1 H), 7.80 (s, 1 H), 7.64 (s, 1 H), 7.48 (m, 2 H), 7.29 (m, 2 H), 7.22-7.30 (m, 2 H), 6.97 (m, 1 H), 6.84 (m, 1H), 4.01 (q, 2 H), 3.18 (m, 2 H), 2.93 (m, 2 H), 2.64 (m, 2 H), 2.48 (m, 2 H), 2.08 (m, 2 H), 1.13 (t, 3 H).

DCB-70135: $^1$H NMR (DMSO-d$_6$) δ 13.85 (s, 1 H), 10.94 (s, 1 H), 8.78 (s, 1 H), 8.57 (s, 1 H), 7.81 (s, 1 H), 7.64 (s, 1 H), 7.43 (m, 6 H), 7.20 (m, 1 H), 6.84 (m, 1 H), 4.01 (q, 2 H), 3.18 (m, 2 H), 2.93 (m, 2 H), 2.64 (m, 2 H), 2.43 (m, 2 H), 2.07 (m, 2 H), 1.13 (t, 3 H).

DCB-70136: $^1$H NMR (DMSO-d$_6$) δ 13.85 (s, 1 H), 10.93 (s, 1 H), 8.65 (s, 1 H), 8.52 (s, 1 H), 7.80 (s, 1 H), 7.63 (s, 1 H), 7.48 (m, 2 H), 7.11-7.22 (m, 3 H), 6.84 (m, 1 H), 4.01 (q, 2 H), 3.18 (m, 2H), 2.93 (m, 2 H), 2.64 (m, 2 H), 2.43 (m, 2 H), 2.07 (m, 2 H), 1.13 (t, 3 H).

DCB-70137: $^1$H NMR (DMSO-d$_6$) δ 13.85 (s, 1 H), 10.96 (s, 1 H), 9.13 (s, 1 H), 8.70 (s, 1 H), 8.14 (s, 1 H), 7.81 (s, 1 H), 7.61-7.67 (m, 3 H), 7.22 (m, 1 H), 6.85 (m, 1 H), 4.01 (q, 2 H), 3.19 (m, 2 H), 2.93 (m, 2 H), 2.63 (m, 2 H), 2.43 (m, 2 H), 2.08 (m, 2 H), 1.13 (t, 3 H).

DCB-70138: $^1$H NMR (DMSO-d$_6$) δ 13.88 (s, 1 H), 11.00 (s, 1 H), 7.78 (m, 2 H), 6.96 (m, 1 H), 6.86 (m, 1 H), 4.00 (q, 2 H), 3.21 (m, 2 H), 3.02 (m, 2 H), 2.62 (m, 2 H), 1.79-1.86 (m, 4 H), 1.13 (t, 3 H).

DCB-70139: $^1$H NMR (DMSO-d$_6$) δ 13.86 (s, 1 H), 10.99 (s, 1 H), 7.81 (s, 1 H), 7.74 (m, 1 H), 6.96 (m, 1 H), 6.86 (m, 1 H), 3.15 (m, 2 H), 3.02 (m, 2 H), 2.62 (m, 2 H), 2.46 (m, 2 H), 1.79-1.86 (m, 4 H).

DCB-70140: $^1$H NMR (DMSO-d$_6$) δ 11.06 (s, 1 H), 10.53 (s, 1 H), 8.39 (m, 2 H), 8.22 (m, 2 H), 8.06 (s, 1 H), 7.65 (s, 1 H), 7.53 (m, 1 H), 6.92 (m, 1 H), 4.00 (q, 2 H), 3.17 (m, 2 H), 2.93 (m, 2 H), 2.64 (m, 2 H), 2.42 (m, 2 H), 2.07 (m, 2 H), 1.11 (t, 3 H).

DCB-70141: $^1$H NMR (DMSO-d$_6$) δ 13.84 (s, 1 H), 11.01 (s, 1 H), 10.05 (s, 1 H), 8.05 (s, 1 H), 7.98 (d, 2 H), 7.63 (s, 1 H), 7.50 (d, 1 H), 7.06 (d, 2 H), 6.88 (m, 2 H), 4.00 (q, 2 H), 3.84 (s, 1 H), 3.16 (m, 2 H), 2.93 (m, 2 H), 2.63 (m, 2 H), 2.42 (m, 2 H), 2.07 (m, 2 H), 1.12 (t, 3 H).

DCB-70142: $^1$H NMR (DMSO-d$_6$) δ 13.83 (s, 1 H), 11.06 (s, 1 H), 10.54 (s, 1 H), 8.37 (m, 2 H), 8.23 (m, 2 H), 8.02 (s, 1 H), 7.75 (s, 1 H), 7.57 (m, 1 H), 6.93 (m, 1 H), 3.13 (m, 2 H), 2.93 (m, 2 H), 2.42 (m, 2 H), 2.07 (m, 2 H).

DCB-70143: $^1$H NMR (DMSO-d$_6$) δ 13.83 (s, 1 H), 11.01 (s, 1 H), 10.06 (s, 1 H), 8.00 (m, 3 H), 7.66 (br, 1 H), 7.53 (br, 1 H), 7.07 (br, 2 H), 6.87 (br, 1 H), 3.84 (s, 1 H), 3.20 (m, 2 H), 2.92 (m, 2H), 2.41 (m, 2 H), 2.06 (m, 2 H).

DCB-70144: $^1$H NMR (DMSO-d$_6$) δ 13.76 (s, 1 H), 11.00 (s, 1 H), 9.94 (s, 1 H), 7.76 (m, 2 H), 7.60 (s, 1 H), 7.49 (s, 1 H), 7.39 (m, 2 H), 6.74 (brs, 2 H), 4.00 (q, 3 H), 3.16 (s, 1 H), 2.91 (s, 1 H), 2.62 (s, 1 H), 2.41 (s, 1 H), 1.99 (t, 3 H).

DCB-70145: $^1$H NMR (DMSO-$d_6$) δ 13.75 (s, 1 H), 12.05 (br, 1 H), 10.99 (s, 1 H), 9.95 (s, 1 H), 7.78 (m, 2 H), 7.64 (s, 1 H), 7.48 (s, 1 H), 7.39 (m, 2 H), 6.74 (m, 2 H), 3.13 (s, 1 H), 2.91 (s, 1 H), 2.54 (s, 1 H), 2.41 (s, 1 H), 2.06 (t, 3 H).

DCB-70146: $^1$H NMR (DMSO-$d_6$) δ 13.83 (s, 1 H), 10.96 (s, 1 H), 9.92 (s, 1 H), 7.72 (m, 2 H), 7.45-7.60 (m, 5 H), 6.74 (m, 2 H), 4.01 (q, 2 H), 3.16 (m, 2 H), 3.02 (m, 2 H), 2.55-2.64 (m, 4 H), 1.79-1.86 (m, 4 H), 1.11 (t, 3 H).

DCB-70147: $^1$H NMR (DMSO-$d_6$) δ 13.81 (s, 1 H), 12.09 (brs, 1 H), 10.99 (s, 1 H), 9.95 (s, 1 H), 7.74 (m, 2 H), 7.53-7.62 (m, 4 H), 6.74 (m, 2 H), 3.12 (m, 2 H), 3.02 (m, 2 H), 2.63 (m, 2 H), 2.47 (m, 2 H), 1.79-1.86 (m, 4 H).

DCB-70148: $^1$H NMR (DMSO-$d_6$) δ 13.81 (s, 13.66), 8.01 (s, 1 H), 7.90 (s, 1 H), 7.36 (m, 2 H), 7.24 (m, 2 H), 7.15 (m, 1 H), 7.02 (m, 1 H), 3.14-3.21 (m, 5 H), 2.93 (m, 2 H), 2.52 (m, 2 H), 2.42 (m, 2 H), 2.06 (m, 2 H).

DCB-70149: $^1$H NMR (DMSO-$d_6$) δ 13.63 (s, 1 H), 11.43 (s, 1 H), 10.37 (s, 1 H), 8.23 (s, 1 H), 7.92 (s, 1 H), 7.53 (d, 1 H), 7.25-7.31 (m, 2 H), 7.10 (m, 1 H), 7.02 (m, 1 H), 3.19 (m, 2 H), 2.92 (m, 2 H), 2.53 (m, 2 H), 2.41 (m, 2 H), 2.05 (m, 2 H).

DCB-70150: $^1$H NMR (DMSO-$d_6$) δ 13.81 (s, 1 H), 11.05 (s, 1 H), 9.59 (s, 1 H), 7.80 (d, 1 H), 7.69 (s, 1 H), 7.48 (d, 2 H), 7.24 (m, 1 H), 7.04 (s, 1 H), 6.85 (m, 2 H), 3.99 (q, 2 H), 3.15 (m, 2 H), 3.02 (m, 2 H), 2.64 (m, 2 H), 2.55 (m, 2 H), 1.95 (m, 4 H), 1.12 (t, 3 H).

DCB-70151: $^1$H NMR (DMSO-$d_6$) δ 13.79 (s, 1 H), 11.03 (s, 1 H), 9.58 (s, 1 H), 7.72-7.77 (m, 2H), 7.47 (d, 2 H), 7.23 (d, 1 H), 7.04 (s, 1 H), 6.85 (d, 2 H), 3.14 (m, 2 H), 3.01 (m, 2 H), 2.62 (m, 2H), 2.46 (m, 2 H), 1.79-1.88 (m, 4 H).

DCB-70152: $^1$H NMR (DMSO-$d_6$) δ 13.64 (s, 1 H), 8.21 (s, 1 H), 7.94 (s, 1 H), 7.47-7.49 (m, 3 H), 7.38 (m, 3 H), 7.05 (d, 1 H), 4.89 (s, 2 H), 3.21-3.32 (m, 4 H), 2.93 (m, 2 H), 2.41 (m, 2 H), 2.06 (m, 2 H), 1.83 (m, 2 H), 1.72 (m, 2 H).

DCB-70153: $^1$H NMR (DMSO-$d_6$) δ 13.66 (s, 1 H), 8.21 (s, 1 H), 7.90 (s, 1 H), 7.48 (m, 3 H), 7.38 (m, 1 H), 7.05 (d, 1 H), 4.88 (s, 2 H), 3.38 (m, 4 H), 3.20 (m, 2 H), 2.93 (m, 2 H), 2.57 (m, 2 H), 2.42 (m, 2 H), 2.06-2.16 (m, 9 H).

DCB-70154: $^1$H NMR (DMSO-$d_6$) δ 13.96 (s, 1 H), 10.81 (s, 1 H), 7.70 (s, 1 H), 7.45 (s, 1 H), 6.74-6.80 (m, 2 H), 3.99 (q, 2 H), 3.77 (s, 3 H), 3.21 (m, 2 H), 3.01 (m, 2 H), 2.62 (m, 2 H), 2.51 (m, 2 H), 1.86 (m, 4 H), 1.12 (t, 3 H).

DCB-70155: $^1$H NMR (DMSO-$d_6$) δ 13.94 (s, 1 H), 10.80 (s, 1 H), 7.74 (s, 1 H), 6.77 (m, 2 H), 3.77 (s, 3 H), 3.16 (m, 2 H), 3.01 (m, 2 H), 2.62 (m, 2 H), 2.47 (m, 2 H), 1.79-1.86 (m, 4 H).

DCB-70156: $^1$H NMR (DMSO-$d_6$) δ 13.81 (s, 1 H), 11.01 (s, 1 H), 7.75 (m, 2 H), 6.96 (s, 1 H), 6.86 (s, 1 H), 3.18 (m, 2 H), 2.91 (m, 2 H), 2.54 (m, 2 H), 2.41 (m, 2 H), 2.33 (m, 4 H), 2.23 (m, 3H), 2.05 (m, 2 H).

DCB-70157: $^1$H NMR (DMSO-$d_6$) δ 13.61 (s, 1 H), 8.22 (s, 1 H), 7.90 (s, 1 H), 7.72 (m, 1 H), 7.48-7.50 (m, 3 H), 7.37-7.41 (m, 1 H), 7.06 (d, 1 H), 4.88 (s, 2 H), 3.21 (m, 2 H), 2.94 (m, 2 H), 2.50 (s, 3 H), 2.36-2.43 (m, 4 H), 2.07 (m, 2 H).

DCB-70158: $^1$H NMR (DMSO-$d_6$) δ 13.69 (s, 1 H), 8.26 (s, 1 H), 7.93 (s, 1 H), 7.48-7.50 (m, 3 H), 7.39 (m, 1 H), 7.06 (d, 1 H), 4.88 (s, 2 H), 4.01 (q, 2 H), 3.25 (m, 2 H), 2.84 (s, 2 H), 2.61 (m, 2H), 2.33 (s, 2 H), 1.12 (t, 3 H), 1.05 (s, 6 H).

DCB-70159: $^1$H NMR (DMSO-$d_6$) δ 13.29 (s, 1 H), 7.85 (s, 1 H), 7.90 (s, 1 H), 7.49 (m, 2 H), 7.40 (m, 1 H), 7.26 (m, 2 H), 6.79 (d, 1 H), 4.90 (s, 2 H), 3.11 (t, 2 H), 2.79 (s, 2 H), 2.26-2.30 (m, 4 H), 1.04 (s, 6 H).

DCB-70160: $^1$H NMR (DMSO-$d_6$) δ 13.65 (s, 1 H), 11.44 (s, 1 H), 8.32 (s, 1 H), 7.92 (s, 1 H), 7.55-7.59 (m, 2 H), 7.12-7.18 (m, 2 H), 6.93-7.00 (m, 2 H), 3.92-4.00 (m, 4 H), 3.29 (m, 2 H), 2.91 (m, 2 H), 2.82 (s, 2 H), 2.62 (m, 2 H), 2.32 (s, 2 H), 1.10 (t, 3 H), 1.05 (s, 6 H).

DCB-70161: $^1$H NMR (DMSO-$d_6$) δ 13.63 (s, 1 H), 12.10 (s, 1 H), 11.43 (s, 1 H), 8.28 (s, 1 H), 7.93 (s, 1 H), 7.55-7.59 (m, 2 H), 7.20 (m, 1 H), 7.13 (d, 1 H), 6.94-7.00 (m, 2 H), 3.92 (q, 2 H), 3.25 (m, 2 H), 2.89 (m, 2 H), 2.82 (m, 2 H), 2.52 (m, 2 H), 2.33 (s, 2 H), 1.04 (s, 6 H).

DCB-70166: $^1$H NMR (DMSO-$d_6$) δ 13.90 (s, 1 H), 10.84 (s, 1 H), 7.74 (s, 1 H), 7.47 (s, 1 H), 6.74-6.80 (m, 2 H), 3.99 (q, 2 H), 3.77 (s, 3 H), 3.20 (m, 2 H), 2.91 (m, 2 H), 2.59 (m, 2 H), 2.40 (m, 2 H), 2.06 (m, 2 H), 1.12 (t, 3 H).

DCB-70167: $^1$H NMR (DMSO-$d_6$) δ 13.88 (s, 1 H), 10.82 (s, 1 H), 7.75 (s, 1 H), 7.42 (s, 1 H), 6.74-6.80 (m, 2 H), 3.77 (s, 3 H), 3.17 (m, 2 H), 2.90 (m, 2 H), 2.40 (m, 2 H), 2.05 (m, 2 H).

DCB-70168: $^1$H NMR (DMSO-$d_6$) δ 13.88 (s, 1 H), 10.99 (s, 1 H), 7.72 (d, 2 H), 7.52-7.71 (m, 5H), 6.74 (m, 2 H), 5.32 (s, 1 H), 3.98 (q, 2 H), 3.32 (m, 2 H), 2.81 (s, 2 H), 2.63 (m, 2 H), 2.32 (s, 2 H), 1.04 (s, 6 H).

DCB-70169: $^1$H NMR (DMSO-$d_6$) δ 11.01 (s, 1 H), 9.95 (s, 1 H), 7.73 (d, 2 H), 7.52-7.60 (m, 4 H), 7.43 (s, 1 H), 6.72-6.77 (m, 2 H), 3.12 (m, 2 H), 2.81 (s, 2 H), 2.53 (m, 2 H), 2.36 (s, 2 H), 1.04 (s, 6 H).

DCB-70170: $^1$H NMR (DMSO-$d_6$) δ 11.04 (s, 1 H), 7.74-7.78 (m, 2 H), 7.03-7.05 (m, 2 H), 6.83 (s, 1 H) 3.99 (q, 2 H), 3.19 (m, 2 H), 2.92 (m, 2 H), 2.58 (m, 2 H), 2.45 (m, 4 H), 2.06 (m, 2 H), 0.87-1.31 (m, 14 H).

DCB-70171: $^1$H NMR (DMSO-$d_6$) δ 13.67 (s, 1 H), 11.02 (s, 1 H), 7.74 (m, 2 H), 7.01 (s, 1 H), 6.81 (s, 1 H), 3.15 (m, 2 H), 2.90 (m, 2 H), 2.61 (m, 2 H), 2.39 (m, 4 H), 2.05 (m, 2 H), 0.86-1.52 (m, 11 H).

DCB-70172: $^1$H NMR (DMSO-$d_6$) δ 13.73 (s, 1 H), 11.12 (s, 1 H), 7.91 (s, 1 H), 7.83 (s, 1 H), 7.18 (d, 1 H), 6.85 (d, 1 H), 4.01 (q, 2 H), 3.22 (m, 2 H), 2.91 (m, 2 H), 2.55 (m, 2 H), 2.39 (m, 4 H), 2.06 (m, 2 H), 0.86-1.54 (m, 14 H).

DCB-70173: $^1$H NMR (DMSO-$d_6$) δ 13.70 (s, 1 H), 12.00 (brs, 1 H), 11.09 (s, 1 H), 7.86 (s, 1 H), 7.83 (s, 1 H), 7.16 (d, 1 H), 6.83 (d, 1 H), 3.17 (m, 2 H), 2.90 (m, 2 H), 2.62 (m, 2 H), 2.38 (m, 4H), 2.06 (m, 2 H), 0.83-1.52 (m, 11 H).

DCB-70174: $^1$H NMR (DMSO-$d_6$) δ 13.85 (s, 1 H), 10.84 (s, 1 H), 8.11 (s, 1 H), 7.70 (s, 1 H), 7.55 (s, 1 H), 7.04 (m, 1 H), 6.75 (m, 1 H), 5.80 (s, 1 H), 4.00 (q, 2 H), 3.15 (m, 2 H), 2.91 (m, 2 H), 2.63 (m, 2 H), 2.38 (m, 2 H), 2.02 (m, 6 H), 1.93 (m, 6 H), 1.63 (m, 6 H), 1.11 (t, 3 H).

DCB-70175: $^1$H NMR (DMSO-$d_6$) δ 13.92 (s, 1 H), 10.60 (s, 1 H), 7.49 (s, 1 H), 7.31 (d, 2 H), 7.04 (s, 1 H), 6.87 (d, 2 H), 6.60 (d, 1 H), 6.45 (m, 1 H), 5.77 (m, 1 H), 4.19 (m, 2 H), 3.98 (q, 2 H), 3.71 (s, 3 H), 2.81 (m, 2 H), 2.70 (m, 2 H), 2.51 (m, 2 H), 2.46 (m, 2 H), 2.08 (m, 2 H), 1.10 (t, 3 H).

DCB-70176: $^1$H NMR (DMSO-$d_6$) δ 13.91 (s, 1 H), 10.61 (s, 1 H), 7.49 (s, 1 H), 7.43 (m, 2 H), 7.13 (m, 2 H), 7.03 (s, 1 H), 6.61 (m, 1 H), 6.42 (m, 1 H), 5.82 (m, 1 H), 4.28 (d, 2 H), 3.97 (q, 2 H), 3.14 (m, 2 H), 2.89 (m, 2 H), 2.61 (m, 2 H), 2.40 (m, 2 H), 2.05 (m, 2 H), 1.10 (t, 3 H).

DCB-70177: $^1$H NMR (DMSO-$d_6$) δ 13.82 (s, 1 H), 11.12 (s, 1 H), 9.08 (s, 1 H), 8.80 (s, 1 H), 8.69 (d, 1 H), 8.32 (d, 1 H), 7.93 (d, 1 H), 7.86 (s, 1 H), 7.55 (m, 1 H), 7.22 (m, 1 H), 6.95 (d, 1 H), 4.00 (q, 2 H), 3.21 (m, 2 H), 2.93 (m, 2 H), 2.61 (m, 2 H), 2.41 (m, 2 H), 2.01 (m, 2 H), 1.13 (t, 3 H).

DCB-70178: $^1$H NMR (DMSO-$d_6$) δ 13.81 (s, 1 H), 11.12 (s, 1 H), 8.82 (s, 1 H), 8.31-8.34 (m, 2H), 7.92 (s, 1 H), 7.85 (s, 1 H), 7.70 (m, 1 H), 7.22 (m, 1 H), 6.95 (m, 1 H), 4.00 (q, 2 H), 3.22 (m, 2H), 2.93 (m, 2 H), 2.59 (m, 2 H), 2.46 (m, 2 H), 2.01 (m, 2 H), 1.12 (t, 3 H).

DCB-70179: $^1$H NMR (DMSO-$d_6$) δ 13.85 (s, 1 H), 10.56 (s, 1 H), 7.40 (m, 3 H), 7.27 (m, 2 H), 7.15 (m, 1 H), 6.95 (s,

1 H), 6.53 (d, 1 H), 6.34 (m, 1 H), 5.85 (m, 1 H), 4.50 (q, 1 H), 4.00 (q, 2 H), 3.13 (m, 2 H), 2.88 (m, 2 H), 2.62 (m, 2 H), 2.38 (m, 2 H), 2.04 (m, 2 H), 1.41 (d, 3 H), 1.11 (t, 3 H).

DCB-70180: $^1$H NMR (DMSO-d$_6$) δ 13.93 (s, 1 H), 10.61 (s, 1 H), 7.52 (s, 1 H), 7.46 (d, 1 H), 7.39 (d, 1 H), 7.08-7.13 (m, 2 H), 6.63 (d, 1 H), 6.50 (d, 1 H), 5.71 (m, 1 H), 4.27 (d, 2 H), 3.99 (q, 2 H), 3.16 (m, 2 H), 2.90 (m, 2 H), 2.61 (m, 2 H), 2.46 (m, 2 H), 2.05 (m, 2 H), 1.11 (t, 3 H).

DCB-70183: $^1$H NMR (DMSO-d$_6$) δ 13.83 (s, 1 H), 10.94 (s, 1 H), 8.90 (s, 1 H), 8.47 (s, 1 H), 8.11 (m, 1 H), 7.78 (s, 1 H), 7.63 (s, 1 H), 7.30 (m, 1 H), 7.22 (m, 1 H), 7.05 (m, 1 H), 6.83 (d, 1 H), 4.00 (q, 2 H), 3.16 (m, 2 H), 2.92 (m, 2 H), 2.63 (m, 2 H), 2.41 (m, 2 H), 2.06 (m, 2 H), 1.11 (t, 3 H).

DCB-70184: $^1$H NMR (DMSO-d$_6$) δ 13.83 (s, 1 H), 10.95 (s, 1 H), 9.43 (s, 1 H), 8.35 (s, 1 H), 8.24 (d, 1 H), 7.79 (s, 1 H), 7.62 (m, 2 H), 7.38 (m, 1 H), 7.25 (m, 1 H), 6.85 (m, 1 H), 3.99 (q, 2 H), 3.16 (m, 2 H), 2.92 (m, 2 H), 2.62 (m, 2 H), 2.40 (m, 2 H), 2.06 (m, 2 H), 1.11 (t, 3 H).

DCB-70186: $^1$H NMR (DMSO-d$_6$) δ 13.76 (s, 1 H), 10.96 (s, 1 H), 9.17 (s, 1 H), 7.63-7.73 (m, 2 H), 7.43-7.55 (m, 5 H), 7.12 (m, 2 H), 6.66-6.75 (m, 3 H), 6.41 (s, 1 H), 3.21 (m, 2 H), 2.96 (m, 2H), 2.67 (m, 2 H), 2.45 (m, 2 H), 2.01 (m, 2 H).

DCB-70187: $^1$H NMR (DMSO-d$_6$) δ 7.80 (s, 1 H), 7.74 (d, 2 H), 6.96 (d, 1 H), 6.86 (m, 1 H), 3.20 (t, 2 H), 2.61 (m, 2 H), 2.38-2.46 (m, 5 H).

DCB-70188: $^1$H NMR (DMSO-d$_6$) δ 8.25 (s, 1 H), 7.90 (s, 1 H), 7.58 (m, 2 H), 7.20 (m, 1 H), 7.13 (m, 1 H), 6.92-7.01 (m, 2 H), 3.92 (q, 2 H), 3.28 (m, 2 H), 2.90 (m, 2 H), 2.62 (s, 3 H), 2.45-2.47 (m, 5 H).

DCB-70189: $^1$H NMR (DMSO-d$_6$) δ 13.75 (s, 1 H), 11.03 (s, 1 H), 10.16 (s, 1 H), 7.59-7.64 (m, 2H), 7.53 (s, 1 H), 7.39 (s, 2 H), 6.75-6.79 (m, 2 H), 3.99 (q, 2 H), 3.16 (m, 2 H), 2.91 (m, 2 H), 2.61 (m, 2 H), 2.41 (m, 2 H), 2.06 (m, 2 H), 1.10 (t, 3 H).

DCB-70190: $^1$H NMR (DMSO-d$_6$) δ 13.74 (s, 1 H), 11.03 (s, 1 H), 10.16 (s, 1 H), 7.68 (s, 1 H), 7.61 (m, 1 H), 7.52 (s, 1 H), 7.40 (d, 1 H), 6.73-6.78 (m, 2 H), 3.13 (m, 2 H), 2.91 (m, 2 H), 2.53 (m, 2 H), 2.41 (m, 2 H), 2.05 (m, 2 H).

DCB-70191: $^1$H NMR (DMSO-d$_6$) δ 13.74 (s, 1 H), 10.95 (s, 1 H), 10.05 (s, 1 H), 8.37 (s, 1 H), 8.09 (d, 2 H), 8.00 (d, 1 H), 7.50-7.79 (m, 5 H), 6.76 (d, 1 H), 6.69 (d, 1 H), 3.95 (q, 2 H), 3.13 (m, 2 H), 2.90 (m, 2 H), 2.61 (m, 2 H), 2.40 (m, 2 H), 2.01 (m, 2 H), 1.06 (t, 3 H).

DCB-70192: $^1$H NMR (DMSO-d$_6$) δ 13.72 (s, 1 H), 10.94 (s, 1 H), 10.04 (s, 1 H), 8.37 (s, 1 H), 8.10 (d, 2 H), 8.01 (d, 1 H), 7.77-7.80 (m, 1 H), 7.59-7.68 (m, 2 H), 7.50 (s, 1 H), 6.67-6.75 (m, 2H), 3.10 (m, 2 H), 2.89 (m, 2 H), 2.40 (m, 2 H), 2.04 (m, 2 H).

DCB-70193: $^1$H NMR (DMSO-d$_6$) δ 13.77 (s, 1 H), 1.87 (s, 1 H), 7.64 (d, 2 H), 7.60 (s, 1 H), 7.43 (s, 1 H), 6.74 (s, 2 H), 4.00 (q, 2 H), 3.17 (m, 2 H), 2.91 (m, 2 H), 2.61 (m, 2 H), 2.41 (m, 2 H), 2.06 (m, 2 H), 1.10 (t, 3 H).

DCB-70194: $^1$H NMR (DMSO-d$_6$) δ 13.75 (s, 1 H), 11.04 (s, 1 H), 10.15 (s, 1 H), 7.95 (s, 1 H), 7.68 (s, 3 H), 7.50 (s, 1 H), 6.73-6.80 (m, 2 H), 3.14 (m, 2 H), 2.91 (m, 2 H), 2.41 (m, 2 H), 2.01 (m, 2 H).

DCB-70195: $^1$H NMR (DMSO-d$_6$) δ 13.76 (s, 1 H), 10.99 (s, 1 H), 9.92 (s, 1 H), 7.58 (s, 1 H), 7.43-7.49 (m, 2 H), 7.17-7.28 (m, 3 H), 6.76 (m, 2 H), 4.00 (q, 2 H), 3.75 (s, 3 H), 3.16 (m, 2 H), 2.91 (m, 2 H), 2.62 (m, 2 H), 2.41 (m, 1 H), 2.06 (m, 2 H), 1.10 (t, 3 H).

DCB-70196: $^1$H NMR (DMSO-d$_6$) δ 13.75 (s, 1 H), 10.98 (s, 1 H), 9.91 (s, 1 H), 7.61 (s, 1 H), 7.43-7.46 (m, 2 H), 7.16-7.29 (m, 3 H), 6.73-6.78 (m, 2 H), 3.76 (s, 3 H), 3.12 (m, 2 H), 2.91 (m, 2 H), 2.41 (m, 2 H), 2.05 (m, 2 H).

DCB-70197: $^1$H NMR (DMSO-d$_6$) δ 13.81 (s, 1 H), 11.04 (s, 1 H), 9.55 (s, 1 H), 7.61 (s, 1 H), 7.50 (s, 1 H), 7.32-7.37 (m, 5 H), 7.03 (m, 1 H), 6.87 (d, 2 H), 4.41 (s, 2 H), 3.99 (q, 2 H), 3.17 (m, 2 H), 2.92 (m, 2 H), 2.64 (m, 2 H), 2.42 (m, 2 H), 2.06 (m, 2 H), 1.10 (t, 3 H).

DCB-70198: $^1$H NMR (DMSO-d$_6$) δ 13.81 (s, 1 H), 11.05 (s, 1 H), 9.55 (s, 1 H), 7.66 (s, 1 H), 7.50 (s, 1 H), 7.34-7.36 (m, 5 H), 7.03 (m, 1 H), 6.88 (m, 1 H), 4.41 (s, 2 H), 3.15 (m, 2 H), 2.94 (m, 2H), 2.65 (m, 2 H), 2.43 (m, 2 H), 2.02 (m, 2 H).

DCB-70200: $^1$H NMR (DMSO-d$_6$) δ 13.84 (s, 1 H), 7.73 (d, 2 H), 7.51-7.58 (m, 4 H), 7.35 (s, 1 H), 6.70-6.76 (m, 2 H), 3.14 (m, 2 H), 2.63 (m, 2 H), 2.51 (s, 3 H), 2.45 (s, 3 H).

DCB-70201: $^1$H NMR (DMSO-d$_6$) δ 13.88 (s, 1 H), 10.96 (s, 1 H), 7.71 (m, 2 H), 7.59 (m, 1 H), 7.53 (m, 3 H), 7.45 (s, 1 H), 6.73 (s, 1 H), 4.01 (q, 2 H), 3.19 (m, 2 H), 2.63 (s, 3 H), 2.46 (m, 5 H), 2.04 (m, 2 H), 1.11 (t, 3 H).

DCB-70202: $^1$H NMR (DMSO-d$_6$) δ 13.80 (s, 1 H), 8.17 (s, 1 H), 7.90 (s, 1 H), 7.49 (m, 3 H), 7.39 (m, 1 H), 7.06 (d, 1 H), 4.87 (s, 2 H), 3.22 (m, 2 H), 2.63 (s, 3 H), 2.46 (m, 5 H).

DCB-70205: $^1$H NMR (DMSO-d$_6$) δ 13.79 (s, 1 H), 11.50 (s, 1 H), 8.18 (s, 1 H), 7.86 (s, 1 H), 7.47 (m, 3 H), 7.38 (m, 1 H), 7.06 (d, 1 H), 4.89 (s, 1 H), 3.33 (m, 2 H), 2.63 (s, 3 H), 2.51 (m, 2 H), 2.45 (m, 3 H), 2.13 (m, 7 H).

DCB-70206: $^1$H NMR (DMSO-d$_6$) δ 13.73 (s, 1 H), 8.20 (s, 1 H), 7.84 (s, 1 H), 7.52-7.58 (m, 2 H), 7.12-7.18 (m, 2 H), 6.94-7.00 (m, 2 H), 3.95 (q, 2 H), 3.27 (m, 2 H), 2.89 (m, 2 H), 2.61 (s, 1 H), 2.56 (m, 2 H), 2.44 (s, 3 H), 2.10 (m, 7 H).

DCB-70207: $^1$H NMR (DMSO-d$_6$) δ 13.92 (s, 1 H), 10.98 (s, 1 H), 7.68-7.73 (m, 2 H), 6.86 (m, 1H), 6.60 (m, 1 H), 3.32 (m, 2 H), 3.19 (m, 2 H), 2.61 (s, 3 H), 2.43 (m, 2 H), 2.12 (m, 7 H).

DCB-70209: $^1$H NMR (DMSO-d$_6$) δ 13.68 (s, 1 H), 8.27 (s, 1 H), 7.95 (s, 1 H), 7.48-7.51 (m, 3 H), 7.39 (m, 1 H), 7.06 (m, 1 H), 4.88 (s, 2 H), 4.01 (q, 2 H), 3.25 (m, 2 H), 2.94 (m, 2 H), 2.61 (m, 2H), 2.44 (m, 2 H), 2.06 (m, 2 H), 1.14 (t, 3 H).

DCB-70210: $^1$H NMR (DMSO-d$_6$) δ 13.64 (s, 1 H), 11.44 (s, 1 H), 8.32 (s, 1 H), 7.94 (s, 1 H), 7.55-7.59 (m, 2 H), 7.13-7.18 (m, 2 H), 6.95-7.00 (m, 2 H), 3.92-4.02 (m, 4 H), 3.28 (m, 2 H), 2.92 (m, 4 H), 2.62 (m, 2 H), 2.42 (m, 2 H), 2.05 (m, 2 H), 1.12 (t, 3 H).

DCB-70212: $^1$H NMR (DMSO-d$_6$) δ 13.76 (s, 1 H), 8.17 (s, 1 H), 7.86 (s, 1 H), 7.65 (m, 1 H), 7.49 (m, 3 H), 7.06 (m, 1 H), 4.87 (s, 2 H), 3.24 (m, 2 H), 2.97 (m, 2 H), 2.61 (s, 3 H), 2.45 (s, 3 H), 2.19-2.34 (m, 8 H), 0.75-0.78 (t, 6 H).

DCB-70213: $^1$H NMR (DMSO-d$_6$) δ 13.84 (s, 1 H), 10.97 (s, 1 H), 7.72 (s, 1 H), 7.65 (m, 1 H), 7.58 (m, 1 H), 6.95 (m, 1 H), 6.85 (m, 1 H), 3.21 (m, 2 H), 2.95 (m, 2 H), 2.59 (s, 3 H), 2.44 (s, 3H), 2.18-2.33 (m, 8 H), 0.77 (t, 6 H).

DCB-70214: $^1$H NMR (DMSO-d$_6$) δ 13.64 (s, 1 H), 8.18 (s, 1 H), 7.82 (s, 1 H), 7.66 (m, 1 H), 7.52-7.59 (m, 2 H), 7.17 (m, 1 H), 7.11 (d, 1 H), 6.93-6.99 (m, 2 H), 3.98 (q, 2 H), 3.26 (m, 2 H), 2.93 (m, 2 H), 2.58 (s, 3 H), 2.43 (s, 3 H), 2.35 (m, 2 H), 2.08-2.16 (m, 6 H), 0.65 (t, 6 H).

DCB-70218: $^1$H NMR (DMSO-d$_6$) δ 13.75 (s, 1 H), 10.96 (s, 1 H), 7.73 (d, s H), 7.53-7.59 (m, 4H), 7.41 (s, 1 H), 6.72-6.78 (m, 2 H), 3.41 (m, 4 H), 3.13 (m, 2 H), 2.91 (m, 2 H), 2.01-2.14 (m, 12H).

DCB-70219: $^1$H NMR (DMSO-d$_6$) δ 13.87 (s, 1 H), 10.94 (s, 1 H), 7.74 (d, 2 H), 7.48-7.59 (m, 4H), 7.39 (s, 1 H), 6.72-6.76 (m, 2 H), 3.39 (m, 2 H), 3.15 (m, 2 H), 2.60 (s, 3 H), 2.43 (m, 6 H), 2.10 (m, 9 H).

DCB-70222: $^1$H NMR (DMSO-d$_6$) δ 13.62 (s, 1 H), 8.10 (s, 1 H), 7.89 (s, 1 H), 7.48-7.51 (m, 4 H), 7.38-7.41 (m, 2 H), 7.07 (d, 1 H), 4.87 (s 2 H), 2.98 (m, 4 H), 2.41 (m, 6 H), 2.06 (m, 2 H), 1.68 (m, 2 H), 0.91 (t, 6 H); ESI-MS: 614 (M+1).

DCB-70223: $^1$H NMR (DMSO-d$_6$) δ 13.60 (s, 1 H), 8.19 (s, 1 H), 7.89 (s, 1 H), 7.64 (m, 1 H), 7.50 (m, 3 H), 7.40 (m, 1 H), 7.06 (m, 1 H), 4.87 (s, 2 H), 3.22 (m, 2 H), 2.94-2.99 (m, 4 H), 2.07-2.43 (m, 12 H), 0.77 (t, 6 H).

DCB-70224: $^1$H NMR (DMSO-d$_6$) δ 13.69 (s, 1 H), 10.98 (s, 1 H), 7.73 (s, 1 H), 7.60-7.64 (m, 2H), 6.94-6.97 (m, 1 H), 6.83-6.86 (m, 1 H), 3.18 (m, 2 H), 2.86-2.95 (m, 4 H), 2.04-2.39 (m, 12H), 0.77 (t, 6 H).

DCB-70225: $^1$H NMR (DMSO-d$_6$) δ 13.50 (s, 1 H), 8.21 (s, 1 H), 7.87 (s, 1 H), 7.51-7.66 (m, 3 H), 7.11-7.20 (m, 2 H), 6.93-7.00 (m, 2 H), 3.97 (m, 2 h), 3.25 (m, 2 H), 2.94 (m, 6 H), 2.36-2.43 (m, 4 H), 2.05-2.18 (m, 12 H), 0.67 (t, 3 H).

DCB-70226: $^1$H NMR (DMSO-d$_6$) δ 13.50 (s, 1 H), 11.39 (s, 1 H), 8.36 (s, 1 H), 7.86 (s, 1 H), 7.17 (m, 2 H), 7.07 (m, 1 H), 6.89 (m, 1 H), 6.58 (s, 1 H), 4.07 (m, 2 H), 3.66 (s, 1 H), 3.20 (m, 2 H), 3.05 (m, 2 H), 2.91 (m, 2 H), 2.54 (m, 2 H), 2.50 (m, 2 H), 2.06 (m, 2 H).

Example 3

Biological Activity

Various compounds of formula (I), (II), and (III) were tested for their ability to inhibit a variety of protein kinase such as Aurora A & B kinase, VEGFr-2, FGFr-1, PDGFr-β, c-kit, c-Met, and FLT3. Brief descriptions of different assays are described as follow.

A. Aurora Kinase Assays

Inhibition of Aurora Kinase by the compounds disclosed herein was determined by incubating Aurora kinase, substrate, and a test compound together for a period of time followed by quantifying the resultant phosphorylated product. Specifically, in a well of a 96-well round bottom plate, 25 μL of a reaction mixture containing (1) a test compound disclosed herein (diluted from 9 μM to the desired final concentration), [γ-33P]ATP/ATP mix (10 μM), CHOCKtide (1 μg, Genesis Biotech Inc.), and Aurora-A (1 ng, purchased from Upstate); or (2) a test compound disclosed herein (diluted from 9 μM to the desired final concentration), [γ-33P]ATP/ATP mix (40 μM), CHOCKtide (1 μg, Genesis Biotech Inc.), and Aurora-B (2.5 ng, purchased from Cell signaling); was prepared and incubated at 33° C. for 30 minutes. The reaction was then stopped by adding 5 μL of 3% phosphoric acid. The resultant solution (30 μL) was later harvested by a UniFilter Plate GF/B (PerkinElmer) followed by adding 30 μL of the scintillation cocktail (MicroScint 20, PerkinElmer) to the well. The radioactivity retained on the filter membrane was measured by a luminescence counter (PerkinElmer). Inhibition of Aurora A kinase and Aurora B kinase by various compounds listed in Table 1 are summarized and shown in Table 2 below. IC$_{50}$ value is defined as the concentration of the test compound which achieves a half-maximal inhibition of the kinase activity.

TABLE 2

| Compound ID | Aurora A kinase assay | | Aurora B kinase assay | |
|---|---|---|---|---|
| | Inhibition at 1.0 μM (%) | IC$_{50}$ (nM) | Inhibition at 1.0 μM (%) | IC$_{50}$ (nM) |
| DCB-70049 | 32.6 | 1,779 | 2.3 | 5,920 |
| DCB-70052 | 74.8 | 208.8 | 13.0 | —$^a$ |
| DCB-70053 | 38.2 | 1,983 | 3.5 | — |
| DCB-70055 | 79.8 | 177.8 | 11.6 | — |
| DCB-70056 | 55.0 | — | 7.2 | — |
| DCB-70057 | 89.5 | 210.7 | 6.8 | — |
| DCB-70058 | 17.7 | — | -1.0 | — |
| DCB-70059 | 76.1 | 357.3 | 12.4 | — |
| DCB-70062 | -7.2 | — | -4.1 | — |
| DCB-70063 | 56.6 | 723.5 | 3.4 | — |
| DCB-70064 | 78.6 | 313.2 | 22.2 | — |
| DCB-70065 | 97.3 | 30.8 | 25.6 | — |
| DCB-70066 | 40.1 | — | 25.3 | — |
| DCB-70067 | 5.2 | — | -1.3 | — |
| DCB-70068 | 54.0 | 559.6 | 5.1 | — |
| DCB-70069 | 16.5 | — | -2.6 | — |
| DCB-70070 | 31.4 | — | -2.7 | — |
| DCB-70071 | 82.1 | 270.5 | 11.2 | — |
| DCB-70072 | 71.1 | 443.3 | 15.5 | — |
| DCB-70073 | 65.5 | — | 9.4 | — |
| DCB-70074 | 19.3 | — | 15.1 | — |
| DCB-70075 | 92.4 | 86.3 | 55.8 | 456.4 |
| DCB-70076 | 40.7 | — | 7.4 | — |
| DCB-70077 | 57.0 | — | 47.5 | — |
| DCB-70078 | 91.6 | 46.1 | 63.4 | 438.4 |
| DCB-70079 | 8.8 | — | 16.0 | — |
| DCB-70080 | 40.3 | — | 35.2 | — |
| DCB-70081 | 27.7 | — | 30.6 | — |
| DCB-70082 | 81.7 | 223.7 | 47.1 | 2,245 |
| DCB-70083 | 13.2 | — | 12.8 | — |
| DCB-70084 | 10.9 | — | 17.9 | — |
| DCB-70085 | 11.2 | — | 10.7 | — |
| DCB-70086 | 5.8 | — | 17.8 | — |
| DCB-70087 | 99.7 | 7.3 | 66.2 | 441.3 |
| DCB-70088 | 99.3 | 28.8 | 48.8 | 1,867 |
| DCB-70091 | 7.6 | — | 10.8 | — |
| DCB-70092 | 9.4 | — | 9.9 | — |
| DCB-70093 | 70.5 | — | 14.7 | — |
| DCB-70094 | 75.2 | — | 15.5 | — |
| DCB-70095 | 94.3 | 61.2 | 34.1 | — |
| DCB-70096 | 38.6 | — | 15.1 | — |
| DCB-70097 | 64.7 | — | 14.2 | — |
| DCB-70098 | 4.0 | — | 19.5 | — |
| DCB-70099 | 47.5 | — | 30.0 | — |
| DCB-70100 | 9.9 | — | 13.2 | — |
| DCB-70101 | 38.5 | — | 17.7 | — |
| DCB-70102 | 88.8 | 83.5 | 74.3 | 213.5 |
| DCB-70103 | 98.9 | 12.3 | 80.1 | 155.9 |
| DCB-70104 | 83.6 | 251.7 | 12.8 | — |
| DCB-70106 | 99.0 | 8.1 | 70.6 | 291.5 |
| DCB-70107 | 36.0 | — | 23.7 | — |
| DCB-70108 | 7.5 | — | 6.8 | — |
| DCB-70109 | 69.1 | — | 1.8 | — |
| DCB-70114 | 99.9 | 14.0 | 60.7 | 494.5 |
| DCB-70115 | 99.4 | — | 32.5 | — |
| DCB-70116 | 100.5 | — | 7.0 | — |
| DCB-70117 | 34.9 | — | 5.3 | — |
| DCB-70118 | 81.2 | — | 3.2 | — |
| DCB-70119 | 95.4 | — | 7.3 | — |
| DCB-70120 | 50.5 | — | 21.5 | — |
| DCB-70121 | 97.9 | — | 46.5 | 1,717 |
| DCB-70122 | 34.1 | — | 8.3 | — |
| DCB-70123 | 78.1 | — | 13.3 | — |
| DCB-70124 | 11.9 | — | 1.4 | — |
| DCB-70125 | 39.7 | — | -0.1 | — |
| DCB-70128 | 5.1 | — | 13.5 | — |
| DCB-70129 | 15.6 | — | 5.8 | — |
| DCB-70130 | 22.7 | — | 12.2 | — |
| DCB-70131 | 70.7 | — | 44.5 | — |
| DCB-70132 | 33.4 | — | 26.9 | — |
| DCB-70133 | 2.6 | — | 6.0 | — |
| DCB-70134 | 16.4 | — | 5.7 | — |
| DCB-70135 | 7.4 | — | -6.6 | — |
| DCB-70136 | 26.4 | — | 0.1 | — |
| DCB-70137 | 12.6 | — | -3.3 | — |
| DCB-70138 | 18.5 | — | -0.9 | — |
| DCB-70139 | 45.5 | — | -2.0 | — |
| DCB-70140 | 31.1 | — | 5.2 | — |
| DCB-70141 | 9.8 | — | -23.0 | — |
| DCB-70142 | 27.1 | — | 2.4 | — |
| DCB-70143 | 31.8 | — | 9.1 | — |
| DCB-70144 | 82.0 | 270.3 | 61.9 | 448.3 |

TABLE 2-continued

| Compound ID | Aurora A kinase assay Inhibition at 1.0 µM (%) | IC$_{50}$ (nM) | Aurora B kinase assay Inhibition at 1.0 µM (%) | IC$_{50}$ (nM) |
|---|---|---|---|---|
| DCB-70145 | 90.3 | 45.7 | 75.2 | 449.3 |
| DCB-70146 | 81.3 | 86.3 | 75.1 | 438.6 |
| DCB-70147 | 91.9 | 68.4 | 61.3 | — |
| DCB-70148 | 80.7 | — | 30.2 | — |
| DCB-70149 | 77.5 | — | 18.7 | — |
| DCB-70150 | 8.9 | — | 18.0 | — |
| DCB-70151 | 37.2 | — | 23.6 | — |
| DCB-70152 | 2.3 | — | 5.5 | — |
| DCB-70153 | 8.8 | — | 8.0 | — |
| DCB-70154 | −0.3 | — | 2.8 | — |
| DCB-70155 | 75.6 | — | 10.7 | — |
| DCB-70156 | 8.7 | — | 1.31 | — |
| DCB-70157 | 13.0 | — | 6.9 | — |
| DCB-70158 | 5.2 | — | 6.1 | — |
| DCB-70159 | 13.9 | — | −5.5 | — |
| DCB-70160 | 5.0 | — | 6.1 | — |
| DCB-70161 | 78.8 | — | 14.6 | — |
| DCB-70162 | 14.4 | — | 60.9 | 632 |
| DCB-70163 | 44.9 | — | 89.7 | 107 |
| DCB-70164 | 32.0 | — | 65.2 | 510 |
| DCB-70165 | 31.2 | — | 55.8 | 423 |
| DCB-70166 | 48.8 | — | 13.0 | — |
| DCB-70167 | 86.4 | 133.85 | 19.8 | — |
| DCB-70168 | 53.4 | — | 30.6 | — |
| DCB-70169 | 79.6 | — | 31.0 | — |
| DCB-70170 | 10.5 | — | 2.8 | — |
| DCB-70171 | 73.0 | — | 17.4 | — |
| DCB-70172 | −3.1 | — | −3.2 | — |
| DCB-70173 | 13.6 | — | −9.8 | — |
| DCB-70174 | 2.4 | — | −11.4 | — |
| DCB-70175 | 30.7 | — | 8.4 | — |
| DCB-70176 | 52.3 | — | 15.2 | — |
| DCB-70177 | 81.6 | — | 22.5 | — |
| DCB-70178 | 31.2 | — | 1.9 | — |
| DCB-70179 | 59.9 | — | 40.1 | — |
| DCB-70180 | 71.5 | — | 47.4 | 866 |
| DCB-70183 | 13.2 | — | 13.9 | — |
| DCB-70184 | 6.6 | — | 6.8 | — |
| DCB-70186 | 66.1 | — | 47.4 | — |
| DCB-70187 | 62.8 | — | 17.5 | — |
| DCB-70188 | 95.5 | 31.7 | 53.2 | 758.9 |
| DCB-70189 | 91.4 | 77.9 | 84.0 | 176.8 |
| DCB-70190 | 97.0 | 31.53 | 80.0 | 245.5 |
| DCB-70191 | 20.4 | — | 21.2 | — |
| DCB-70192 | 40.6 | — | 21.0 | — |
| DCB-70193 | 74.3 | — | 36.7 | — |
| DCB-70194 | 85.3 | 150.55 | 41.7 | — |
| DCB-70195 | 73.1 | — | 47.5 | — |
| DCB-70196 | 91.8 | 61.45 | 55.8 | 673.05 |
| DCB-70197 | 48.7 | — | 39.9 | — |
| DCB-70198 | 96.1 | 62.75 | 69.8 | 402.2 |
| DCB-70200 | 93.1 | 60.6 | 57.3 | 870.2 |
| DCB-70201 | 48.2 | — | 36.6 | — |
| DCB-70202 | 40.2 | — | 7.3 | — |
| DCB-70205 | 11.3 | — | 2.4 | — |
| DCB-70206 | 37.4 | — | 21.1 | — |
| DCB-70207 | 10.3 | — | 6.8 | — |
| DCB-70209 | 22.7 | — | 16.3 | — |
| DCB-70210 | 74.6 | 100.4 | 45.5 | — |
| DCB-70212 | 3.5 | — | 6.3 | — |
| DCB-70213 | 1.0 | — | 16.4 | — |
| DCB-70214 | 15.4 | — | 14.8 | — |
| DCB-70218 | 62.0 | 823.3 | 54.2 | — |
| DCB-70219 | 25.7 | — | 14.8 | — |
| DCB-70222 | 95.7 | — | 83.2 | — |
| DCB-70223 | 68.5 | — | 43.7 | — |
| DCB-70224 | — | — | — | — |
| DCB-70225 | — | — | — | — |
| DCB-70226 | — | — | — | — |

$^a$not tested

B. VEGFR2 Kinase Assay

Inhibition of VEGFR2 kinase activity by compounds disclosed herein was quantified by measuring the amount of [$^{33}$P] incorporated into the substrate in the presence of a test compound. Specifically, a reaction mixture with a final volume of 25 µL and containing 6.25 ng of VEGFR2 kinase (obtained by purifying recombinant N-terminal 6×His-tagged VEGFR2 kinase domain construct expressed by baculovirus), 5 µg of substrate (Poly (Glu-Tyr, 4:1, Sigma)), kinase reaction buffer (20 mM MOPS pH 7.0, 1 mM EDTA, 5% glycerol, 0.01% Brij-35, 0.1% β-mercaptoethanol, 1 mg/mL BSA, 100 µM ATP, 0.1 µCi per well [$^{33}$P]-γ-ATP (2,500-3,000 Ci/mmol), and 500 nM test compound (final concentration of DMSO was 4%) or 4% DMSO alone (as the control sample), was incubated at 30° C. for 30 minutes. The reaction was then stopped by adding 5 µL of 3% phosphoric acid solution. The resultant solution was transferred to and harvested by a filter plate (UniFilter-96 GF/B, PerkinElmer). The filter plate was then washed 20 times with d.d. H$_2$O for 5 min followed by the addition of 30 µL of MicroScint™-20 Cocktail (PerkinElmer). After the plate was sealed, the retained radioactivity on the filter was counted using a TopCount scintillation detector (PerkinElmer). The percentage of inhibition rate of the test compound was calculated by dividing the retained radioactivity of the test sample with the retained radioactivity of the control sample and shown in Table 3.

C. PDGFR-β Kinase Assay

Inhibition of PDGFR-β kinase activity by compounds disclosed herein was quantified by measuring the amount of [$^{33}$P] incorporated into the substrate in the presence of a test compound. Briefly, a reaction mixture of 25 µL final volume containing 55 ng of PDGFR-β kinase (obtained by purifying recombinant N-terminal 6×His-tagged PDGFR-β kinase domain construct expressed by baculovirus), 2.5 µg of the substrate (Poly (Glu-Tyr, 4:1, Sigma)), kinase reaction buffer (20 mM MOPS pH 7.0, 1 mM EDTA, 5% glycerol, 0.01% Brij-35, 0.1% β-mercaptoethanol, 1 mg/mL BSA, 2 mM MnCl$_2$, 30 µM ATP, 0.1 µCi per well [$^{33}$P]-γ-ATP (2,500-3,000 Ci/mmol)), and a test compound (500 nM, diluted with 4% DMSO) or DMSO (as the control) was incubated at 30° C. for 30 minutes. The reaction was stopped by adding 5 µL of 3% phosphoric acid solution. The resultant reaction solution was then harvested onto a filter plate (UniFilter-96 GF/B, PerkinElmer), washed 20 times for 5 min with d.d. H$_2$O, and followed by the addition of 30 µL of MicroScint™-20 Cocktail (PerkinElmer). The plate was then sealed and counted using a TopCount scintillation detector (PerkinElmer). The percentage of inhibition rate of the test compound was calculated by dividing the retained radioactivity of the test sample with the retained radioactivity of the control sample and shown in Table 3.

D. c-Met Kinase Assay

Inhibition of c-Met kinase activity by compounds disclosed herein was quantified by measuring the amount of [$^{33}$P] incorporated into the substrate in the presence of a test compound. Briefly, a reaction mixture of 25 µL final volume containing 5 ng of c-Met kinase (obtained by purifying recombinant N-terminal 6×His-tagged c-Met kinase domain construct expressed from baculovirus), 1 µg of the substrate (Poly (Glu-Tyr, 4:1, Sigma)), kinase reaction buffer (20 mM MOPS pH 7.0, 1 mM EDTA, 5% glycerol, 0.01% Brij-35, 0.1% β-mercaptoethanol, 1 mg/mL BSA, 100 µM ATP, 0.1 µCi per well [$^{33}$P]-γ-ATP (2,500-3,000 Ci/mmol)), and a test compound (500 nM, diluted with 4% DMSO) or DMSO (as the control) was incubated at 30° C. for 30 minutes. The reaction was stopped by adding 5 µL of 3% phosphoric acid solution. The resultant reaction solution was then harvested onto a filter plate (UniFilter-96 GF/B, PerkinElmer), washed 20 times for 5 min with d.d. H$_2$O, and followed by the addition of 30 μL of MicroScint™-20 Cocktail (PerkinElmer). The plate was then sealed and counted using a TopCount scintillation detector (PerkinElmer). The percentage of inhibition rate of the test compound was calculated by dividing the retained radioactivity of the test sample with the retained radioactivity of the control sample and shown in Table 3.

E. Flt3 Kinase Assay

Inhibition of Flt3 kinase activity by compounds disclosed herein was quantified by measuring the amount of [$^{33}$P] incorporated into the substrate in the presence of a test compound. Briefly, a reaction mixture of 25 μL final volume containing 5 ng of Flt3 kinase (obtained by purifying recombinant N-terminal 6×His-tagged Flt3 kinase domain construct expressed from baculovirus), 5 μg of the substrate (Poly (Glu-Tyr, 4:1, Sigma)), kinase reaction buffer (20 mM MOPS pH 7.0, 1 mM EDTA, 5% glycerol, 0.01% Brij-35, 0.1% β-mercaptoethanol, 1 mg/mL BSA, 100 μM ATP, 0.1 μCi per well [$^{33}$P]-γ-ATP (2,500-3,000 Ci/mmol)), and a test compound (100 nM, diluted with 4% DMSO) or DMSO (as the control) was incubated at 30° C. for 30 minutes. The reaction was stopped by adding 5 μL of 3% phosphoric acid solution. The resultant reaction solution was then harvested onto a filter plate (UniFilter-96 GF/B, PerkinElmer), washed 20 times for 5 min with d.d. H$_2$O, and followed by the addition of 30 μL of MicroScint™-20 Cocktail (PerkinElmer). The plate was then sealed and counted using a TopCount scintillation detector (PerkinElmer). The percentage of inhibition rate of the test compound was calculated by dividing the retained radioactivity of the test sample with the retained radioactivity of the control sample and shown in Table 3.

TABLE 3

| Compound ID | Inhibition at 500 nM (%) | | | Inhibition at 100 nM (%) |
|---|---|---|---|---|
| | VEGFr-2 | PDGFr-β | c-Met | Flt-3 |
| DCB-70049 | 79.7 | 54.0 | 26.0 | 90.2 |
| DCB-70052 | 85.0 | 54.8 | 14.3 | 72.1 |
| DCB-70053 | 85.2 | 82.3 | 17.4 | 97.3 |
| DCB-70055 | 91.2 | 83.5 | 21.7 | 86.5 |
| DCB-70056 | 89.6 | 84.1 | 30.9 | 99.2 |
| DCB-70057 | 94.9 | 89.3 | 19.3 | 92.8 |
| DCB-70058 | 46.3 | 30.5 | 9.7 | 55.1 |
| DCB-70059 | 70.9 | 38.3 | 16.3 | 21.5 |
| DCB-70062 | 60.2 | 67.5 | 34.1 | 91.6 |
| DCB-70063 | 82.7 | 79.7 | 19.9 | 74.7 |
| DCB-70064 | 39.0 | 56.7 | 48.1 | 25.7 |
| DCB-70065 | 47.9 | 17.3 | 29.1 | -6.8 |
| DCB-70066 | 94.3 | 85.4 | 15.2 | 38.6 |
| DCB-70067 | 27.2 | 22.0 | 17.0 | 21.2 |
| DCB-70068 | 48.4 | 20.6 | 18.0 | 15.6 |
| DCB-70069 | 11.4 | 6.8 | -38.0 | 9.6 |
| DCB-70070 | 45.5 | 18.7 | 19.7 | 13.3 |
| DCB-70071 | 91.8 | 43.1 | 65.3 | 21.2 |
| DCB-70072 | 86.0 | 34.5 | 62.8 | -2.1 |
| DCB-70073 | 71.3 | 29.3 | 91.6 | 1.4 |
| DCB-70074 | 25.0 | 6.6 | 21.5 | -1.3 |
| DCB-70075 | 99.6 | 94.1 | 21.8 | 63.5 |
| DCB-70076 | 59.8 | 26.9 | 21.8 | -3.1 |
| DCB-70077 | 89.7 | 66.3 | 4.1 | 58.4 |
| DCB-70078 | 98.9 | 85.0 | -54.1 | 75.0 |
| DCB-70079 | 15.6 | 9.6 | 21.4 | 1.1 |
| DCB-70080 | 76.9 | 56.7 | -21.3 | 7.4 |
| DCB-70081 | 80.0 | 25.2 | 25.6 | 30.0 |
| DCB-70082 | 95.8 | 41.4 | 27.3 | 35.1 |
| DCB-70083 | 23.3 | 11.6 | 29.8 | 16.0 |
| DCB-70084 | 13.4 | 6.0 | 11.5 | -2.6 |
| DCB-70085 | 25.4 | 16.5 | 25.1 | 18.2 |
| DCB-70086 | 21.9 | 12.8 | 21.6 | 0.5 |
| DCB-70087 | 26.3 | 7.8 | 20.9 | 1.4 |
| DCB-70088 | 17.2 | 1.0 | 25.3 | -2.1 |
| DCB-70091 | 24.6 | 13.0 | -0.5 | 11.1 |
| DCB-70092 | 30.2 | 14.4 | 18.6 | 22.5 |

TABLE 3-continued

| Compound ID | Inhibition at 500 nM (%) | | | Inhibition at 100 nM (%) |
|---|---|---|---|---|
| | VEGFr-2 | PDGFr-β | c-Met | Flt-3 |
| DCB-70093 | 70.1 | 40.0 | 28.2 | 44.7 |
| DCB-70094 | 79.8 | 48.5 | 18.9 | 52.8 |
| DCB-70095 | 64.4 | 36.2 | 16.0 | 27.2 |
| DCB-70096 | 44.2 | 14.9 | 8.9 | 5.9 |
| DCB-70097 | 62.5 | 21.5 | 14.4 | 2.0 |
| DCB-70098 | 20.4 | 39.3 | 27.2 | 4.8 |
| DCB-70099 | 79.0 | 74.6 | 22.7 | 6.9 |
| DCB-70100 | 17.7 | 20.3 | 13.1 | 12.5 |
| DCB-70101 | 73.8 | 70.5 | 26.7 | 8.5 |
| DCB-70102 | 68.0 | 32.8 | 33.7 | 75.9 |
| DCB-70103 | 88.3 | 51.0 | 37.9 | 44.7 |
| DCB-70104 | 73.8 | 27.2 | 19.7 | 13.9 |
| DCB-70106 | 46.4 | 36.3 | 59.6 | 10.2 |
| DCB-70107 | 48.8 | 8.0 | 59.6 | 10.8 |
| DCB-70108 | 14.1 | 4.0 | 30.1 | 11.8 |
| DCB-70109 | 58.6 | 22.6 | -10.8 | 19.2 |
| DCB-70114 | 22.6 | 5.6 | 3.5 | 12.0 |
| DCB-70115 | 52.2 | 22.0 | 22.3 | 26.8 |
| DCB-70116 | 47.9 | 11.2 | 38.1 | 19.4 |
| DCB-70117 | 43.3 | 8.9 | 41.4 | 48.3 |
| DCB-70118 | 51.9 | 16.1 | 50.9 | 12.7 |
| DCB-70119 | 33.9 | 8.3 | 31.8 | -3.9 |
| DCB-70120 | 17.6 | 7.6 | 10.0 | 31.2 |
| DCB-70121 | 19.6 | 16.9 | -6.7 | 14.6 |
| DCB-70122 | 84.0 | 64.3 | 19.1 | 82.2 |
| DCB-70123 | 90.8 | 67.2 | 8.3 | 61.1 |
| DCB-70124 | 72.5 | 64.3 | -0.8 | 88.6 |
| DCB-70125 | 83.4 | 78.2 | 2.9 | 94.6 |
| DCB-70128 | 19.3 | 9.0 | 12.5 | 3.2 |
| DCB-70129 | 88.0 | 1.4 | 5.0 | 12.3 |
| DCB-70130 | 69.8 | 84.9 | 4.2 | 89.1 |
| DCB-70131 | 65.9 | 40.8 | -2.1 | 85.1 |
| DCB-70132 | 15.8 | 29.3 | 13.7 | 3.7 |
| DCB-70133 | 54.2 | 8.3 | 3.3 | 6.1 |
| DCB-70134 | 20.7 | 24.0 | -0.3 | 40.9 |
| DCB-70135 | 44.6 | 12.0 | -3.7 | 20.3 |
| DCB-70136 | 31.7 | 21.4 | -7.7 | 39.3 |
| DCB-70137 | 82.9 | 11.5 | 11.5 | 33.8 |
| DCB-70138 | 82.8 | 74.3 | 5.4 | 88.9 |
| DCB-70139 | 82.8 | 66.5 | -10.7 | 62.6 |
| DCB-70140 | 27.6 | 7.5 | 9.3 | 5.5 |
| DCB-70141 | 28.9 | 1.4 | -1.2 | 10.7 |
| DCB-70142 | 44.8 | 7.9 | —$^a$ | 11.8 |
| DCB-70143 | 38.1 | 1.0 | -8.2 | 6.0 |
| DCB-70144 | 40.8 | 2.4 | 14.4 | 38.7 |
| DCB-70145 | 66.6 | 14.5 | 12.5 | 24.0 |
| DCB-70146 | 59.7 | 19.7 | 20.9 | 59.9 |
| DCB-70147 | 71.3 | 17.3 | 0.2 | 43.8 |
| DCB-70148 | 67.6 | 16.1 | 74.9 | 9.7 |
| DCB-70149 | 57.5 | 10.8 | 8.4 | 7.3 |
| DCB-70150 | — | — | 0.2 | 17.1 |
| DCB-70151 | — | — | -6.5 | 42.2 |
| DCB-70152 | — | — | 94.1 | 31.7 |
| DCB-70153 | — | — | 95.8 | 52.5 |
| DCB-70154 | — | — | 47.9 | — |
| DCB-70155 | — | — | 9.1 | — |
| DCB-70156 | — | — | 28.3 | — |
| DCB-70157 | — | — | 85.6 | — |
| DCB-70158 | — | — | 85.4 | — |
| DCB-70159 | — | — | 81.3 | — |
| DCB-70160 | — | — | 59.1 | — |
| DCB-70161 | — | — | 59.7 | — |
| DCB-70162 | — | — | 98.3 | — |
| DCB-70163 | — | — | 92.9 | — |
| DCB-70164 | — | — | 72.6 | — |
| DCB-70165 | — | — | 73.8 | — |
| DCB-70166 | — | — | 21.6 | — |
| DCB-70167 | — | — | 11.8 | — |
| DCB-70168 | — | — | 12.7 | — |
| DCB-70169 | — | — | 10.8 | — |
| DCB-70170 | — | — | 13.1 | — |
| DCB-70171 | — | — | 18.2 | — |
| DCB-70172 | — | — | 10.4 | — |
| DCB-70173 | — | — | 13.7 | — |
| DCB-70174 | — | — | 4.0 | — |
| DCB-70175 | — | — | 17.3 | — |

TABLE 3-continued

| Compound ID | Inhibition at 500 nM (%) | | Inhibition at 100 nM (%) | |
|---|---|---|---|---|
| | VEGFr-2 | PDGFr-β | c-Met | Flt-3 |
| DCB-70176 | — | — | 10.1 | — |
| DCB-70177 | — | — | 18.8 | — |
| DCB-70178 | — | — | 7.8 | — |
| DCB-70179 | — | — | 17.9 | — |
| DCB-70180 | — | — | 5.1 | — |
| DCB-70183 | — | — | 1.5 | — |
| DCB-70184 | — | — | 8.7 | — |
| DCB-70186 | — | — | 9.6 | — |
| DCB-70187 | — | — | 8.8 | — |
| DCB-70188 | — | — | 51.1 | — |
| DCB-70189 | — | — | 14.0 | — |
| DCB-70190 | — | — | 10.0 | — |
| DCB-70191 | — | — | 19.0 | — |
| DCB-70192 | — | — | 9.9 | — |
| DCB-70193 | — | — | 11.2 | — |
| DCB-70194 | — | — | 12.9 | — |
| DCB-70195 | — | — | 15.3 | — |
| DCB-70196 | — | — | 13.8 | — |
| DCB-70197 | — | — | 21.1 | — |
| DCB-70198 | — | — | 20.2 | — |
| DCB-70200 | — | — | 15.2 | — |
| DCB-70201 | — | — | 18.8 | — |
| DCB-70202 | — | — | 85.2 | — |
| DCB-70205 | — | — | 97.0 | — |
| DCB-70206 | — | — | 77.4 | — |
| DCB-70207 | — | — | 21.1 | — |
| DCB-70209 | — | — | 92.1 | — |
| DCB-70210 | — | — | 75.3 | — |
| DCB-70212 | — | — | 95.2 | — |
| DCB-70213 | — | — | 15.5 | — |
| DCB-70214 | — | — | 56.3 | — |
| DCB-70218 | — | — | 9.2 | — |
| DCB-70219 | — | — | 17.7 | — |
| DCB-70222 | — | — | 95.6 | — |
| DCB-70223 | — | — | — | — |
| DCB-70224 | — | — | — | — |
| DCB-70225 | — | — | — | — |
| DCB-70226 | — | — | — | — |

$^a$not tested

Example 4

In Vivo Anti-Cancer Activity of (Z)-5-fluoro-3-((3-carboxyethyl-4-oxo-4,5,6,7-tetrahydro-1H-indol-2-yl)methylene)indolin-2-one (DCB-70055)

COLO 205 (1×10$^6$ cell/mouse) tumor cells were subcutaneously injected into the right flank of 5 week old male NOD/SCID mice (BioLASCO, Taiwan). Tumor volume was measured with a digital caliper once tumor was palpable (within 10 to 15 days after implantation). Compound treatment was started after 1-3 weeks when the tumors had reached an average volume of ~50 to 100 mm$^3$. Mice were divided into 5 groups as listed in Table 4 below and were given intravenous injections with test compound at different dosage (5 mg/kg, 10 mg/kg, or 20 mg/kg), SU11248 (20 mg/kg, positive control), or vehicle control (DMSO:Cremophor:PBS (pH 7.4)=5:10:8.5) one time every day. The test compound, DCB-70055, was formulated in a solution of 5% DMSO, 10% Cremophor, and 85% PBS. The positive control, SU11248, was dissolved in 100% PBS. Body weights of the mice were measured every two to three days and the tumor sizes in different groups of mice were measured by digital caliper every two to three days. Results indicated that DCB-70055 inhibited tumor growth in vivo without inducing significant weight loss.

TABLE 4

| group | mouse (n) | schedule | administration route |
|---|---|---|---|
| Vehicle control | 5 | qd × 14 | i.v. |
| SU11248 (20 mg/kg) | 5 | qd × 14 | i.v. |
| DCB-70055 (5 mg/kg) | 5 | qd × 14 | i.v. |
| DCB-70055 (10 mg/kg) | 5 | qd × 14 | i.v. |
| DCB-70055 (20 mg/kg) | 5 | qd × 14 | i.v. |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

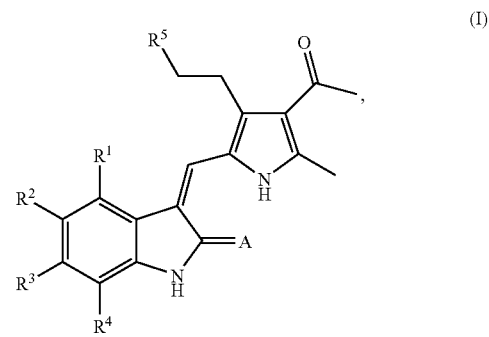

wherein

A is O or S;

R$^1$ is H, alkyl, alkenyl, alkynyl, halo, nitro, cyano, cycloalkyl, heterocycloalkyl, cycloalkenyl, heterocycloalkenyl, OR$^a$, NR$^a$R$^b$, —S(O)$_2$R$^a$, —S(O)$_2$NR$^a$R$^b$, —C(O)R$^a$, —C(O)NR$^a$R$^b$, —NR$^a$C(O)R$^b$, —NR$^a$S(O)$_2$R$^b$, —N=CR$^a$R$^b$, or —NR$^a$C(O)NHR$^b$, in which each of R$^a$ and R$^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or R$^a$ and R$^b$, together with the nitrogen atom to which they are bonded, are heteroaryl, heterocycloalkyl, or heterocycloalkenyl;

each of R$^2$, R$^3$, and R$^4$, independently, is H, halo, nitro, cyano, aryl, heteroaryl, cycloalkyl, heterocycloalkyl, cycloalkenyl, heterocycloalkenyl, OR$^a$, NR$^a$R$^b$, —S(O)$_2$ R$^a$, —S(O)$_2$NR$^a$R$^b$, —C(O)R$^a$, —C(O)NR$^a$R$^b$, —NR$^a$C(O)R$^b$, —NR$^a$S(O)$_2$R$^b$, —N=CR$^a$R$^b$, or —NR$^a$C(O)NHR$^b$; and R$^5$ is —C(O)OR$^c$, —C(O)R$^c$, —C(O)NR$^c$R$^d$, or —CH$_2$NR$^c$R$^d$, in which each of R$^c$ and R$^d$, independently, is H, alkyl, alkenyl, or alkynyl, or R$^c$ and R$^d$, together with the nitrogen atom to which they are bonded, are heteroaryl, heterocycloalkyl, or heterocycloalkenyl.

2. The compound of claim 1, wherein $R^5$ is —C(O)NR$^c$R$^d$ in which R$^c$ and R$^d$, together with the nitrogen atom to which they are bonded, are pyrrolidinyl, piperidinyl, piperazinyl, or morpholinyl, each optionally fused with aryl or heteroaryl, or heteroaryl.

3. The compound of claim 2, wherein $R^2$ is halo, —S(O)$_2$R$^a$, —S(O)$_2$NR$^a$R$^b$, or —NR$^a$S(O)$_2$R$^b$, in which each of R$^a$ and R$^b$, independently, is H, alkyl optionally substituted with aryl, aryl, or heteroaryl, or R$^a$ and R$^b$, together with the nitrogen atom to which they are bonded, are heteroaryl, heterocycloalkyl, or heterocycloalkenyl.

4. The compound of claim 3, wherein each of $R^1$, $R^3$, and $R^4$ is H.

5. The compound of claim 1, wherein at least one of $R^1$, $R^2$, $R^3$, and $R^4$ is —N=CR$^a$R$^b$ or —NR$^a$C(O)NHR$^b$.

6. The compound of claim 1, wherein $R^5$ is —C(O)OR$^{3\,c}$ in which R$^c$ is H or alkyl, or $R^5$ is —C(O)NR$^c$R$^d$ in which one of R$^c$ and R$^d$ is H and the other is alkyl substituted with alkylamino.

7. The compound of claim 6, wherein $R^2$ is halo, —S(O)$_2$R$^a$, —S(O)$_2$NR$^a$R$^b$, or —NR$^a$S(O)$_2$R$^b$, in which each of R$^a$ and R$^b$, independently, is H or alkyl optionally substituted with aryl, aryl, or heteroaryl, or R$^a$ and R$^b$, together with the nitrogen atom to which they are bonded, are heteroaryl, heterocycloalkyl, or heterocycloalkenyl.

8. The compound of claim 7, wherein each of $R^1$, $R^3$, and $R^4$ is H.

9. The compound of claim 1, wherein the compound is (Z)-3-(4-acetyl-2-((5-fluoro-2-oxoindolin-3-ylidene)methyl)-5-methyl-1H-pyrrol-3-yl)propanoic acid, (Z)-3-(4-acetyl-2-((5-(indolin-1-ylsulfonyl)-2-oxoindolin-3-ylidene)methyl)-5-methyl-1H-pyrrol-3-yl)propanoic acid, (Z)-3-(4-acetyl-5-methyl-2-(2-oxo-5-(phenylsulfonamido)indolin-3-ylidene)methyl)-1H-pyrrol-3-yl)propanoic acid, (Z)-ethyl3-(4-acetyl-5-methyl-2-((2-oxo-5-(phenylsulfonamido)indolin-3-ylidene)methyl)-1H-pyrrol-3-yl)propanoate, (Z)-3-(4-acetyl-2-((5-(2,6-dichlorobenzylsulfonyl)-2-oxoindolin-3-ylidene)methyl)-5-methyl-1H-pyrrol-3-yl)propanoic acid, (Z)-3-((4-acetyl-5-methyl-3-(3-(4-methylpiperazin-1-yl)-3-oxopropyl)-1H-pyrrol-2-yl)methylene)-5-(2,6-dichlorobenzylsulfonyl)indolin-2-one, (Z)-3-((4-acetyl-5-methyl-3-(3-(4-methylpiperazin-1-yl)-3-oxopropyl)-1H-pyrrol-2-yl)methylene)-5-(indolin-1-ylsulfonyl)indolin-2-one, (Z)-3-((4-acetyl-5-methyl-3-(3-(4-methylpiperazin-1-yl)-3-oxopropyl)-1H-pyrrol-2-yl)methylene)-5-fluoroindolin-2-one, (Z)-3-(4-acetyl-2-((5-(2,6-dichlorobenzylsulfonyl)-2-oxoindolin-3-ylidene)methyl)-5-methyl-1H-pyrrol-3-yl)-N-(2-(diethylamino)ethyl)propanamide, (Z)-3-(4-acetyl-2-((5-fluoro-2-oxoindolin-3-ylidene)methyl)-5-methyl-1H-pyrrol-3-yl)-N-(2-(diethylamino)ethyl)propanamide, (Z)-3-4-acetyl-2-((5-(indolin-1-ylsulfonyl)-2-oxoindolin-3-ylidene)methyl)-5-methyl-1H-pyrrol-3-yl)-N-(2-(diethylamino)ethyl)propanamide, or (Z)-N-(3-((4-acetyl-5-methyl-3-(3-(4-methylpiperazin-1-yl)-3-oxopropyl)-1H-pyrrol-2-yl)methylene)-2-oxoindolin-5-yl)benzenesulfonamide.

10. The compound of claim 1, wherein the compound is (Z)-3-(4-acetyl-5-methyl-2-((2-oxo-5-(phenylsulfonamido)indolin-3-ylidene)methyl)-1H-pyrrol-3-yl)propanoic acid, (Z)-3-(4-acetyl-2-((5-(2,6-dichlorobenzylsulfonyl)-2-oxoindolin-3-ylidene)methyl)-5-methyl-1H-pyrrol-3-yl)propanoic acid, (Z)-3-((4-acetyl-5-methyl-3-(3-(4-methylpiperazin-1-yl)-3-oxopropyl)-1H-pyrrol-2-yl)methylene)-5-(2,6-dichlorobenzylsulfonyl)indolin-2-one, or (Z)-3-(4-acetyl-2-((5-(2,6-dichlorobenzylsulfonyl)-2-oxoindolin-3-ylidene)methyl)-5-methyl-1H-pyrrol-3-yl)-N-(2-(diethyl amino)ethyl)propanamide.

11. A compound of formula (II):

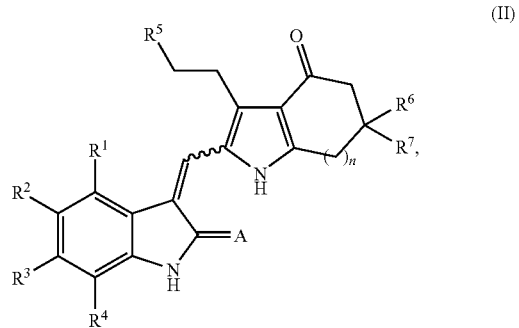

wherein
A is O or S;
each of $R^1$, $R^2$, $R^3$, and $R^4$, independently, is H, halo, nitro, cyano, aryl, heteroaryl, cycloalkyl, heterocycloalkyl, cycloalkenyl, heterocycloalkenyl, OR$^a$, NR$^a$R$^b$, —S(O)$_2$ R$^a$, —S(O)$_2$NR$^a$R$^b$, —C(O)R$^a$, —C(O)NR$^a$R$^b$, —NR$^a$C(O)R$^b$, —NR$^a$S(O)$_2$R$^b$, —N=CR$^a$R$^b$, or —NR$^a$C(O)NHR$^b$, in which each of R$^a$ and R$^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or R$^a$ and R$^b$, together with the nitrogen atom to which they are bonded, are heteroaryl, heterocycloalkyl, or heterocycloalkenyl;
$R^5$ is —C(O)OR$^c$, —C(O)R$^c$, —C(O)NR$^c$R$^d$, or —CH$_2$NR$^c$R$^d$, in which each of R$^c$ and R$^d$, independently, is H, alkyl, alkenyl, or alkynyl, or R$^c$ and R$^d$, together with the nitrogen atom to which they are bonded, are heteroaryl, heterocycloalkyl, or heterocycloalkenyl;
each of $R^6$ and $R^7$, independently, is H or alkyl; and
n is 1 or 2.

12. The compound of claim 11, wherein the compound is of formula (III):

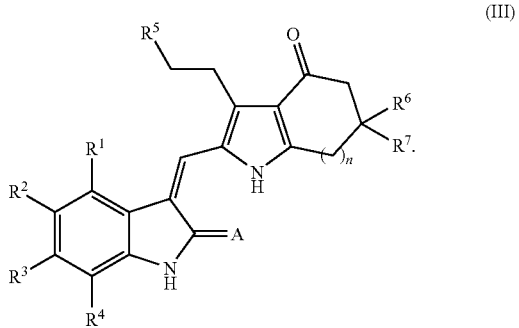

13. The compound of claim 12, wherein at least one of $R^1$, $R^2$, $R^3$, and $R^4$ is —N=CR$^a$R$^b$ or —NR$^a$C(O)NHR$^b$.

14. The compound of claim 13, wherein one of $R^2$ and $R^3$ is —N=CR$^a$R$^b$ or —NR$^a$C(O)NHR$^b$ and the other is H.

15. The compound of claim 14, wherein each of $R^1$ and $R^4$ is H and $R^5$ is —C(O)OR$^c$.

16. The compound of claim 15, wherein $R^6$ and $R^7$ are H or methyl.

17. The compound of claim 12, wherein $R^5$ is —C(O)NR$^c$R$^d$ in which R$^c$ and R$^d$, together with the nitrogen atom to which they are bonded, are pyrrolidinyl, piperidinyl, piperazinyl, morpholinyl, each optionally fused with aryl or heteroaryl, or heteroaryl.

18. The compound of claim 17, wherein one of $R^2$ and $R^3$ is halo, —S(O)$_2$R$^a$ or —S(O)$_2$NR$^a$R$^b$ and the other is H.

19. The compound of claim 18, wherein each of $R^1$ and $R^4$ is H.

20. The compound of claim 19, wherein $R^6$ and $R^7$ are H or methyl.

21. The compound of claim 12, wherein at least one of $R^2$, $R^3$, and $R^4$ is NR$^a$R$^b$, —S(O)$_2$NR$^a$R$^b$, or —C(O)NR$^a$R$^b$, in which R$^a$ and R$^b$, together with the nitrogen atom to which they are bonded, are pyrrolidinyl, piperidinyl, piperazinyl, morpholinyl, each optionally fused with aryl or heteroaryl, or heteroaryl.

22. The compound of claim 21, wherein $R^5$ is —C(O)OR$^c$.

23. The compound of claim 22, wherein each of $R^1$, $R^3$, and $R^4$ is H.

24. The compound of claim 12, wherein n is 2.

25. The compound of claim 24, wherein $R^2$ is —NR$^a$S(O)$_2$R$^b$.

26. The compound of claim 25, wherein $R^5$ is —C(O)OR$^c$ and each of $R^1$, $R^3$, $R^4$, $R^6$, $R^7$ is H.

27. The compound of claim 12, wherein $R^5$ is —C(O)OR$^c$ in which R$^c$ is H or alkyl.

28. The compound of claim 27, wherein one of $R^2$ and $R^3$ is H and the other is H, halo, nitro, aryl, —S(O)$_2$R$^a$, —S(O)$_2$NR$^a$R$^b$, or —NR$^a$S(O)$_2$R$^b$.

29. The compound of claim 28, wherein each of $R^1$ and $R^4$ is H.

30. The compound of claim 29, wherein $R^6$ and $R^7$ are H or methyl.

31. The compound of claim 11, wherein the compound is (Z)-3-((3-(3-ethoxy-3-oxopropyl)-4-oxo-4,5,6,7-tetrahydro-1H-indol-2-yl)methylene)indolin-2-one, (Z)-3-((3-carboxyethyl-4-oxo-4,5,6,7-tetrahydro-1H-indol-2-yl)methylene)indolin-2-one, (Z)-5-fluoro-3-((3-(3-ethoxy-3-oxopropyl)-4-oxo-4,5,6,7-tetrahydro-1H-indol-2-yl)methylene)indolin-2-one, (Z)-5-fluoro-3-((3-carboxyethyl-4-oxo-4,5,6,7-tetrahydro-1H-indol-2-yl)methylene)indolin-2-one, (Z)-5-bromo-3-((3-(3-ethoxy-3-oxopropyl)-4-oxo-4,5,6,7-tetrahydro-1H-indol-2-yemethylene)indolin-2-one, (Z)-5-bromo-3-((3-carboxyethyl-4-oxo-4,5,6,7-tetrahydro-1H-indol-2-yl)methylene)indolin-2-one, (Z)-5-(4-hydroxyl-3-methoxyphenyl)-3-((3-(3-ethoxy-3-oxopropyl)-4-oxo-4,5,6,7-tetrahydro-1H-indol-2-yl)methylene)indolin-2-one, (Z)-5-(4-hydroxyl-3-methoxyphenyl)-3-((3-carboxyethyl-4-oxo-4,5,6,7-tetrahydro-1H-indol-2-yl)methylene)indolin-2-one, (Z)-5-nitro-3-((3-(3-ethoxy-3-oxopropyl)-4-oxo-4,5,6,7-tetrahydro-1H-indol-2-yl)methylene)indolin-2-one, (Z)-5-nitro-3-((3-carboxyethyl-4-oxo-4,5,6,7-tetrahydro-1H-indol-2-yl)methylene)indolin-2-one, (Z)-5-(N-methylsulfamoyl)-3-((3-(3-ethoxy-3-oxopropyl)-4-oxo-4,5,6,7-tetrahydro-1H-indol-2-yl)methylene)indolin-2-one, (Z)-5-(N-methylsulfamoyl)-3-((3-carboxyethyl-4-oxo-4,5,6,7-tetrahydro-1H-indol-2-yl)methylene)indolin-2-one, (Z)-6-(4-hydroxyphenyl)-3-((3-(3-ethoxy-3-oxopropyl)-4-oxo-4,5,6,7-tetrahydro-1H-indol-2-yl)methylene)indolin-2-one, (Z)-5-(3,4-dimethoxyphenyl)-3-((3-(3-ethoxy-3-oxopropyl)-4-oxo-4,5,6,7-tetrahydro-1H-indol-2-yl)methylene)indolin-2-one, (Z)-5-(3,4-dimethoxyphenyl)-3-((3-carboxyethyl-4-oxo-4,5,6,7-tetrahydro-1H-indo-2-yl)methylene)indolin-2-one, (Z)-5-(benzo[b]thiophen-2-yl)-3-((3-(3-ethoxy-3-oxopropyl)-4-oxo-4,5,6,7-tetrahydro-1H-indol-2-yl)methylene)indolin-2-one, (Z)-5-(benzo[b]thiophen-2-yl)-3-(3-carboxyethyl-4-oxo-4,5,6,7-tetrahydro-1H-indol-2-yl)methylene)indolin-2-one, (Z)-5-benzylsulfonyl-3-((3-carboxyethyl-4-oxo-4,5,6,7-tetrahydro-1H-indol-2-yl)methylene)indolin-2-one, (Z)-5-(4-fluorobenzylsulfonyl)-3-((3-carboxyethyl-4-oxo-4,5,6,7-tetrahydro-1H-indol-2-yl)methylene)indolin-2-one, (Z)-5-(2,6-dichlorobenzylsulfonyl)-3-((3-carboxyethyl-4-oxo-4,5,6,7-tetrahydro-1H-indol-2-yl)methylene)indolin-2-one, (Z)-5-(4-fluorobenzamido)-3-((3-(3-ethoxy-3-oxopropyl)-4-oxo-4,5,6,7-tetrahydro-1H-indol-2-yl)methylene)indolin-2-one, (Z)-6-(4-hydroxyphenyl)-3-((3-carboxyethyl-4-oxo-4,5,6,7-tetrahydro-1H-indol-2-yl)methylene)indolin-2-one, (Z)-5-(4-fluorobenzamido)-3-((3-carboxyethyl-4-oxo-4,5,6,7-tetrahydro-1H-indol-2-yl)methylene)indolin-2-one, (Z)-6-(3,4-dihydroxyphenyl)-3-((3-(3-ethoxy-3-oxopropyl)-4-oxo-4,5,6,7-tetrahydro-1H-indol-2-yl)methylene)indolin-2-one, (Z)-6-(3,4-dihydroxyphenyl)-3-((3-carboxyethyl-4-oxo-4,5,6,7-tetrahydro-1H-indol-2-yl)methylene)indolin-2-one, (Z)-6-(benzo[b]thiophen-2-yl)-3-((3-(3-ethoxy-3-oxopropyl)-4-oxo-4,5,6,7-tetrahydro-1H-indol-2-yl)methylene)indolin-2-one, (Z)-6-(benzo[b]thiophen-2-yl)-3-((3-carboxyethyl-4-oxo-4,5,6,7-tetrahydro-1H-indol-2-yl)methylene)indolin-2-one, (Z)-6-(4-hydroxy-3-methoxyphenyl)-3-((3-(3-ethoxy-3-oxopropyl)-4-oxo-4,5,6,7-tetrahydro-1H-indol-2-yl)methylene)indolin-2-one, (Z)-6-(4-hydroxy-3-methoxyphenyl)-3-((3-carboxyethyl-4-oxo-4,5,6,7-tetrahydro-1H-indol-2-yl)methylene)indolin-2-one, 3-((3-(3-ethoxy-3-oxopropyl)-4-oxo-4,5,6,7-tetrahydro-1H-indol-2-yl)methylene)indolin-2-thione, 3-((3-carboxyethyl-4-oxo-4,5,6,7-tetrahydro-1H-indol-2-yl)methylene)indolin-2-thione, 6-bromo-3-((3-(3-ethoxy-3-oxopropyl)-4-oxo-4,5,6,7-tetrahydro-1H-indol-2-yl)methylene)indolin-2-thione, 6-bromo-3-((3-carboxyethyl-4-oxo-4,5,6,7-tetrahydro-1H-indol-2-yl)methylene)indolin-2-thione, (Z)-5-(pyrrolidin-1-ylsulfonyl)-3-((3-carboxyethyl-4-oxo-4,5,6,7-tetrahydro-1H-indol-2-yl)methylene)indolin-2-one, (Z)-5-morpholinosulfonyl-3-(3-carboxyethyl-4-oxo-4,5,6,7-tetrahydro-1H-indol-2-yl)methylene)indolin-2-one, (Z)-5-(3-p-tolylureido)-3-((3-(3-ethoxy-3-oxopropyl)-4-oxo-4,5,6,7-tetrahydro-1H-indol-2-yl)methylene)indolin-2-one, (Z)-5-(3-(4-methoxyphenyl)ureido)-3-((3-(3-ethoxy-3-oxopropyl)-4-oxo-4,5,6,7-tetrahydro-1H-indol-2-yl)methylene)indolin-2-one, (Z)-5-(3-p-tolylureido)-3-((3-carboxyethyl-4-oxo-4,5,6,7-tetrahydro-1H-indol-2-yl)methylene)indolin-2-one, (Z)-5-(3-(4-methoxyphenyl)ureido)-3-((3-carboxyethyl-4-oxo-4,5,6,7-tetrahydro-1H-indol-2-yl)methylene)indolin-2-one, (Z)-5-sulfamoyl-3-((3-carboxyethyl-4-oxo-4,5,6,7-tetrahydro-1H-indol-2-yl)methylene)indolin-2-one, (Z)-5-benazmido-3-((3-(3-ethoxy-3-oxopropyl)-4-oxo-4,5,6,7-tetrahydro-1H-indol-2-yl)methylene)indolin-2-one, (Z)-5-benazmido-3-((3-carboxyethyl-4-oxo-4,5,6,7-tetrahydro-1H-indol-2-yl)methylene)indolin-2-one, (Z)-6-(4-fluorophenyl)-3-((3-(3-ethoxy-3-oxopropyl)-4-oxo-4,5,6,7-tetrahydro-1H-indol-2-yl)methylene)indolin-2-one, (Z)-6-(4-fluorophenyl)-3-((3-carboxyethyl-4-oxo-4,5,6,7-tetrahydro-1H-indol-2-yl)methylene)indolin-2-one, (Z)-6-(3,5-difluorophenyl)-3-((3-(3-ethoxy-3-oxopropyl)-4-oxo-4,5,6,7-tetrahydro-1H-indol-2-yl)methylene)indolin-2-one, (Z)-6-(3,5-difluorophenyl)-3-((3-carboxyethyl-4-oxo-4,5,6,7-tetrahydro-1H-indol-2-yl)methylene)indolin-2-one, (Z)-5-phenylsulfonamido-3-((3-(3-ethoxy-3-oxopropyl)-4-oxo-4,5,6,7-tetrahydro-1H-indol-2-yl)methylene)indolin-2-one, (Z)-5-phenylsulfonamido-3-((3-carboxyethyl-4-oxo-4,5,6,7-tetrahydro-1H-indol-2-yl)methylene)indolin-2-one, (Z)-5-acetamido-3-((3-carboxyethyl-4-oxo-4,5,6,7-tetrahydro-1H-indol-2-yl)methylene)indolin-2-one, (Z)-5-(indolin-1-ylsulfonyl)-3-((3-carboxyethyl-4-oxo-4,5,6,7-tetrahydro-1H-indol-2-yl)methylene)indolin-2-one, (Z)-5-(4-methylpiperazin-1- ylsulfonyl)-3-((3-carboxyethyl-4-oxo-4,5,6,7-tetrahydro-1H-indol-2-yl)methylene)indolin-2-one hydrochloride, (Z)-5-(4-fluorophenyl)-3-((3-(3-ethoxy-3-oxopropyl)-4-oxo-4,5,6,7-tetrahydro-1H-indol-2-yl)methylene)indolin-2-one, (Z)-5-(4-fluorophenyl)-3-((3-carboxyethyl-4-oxo-4,5,6,7-tetrahydro-1H-indol-2-yl)methylene)indolin-2-one, (Z)-5-(piperidin-1-ylsulfonyl)-3-((3-carboxyethyl-4-oxo-4,5,6,7-tetrahydro-1H-indol-2-yl)methylene)indolin-2-one, (Z)-5-vinylsulfonyl-3-((3-carboxyethyl-4-oxo-4,5,6,7-tetrahydro-1H-indol-2-yl)methylene)indolin-2-one, (Z)-5-ethylsulfonyl-3-((3-carboxyethyl-4-oxo-4,5,6,7-tetrahydro-1H-indol-2-yl)methylene)indolin-2-one, (Z)-N-methyl-3-((3-(3-(4-methylpiperazin-1-yl)-3-oxopropyl)-4-oxo-4,5,6,7-tetrahydro-1H-indol-2-yl)methylene)-2-oxoindoline-5-sulfonamide, (Z)-5-ethylsulfonamido-3-((3-(3-ethoxy-3-oxopropyl)-4-oxo-4,5,6,7-tetrahydro-1H-indol-2-yl)methylene)indolin-2-one, (Z)-5-ethylsulfonamido-3-((3-carboxyethyl-4-oxo-4,5,6,7-tetrahydro-1H-indol-2-yl)methylene)indolin-2-one, (Z)-3-(3-(3-(4-methylpiperazin-1-yl)-3-oxopropyl)-4-oxo-4,5,6,7-tetrahydro-1H-indol-2-yl)methylene)-5-(pyrrolidin-1-ylsulfonyl)indolin-2-one, (Z)-5-(N,N-dimethylsulfamoyl)-3-((3-carboxyethyl-4-oxo-4,5,6,7-tetrahydro-1H-indol-2-yl)methylene)indolin-2-one, (Z)-6-fluoro-3-((3-(3-ethoxy-3-oxopropyl)-4-oxo-4,5,6,7-tetrahydro-1H-indol-2-yl)methylene)indolin-2-one, (Z)-6-fluoro-3-((3-carboxyethyl-4-oxo-4,5,6,7-tetrahydro-1H-indol-2-yl)methylene)indolin-2-one, (Z)-N,N-diethyl-3-(2-((5-fluoro-2-oxoindolin-3-ylidene)methyl)-4-oxo-4,5,6,7-tetrahydro-1H-indol-3-yl)propanamide, (Z)-5-fluoro-3-((3-(3-morpholino-3-oxopropyl)-4-oxo-4,5,6,7-tetrahydro-1H-indol-2-yl)methylene)indolin-2-one, (Z)-ethyl 3-(2-((benzo[d][1,3]dioxol-5-yl)-2-oxoindolin-3-ylidene)methyl)-4-oxo-4,5,6,7-tetrahydro-1H-indol-3-yl)propanoate, (Z)-ethyl 3-(2-((5-(3-naphthalen-1-ylureido)-2-oxoindolin-3-ylidene)methyl)-4-oxo-4,5,6,7-tetrahydro-1H-indol-3-yl)propanoate, (Z)-ethyl 3-(2-((6-bromo-2-oxoindolin-3-ylidene)methyl)-4-oxo-4,5,6,7-tetrahydro-1H-indol-3-yl)propanoate, (Z)-ethyl 3-(2-((5-(benzylamino)-2-oxoindolin-3-ylidene)methyl)-4-oxo-4,5,6,7-tetrahydro-1H-indol-3-yl)propanoate, (Z)-3-(2-((5-(benzylamino)-2-oxoindolin-3-ylidene)methyl)-4-oxo-4,5,6,7-tetrahydro-1H-indol-3-yl)propanoic acid, (Z)-3-(2-((6-bromo-2-oxoindolin-3-ylidene)methyl)-4-oxo-4,5,6,7-tetrahydro-1H-indol-3-yl)propanoic acid, (Z)-ethyl 3-(4-oxo-2-5-(3-phenylureido)indolin-3-ylidene)methyl)-4,5,6,7-tetrahydro-1H-indol-3-yl)propanoate, (Z)-ethyl 3-(2-((5-(3-(4-bromophenyl)ureido)-2-oxoindolin-3-ylidene)methyl)-4-oxo-4,5,6,7-tetrahydro-1H-indol-3-yl)propanoate, (Z)-ethyl 3424(54344-fluorophenyl)ureido)-2-oxoindolin-3-ylidene)methyl)-4-oxo-4,5,6,7-tetrahydro-1H-indol-3-yl)propanoate, (Z)-ethyl 3-(2-((5-(3-(4-chloro-3-(trifluoromethyl)phenyl)ureido)-2-oxoindolin-3-ylidene)methyl)-4-oxo-4,5,6,7-tetrahydro-1H-indol-3-yl)propanoate, (Z)-ethyl 3-(2-((5-fluoro-2-oxoindolin-3-ylidene)methyl)-4-oxo-1,4,5,6,7,8-hexahydrocyclohepta[b]pyrrol-3-yl)propanoate, (Z)-3-(2-((5-fluoro-2-oxoindolin-3-ylidene)methyl)-4-oxo-1,4,5,6,7,8-hexahydrocyclohepta[b]pyrrol-3-yl)propanoic acid, (Z)-ethyl 3-(2-((5-(4-nitrobenzamido)-2-oxoindolin-3-ylidene)methyl)-4-oxo-4,5,6,7-tetrahydro-1H-indol-3-yl)propanoate, 3-(2-((5-(4-methoxybenzamido)-2-oxoindolin-3-ylidene)methyl)-4-oxo-4,5,6,7-tetrahydro-1H-indol-3-yl)propanoate, (Z)-3-(2-((5-(4-nitrobenzamido)-2-oxoindolin-3-ylidene)methyl)-4-oxo-4,5,6,7-tetrahydro-1H-indol-3-yl)propanoic acid, (Z)-3-(2-((5-(4-methoxybenzamido)-2-oxoindolin-3-ylidene)methyl)-4-oxo-4,5,6,7-tetrahydro-1H-indol-3-yl)propanoic acid, (Z)-ethyl 3-(2-((5-(4-fluorophenylsulfonamido)-2-oxoindolin-3-ylidene)methyl)-4-oxo-4,5,6,7-tetrahydro-1H-indol-3-yl)propanoate, (Z)-3-(2-((5-(4-fluorophenylsulfonamido)-2-oxoindolin-3-ylidene)methyl)-4-oxo-4,5,6,7-tetrahydro-1H-indol-3-yl)propanoic acid, (Z)-ethyl 3-(4-oxo-2-((2-oxo-5-(phenylsulfonamido)indolin-3-ylidene)methyl)-1,4,5,6,7,8-hexahydrocyclohepta[b]pyrrol-3-yl)propanoate, (Z)-3-(4-oxo-2-((2-oxo-5-(phenylsulfonamido)indolin-3-ylidene)methyl)-1,4,5,6,7,8-hexahydrocyclohepta[b]pyrrol-3-yl)propanoic acid, (Z)-3-(2-((5-((N-(3-chlorophenyl)-N-methylsulfamoyl)-2-oxoindolin-3-ylidene)methyl)-4-oxo-1,4,5,6,7,8-hexahydrocyclohepta[b]pyrrol-3-yl)propanoic acid, (Z)-3-(2-((5-(N-(3-chloro-4-fluorophenyl)sulfamoyl)-2-oxoindolin-3-ylidene)methyl)-4-oxo-1,4,5,6,7,8-hexahydrocyclohepta[b]pyrrol-3-yl)propanoic acid, (Z)-ethyl 3-(2-((6-(4-hydroxyphenyl)-2-oxoindolin-3-ylidene)methyl)-4-oxo-1,4,5,6,7,8-hexahydrocyclohepta[b]pyrrol-3-yl)propanoate, (Z)-3-(2-((6-(4-hydroxyphenyl)-2-oxoindolin-3-ylidene)methyl)-4-oxo-1,4,5,6,7,8-hexahydrocyclohepta[b]pyrrol-3-yl)propanoic acid, (Z)-5-(2,6-dichlorobenzylsulfonyl)-3-((4-oxo-3-(3-oxo-3-(pyrrolidin-1-yl)propyl)-4,5,6,7-tetrahydro-1H-indol-2-yl)methylene)indolin-2-one, (Z)-5-(2,6-dichlorobenzylsulfonyl)-3-((3-(3-(4-methylpiperazin-1-yl)-3-oxopropyl)-4-oxo-4,5,6,7-tetrahydro-1H-indol-2-yl)methylene)indolin-2-one, (Z)-ethyl 3-(2-((5-methoxy-2-oxoindolin-3-ylidene)methyl)-4-oxo-1,4,5,6,7,8-hexahydrocyclohepta[b]pyrrol-3-yl)propanoate, (Z)-3-(2-((5-methoxy-2-oxoindolin-3-ylidene)methyl)-4-oxo-1,4,5,6,7,8-hexahydrocyclohepta[b]pyrrol-3-yl)propanoic acid, (Z)-5-fluoro-3-((3-(3-(4-methylpiperazin-1-yl)-3-oxopropyl)-4-oxo-4,5,6,7-tetrahydro-1H-indol-2-yl)methylene)indolin-2-one, (Z)-3-(2-((5-(2,6-dichlorobenzylsulfonyl)-2-oxoindolin-3-ylidene)methyl)-4-oxo-4,5,6,7-tetrahydro-1H-indol-3-yl)-N-methylpropanamide, (Z)-ethyl 3-(2-((5-(2,6-dichlorobenzylsulfonyl)-2-oxoindolin-3-ylidene)methyl)-6,6-dimethyl-4-oxo-4,5,6,7-tetrahydro-1H-indol-3-yl)propanoate, (Z)-3-(2-((5-(2,6-dichlorobenzylsulfonyl)-2-oxoindolin-3-ylidene)methyl)-6,6-dimethyl-4-oxo-4,5,6,7-tetrahydro-1H-indol-3-yl)propanoic acid, (Z)-ethyl 3-(2-((5-(indolin-1-ylsulfonyl)-2-oxoindolin-3-ylidene)methyl)-6,6-dimethyl-4-oxo-4,5,6,7-tetrahydro-1H-indol-3-yl)propanoate, (Z)-3-(2-((5-(indolin-1-ylsulfonyl)-2-oxoindolin-3-ylidene)methyl)-6,6-dimethyl-4-oxo-4,5,6,7-tetrahydro-1H-indol-3-yl)propanoic acid, (Z)-ethyl 3424(5-methoxy-2-oxoindolin-3-ylidene)methyl)-4-oxo-4,5,6,7-tetrahydro-1H-indol-3-yl)propanoate, (Z)-3-(2-((5-methoxy-2-oxoindolin-3-ylidene)methyl)-4-oxo-4,5,6,7-tetrahydro-1H-indol-3-yl)propanoic acid, (Z)-ethyl 3-(6,6-dimethyl-4-oxo-2-5-(phenylsulfonamido)indolin-3-ylidene)methyl)-4,5,6,7-tetrahydro-1H-indol-3-yl)propanoate, (Z)-3-(6,6-dimethyl-4-oxo-2-((2-oxo-5-(phenylsulfonamido)indolin-3-ylidene)methyl)-4,5,6,7-tetrahydro-1H-indol-3-yl)propanoic acid, (Z)-ethyl 3-(2-((6-(oct-1-ynyl)-2-oxoindolin-3-ylidene)methyl)-4-oxo-4,5,6,7-tetrahydro-1H-indol-3-yl)propanoate, (Z)-3-(2-((6-(oct-1-ynyl)-2-oxoindolin-3-ylidene)methyl)-4-oxo-4,5,6,7-tetrahydro-1H-indol-3-yl)propanoic acid, (Z)-ethyl 3-(2-((5-(oct-1-ynyl)-2-oxoindolin-3-ylidene)methyl)-4-oxo-4,5,6,7-tetrahydro-1H-indol-3-yl)propanoate, (Z)-3-(2-((5-(oct-1-ynyl)-2-oxoindolin-3-ylidene)methyl)-4-oxo-4,5,6,7-tetrahydro-1H-indol-3-yl)propanoic acid, ethyl 3-(2-((Z)-(5-(3-(1-adamantanyl)ureido)-2-oxoindolin-3-ylidene)methyl)-4-oxo-4,5,6,7-tetrahydro-1H-indol-3-yl)propanoate, (Z)-ethyl 3-(2-((5-(4-methoxybenzylamino)-2-oxoindolin-3-ylidene)methyl)-4-oxo-4,5,6,7-tetrahydro-1H-indol-3-yl)propanoate, (Z)-ethyl 3-(2-((5-(4-fluorobenzylamino)-2-oxoindolin-3-ylidene)methyl)-4-oxo-4,5,6,7-tetrahydro-1H-indol-3-yl)propanoate, ethyl 3-(4-oxo-2-((Z)-(2-oxo-5-((E)- pyridin-4-ylmethyleneamino)indolin-3-ylidene)methyl)-4,5,6,7-tetrahydro-1H-indol-3-yl)propanoate, ethyl 3-(2-((Z)-(5-((E)-4-fluoro-3-(trifluoromethyl)benzylideneamino)-2-oxoindolin-3-ylidene)methyl)-4-oxo-4,5,6,7-tetrahydro-1H-indol-3-yl)propanoate, (Z)-ethyl 3-(4-oxo-2-((2-oxo-5-(1-phenylethylamino)indolin-3-ylidene)methyl)-4,5,6,7-tetrahydro-1H-indol-3-yl)propanoate, ethyl 3-(4-oxo-2-((Z)-(2-oxo-5-((E)-thiophen-3-ylmethyleneamino)indolin-3-ylidene)methyl)-4,5,6,7-tetrahydro-1H-indol-3-yl))propanoate, (Z)-ethyl 3-(2-((5-(3-(2,4-difluorophenyl)ureido)-2-oxoindolin-3-ylidene)methyl)-4-oxo-4,5,6,7-tetrahydro-1H-indol-3-yl)propanoate, (Z)-ethyl 3424(5-(3-(2,4-dichlorophenyl)ureido)-2-oxoindolin-3-ylidene) methyl)-4-oxo-4,5,6,7-tetrahydro-1H-indol-3-yl)propanoate, (Z)-N-(2-aminophenyl)-3-(4-oxo-2-((2-oxo-5-(phenylsulfonamido)indolin-3-ylidene)methyl)-4,5,6,7-tetrahydro-1H-indol-3-yl)propanamide, (Z)-3-(4-acetyl-2-((5-fluoro-2-oxoindolin-3-ylidene)methyl)-5-methyl-1H-pyrrol-3-yl)propanoic acid, (Z)-3-(4-acetyl-2-((5-(indolin-1-ylsulfonyl)-2-oxoindolin-3-ylidene)methyl)-5-methyl-1H-pyrrol-3-yl)propanoic acid, (Z)-ethyl 3-(2-((5-(3,5-difluorophenylsulfonamido)-2-oxoindolin-3-ylidene)methyl)-4-oxo-4,5,6,7-tetrahydro-1H-indol-3-yl)propanoate, (Z)-3-(2-((5-(3,5-difluorophenylsulfonamido)-2-oxoindolin-3-ylidene)methyl)-4-oxo-4,5,6,7-tetrahydro-1H-indol-3-yl)propanoic acid, (Z)-ethyl 3-(2-((5-(naphthalene-2-sulfonamido)-2-oxoindolin-3-ylidene)methyl)-4-oxo-4,5,6,7-tetrahydro-1H-indol-3-yl)propanoate, (Z)-3-(2-((5-(naphthalene-2-sulfonamido)-2-oxoindolin-3-ylidene)methyl)-4-oxo-4,5,6,7-tetrahydro-1H-indol-3-yl)propanoic acid, (Z)-ethyl 3-(2-((5-(3,5-dichlorophenylsulfonamido)-2-oxoindolin-3-ylidene)methyl)-4-oxo-4,5,6,7-tetrahydro-1H-indol-3-yl)propanoate, (Z)-3-(2-((5-(3,5-dichlorophenylsulfonamido)-2-oxoindolin-3-ylidene)methyl)-4-oxo-4,5,6,7-tetrahydro-1H-indol-3-yl)propanoic acid, (Z)-ethyl 3-(2-((5-(3-methoxyphenylsulfonamido)-2-oxoindolin-3-ylidene)methyl)-4-oxo-4,5,6,7-tetrahydro-1H-indol-3-yl)propanoate, (Z)-3-(2-((5-(3-methoxyphenylsulfonamido)-2-oxoindolin-3-ylidene)methyl)-4-oxo-4,5,6,7-tetrahydro-1H-indol-3-yl)propanoic acid, (Z)-ethyl 3-(4-oxo-2-((2-oxo-5-(phenylmethylsulfonamido)indolin-3-ylidene)methyl)-4,5,6,7-tetrahydro-1H-indol-3-yl))propanoate, (Z)-3-(4-oxo-2-((2-oxo-5-(phenylmethylsulfonamido)indolin-3-ylidene)methyl)-4,5,6,7-tetrahydro-1H-indol-3-yl)propanoic acid, (Z)-ethyl 3424(542,6-dichlorobenzylsulfonyl)-2-oxoindolin-3-ylidene)methyl)-4-oxo-4,5,6,7-tetrahydro-1H-indol-3-yl)propanoate, (Z)-ethyl 3-(2-((5-(indolin-1-ylsulfonyl)-2-oxoindolin-3-ylidene)methyl)-4-oxo-4,5,6,7-tetrahydro-1H-indol-3-yl)propanoate, (Z)-N-(3-((3-(3-(4-methylpiperazin-1-yl)-3-oxopropyl)-4-oxo-4,5,6,7-tetrahydro-1H-indol-2-yl)methylene)-2-oxoindolin-5-yl)benzenesulfonamide, (Z)-5-(2,6-dichlorobenzylsulfonyl)-3-((3-(3-(diethylamino)propyl)-4-oxo-4,5,6,7-tetrahydro-1H-indol-2-yl)methylene)indolin-2-one, (Z)-3-(2-((5-(2,6-dichlorobenzylsulfonyl)-2-oxoindolin-3-ylidene)methyl)-4-oxo-4,5,6,7-tetrahydro-1H-indol-3-yl)-N-(2-(diethylamino)ethyl)propanamide, (Z)-N-(2-(diethylamino)ethyl)-3-(2-((5-fluoro-2-oxoindolin-3-ylidene)methyl)-4-oxo-4,5,6,7-tetrahydro-1H-indol-3-yl)propanamide, (Z)-N-(2-(diethylamino)ethyl)-3-(2-((5-(indolin-1-ylsulfonyl)-2-oxoindolin-3-ylidene)methyl)-4-oxo-4,5,6,7-tetrahydro-1H-indol-3-yl))propanamide, or (Z)-3-(2-((5-(indolin-1-ylsulfonyl)-6-methoxy-2-oxoindolin-3-ylidene)methyl)-4-oxo-4,5,6,7-tetrahydro-1H-indol-3-yl)propanoic acid.

32. The compound of claim 1, wherein the compound is (Z)-3-((3-(3-ethoxy-3-oxopropyl)-4-oxo-4,5,6,7-tetrahydro-1H-indol-2-yl)methylene)indolin-2-one, (Z)-5-fluoro-3-((3-(3-ethoxy-3-oxopropyl)-4-oxo-4,5,6,7-tetrahydro-1H-indol-2-yl)methylene)indolin-2-one, (Z)-5-fluoro-3-((3-carboxyethyl-4-oxo-4,5,6,7-tetrahydro-1H-indol-2-yl)methylene)indolin-2-one, (Z)-5-bromo-3-((3-(3-ethoxy-3-oxopropyl)-4-oxo-4,5,6,7-tetrahydro-1H-indol-2-yl)methylene)indolin-2-one, (Z)-5-bromo-3-((3-carboxyethyl-4-oxo-4,5,6,7-tetrahydro-1H-indol-2-yl)methylene)indolin-2-one, (Z)-5-nitro-3-((3-(3-ethoxy-3-oxopropyl)-4-oxo-4,5,6,7-tetrahydro-1H-indol-2-yl)methylene)indolin-2-one, (Z)-5-(N-methylsulfamoyl)-3-((3-carboxyethyl-4-oxo-4,5,6,7-tetrahydro-1H-indol-2-yl)methylene)indolin-2-one, (Z)-6-(4-hydroxyphenyl)-3-((3-(3-ethoxy-3-oxopropyl)-4-oxo-4,5,6,7-tetrahydro-1H-indol-2-yl)methylene)indolin-2-one, (Z)-5-benzylsulfonyl-3-((3-carboxyethyl-4-oxo-4,5,6,7-tetrahydro-1H-indol-2-yl)methylene)indolin-2-one, (Z)-5-(2,6-dichlorobenzylsulfonyl)-3-((3-carboxyethyl-4-oxo-4,5,6,7-tetrahydro-1H-indol-2-yl)methylene)indolin-2-one, (Z)-6-(4-hydroxyphenyl)-3-((3-carboxyethyl-4-oxo-4,5,6,7-tetrahydro-1H-indol-2-yl)methylene)indolin-2-one, (Z)-6-(3,4-dihydroxyphenyl)-3-((3-carboxyethyl-4-oxo-4,5,6,7-tetrahydro-1H-indol-2-yl)methylene)indolin-2-one, (Z)-5-(pyrrolidin-1-ylsulfonyl)-3-((3-carboxyethyl-4-oxo-4,5,6,7-tetrahydro-1H-indol-2-yl)methylene)indolin-2-one, (Z)-5-morpholinosulfonyl-3-((3-carboxyethyl-4-oxo-4,5,6,7-tetrahydro-1H-indol-2-yl)methylene)indolin-2-one, (Z)-5-sulfamoyl-3-((3-carboxyethyl-4-oxo-4,5,6,7-tetrahydro-1H-indol-2-yl)methylene)indolin-2-one, (Z)-5-phenylsulfonamido-3-((3-carboxyethyl-4-oxo-4,5,6,7-tetrahydro-1H-indol-2-yl)methylene)indolin-2-one, (Z)-5-(indolin-1-ylsulfonyl)-3-((3-carboxyethyl-4-oxo-4,5,6,7-tetrahydro-1H-indol-2-yl)methylene)indolin-2-one, (Z)-5-(piperidin-1-ylsulfonyl)-3-((3-carboxyethyl-4-oxo-4,5,6,7-tetrahydro-1H-indol-2-yl)methylene)indolin-2-one, (Z)-5-(N,N-dimethylsulfamoyl)-3-((3-carboxyethyl-4-oxo-4,5,6,7-tetrahydro-1H-indol-2-yl)methylene)indolin-2-one, (Z)-6-fluoro-3-((3-carboxyethyl-4-oxo-4,5,6,7-tetrahydro-1H-indol-2-yl)methylene)indolin-2-one, (Z)-5-fluoro-3-((3-(3-morpholino-3-oxopropyl)-4-oxo-4,5,6,7-tetrahydro-1H-indol-2-yl))methylene)indolin-2-one, (Z)-3-(2-((5-(4-fluorophenylsulfonamido)-2-oxoindolin-3-ylidene)methyl)-4-oxo-4,5,6,7-tetrahydro-1H-indol-3-yl)propanoic acid, (Z)-ethyl 3-(4-oxo-2-((2-oxo-5-(phenylsulfonamido)indolin-3-ylidene)methyl)-1,4,5,6,7,8-hexahydrocyclohepta[b]pyrrol-3-yl)propanoate, (Z)-3-(4-oxo-2-((2-oxo-5-(phenylsulfonamido)indolin-3-ylidene)methyl)-1,4,5,6,7,8-hexahydrocyclohepta[b]pyrrol-3-yl)propanoic acid, (Z)-5-(2,6-dichlorobenzylsulfonyl)-3-((4-oxo-3-(3-oxo-3-(pyrrolidin-1-yl)propyl)-4,5,6,7-tetrahydro-1H-indol-2-yl)methylene)indolin-2-one, (Z)-5-(2,6-dichlorobenzylsulfonyl)-3-((3-(3-(4-methylpiperazin-1-yl)-3-oxopropyl)-4-oxo-4,5,6,7-tetrahydro-1H-indol-2-yl)methylene)indolin-2-one, (Z)-3-(4-acetyl-2-((5-(indolin-1-ylsulfonyl)-2-oxoindolin-3-ylidene)methyl)-5-methyl-1H-pyrrol-3-yl)propanoic acid, (Z)-ethyl 3-(2-((5-(3,5-difluorophenylsulfonamido)-2-oxoindolin-3-ylidene)methyl)-4-oxo-4,5,6,7-tetrahydro-1H-indol-3-yl)propanoate, (Z)-3-(2-((5-(3,5-difluorophenylsulfonamido)-2-oxoindolin-3-ylidene)methyl)-4-oxo-4,5,6,7-tetrahydro-1H-indol-3-yl)propanoic acid, (Z)-3-(2-((5-(3-methoxyphenylsulfonamido)-2-oxoindolin-3-ylidene)methyl)-4-oxo-4,5,6,7-tetrahydro-1H-indol-3-yl)propanoic acid, (Z)-3-(4-oxo-2-((2-oxo-5-(phenylmethylsulfonamido)indolin-3-ylidene)methyl)-4,5,6,7-tetrahydro-1H-indol-3-yl)propanoic acid, (Z)-ethyl 3-(2-((5-(2,6-dichlorobenzylsulfonyl)-2-oxoindolin-3-ylidene)methyl)-4-oxo-4,5,6,7-tetrahydro-1H-indol-3-yl)propanoate, or (Z)-5-(2,6- dichlorobenzylsulfonyl)-3-((3-(3-(diethylamino)propyl)-4-oxo-4,5,6,7-tetrahydro-1H-indol-2-yl)methylene)indolin-2-one.

33. A pharmaceutical composition, comprising a compound of claim 1 and a pharmaceutically acceptable carrier.

34. A pharmaceutical composition, comprising a compound of claim 11 and a pharmaceutically acceptable carrier.

35. A method for treating colon cancer comprising administering to a subject in need thereof an effective amount of a compound of claim 1.

36. A method for treating colon cancer comprising administering to a subject in need thereof an effective amount of a compound of claim 11.

37. A method of decreasing the activity of at least one protein kinase comprising contacting the at least one protein kinase with a compound of claim 1.

38. The method of claim 37, wherein the at least one protein kinase is selected from the group consisting of Aurora A kinase, Aurora B kinase, VEGFr-2, FGFr-1, PDGFr-$\beta$, c-kit, c-Met, and FLT3.

39. A method of decreasing the activity of at least one protein kinase comprising contacting the at least one protein kinase with a compound of claim 11.

40. The method of claim 39, wherein the at least one protein kinase is selected from the group consisting of Aurora A kinase, Aurora B kinase, VEGFr-2, FGFr-1, PDGFr-$\beta$, c-kit, c-Met, and FLT3.

* * * * *